United States Patent
Tajima et al.

(10) Patent No.: US 9,649,086 B2
(45) Date of Patent: May 16, 2017

(54) RADIATION IMAGE CAPTURE DEVICE AND RADIATION IMAGE CAPTURE SYSTEM

(71) Applicant: FUJIFILM CORPORATION, Minato-ku, Tokyo (JP)

(72) Inventors: Takashi Tajima, Kanagawa (JP); Takeyasu Kobayashi, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 144 days.

(21) Appl. No.: 14/598,222

(22) Filed: Jan. 15, 2015

(65) Prior Publication Data
US 2015/0245807 A1    Sep. 3, 2015

(30) Foreign Application Priority Data
Mar. 3, 2014   (JP) .................. 2014-041014

(51) Int. Cl.
*A61B 6/00* (2006.01)

(52) U.S. Cl.
CPC ............ *A61B 6/563* (2013.01); *A61B 6/4233* (2013.01); *A61B 6/4266* (2013.01);
(Continued)

(58) Field of Classification Search
CPC combination set(s) only.
See application file for complete search history.

(56) References Cited

U.S. PATENT DOCUMENTS

| 6,975,752 B2 * | 12/2005 | Dixon .................. A61B 6/4233 250/370.09 |
| 2010/0014780 A1 * | 1/2010 | Kalayeh .................. G06T 1/00 382/284 |

(Continued)

FOREIGN PATENT DOCUMENTS

| JP | 2000-292546 A | 10/2000 |
| JP | 2010-17296 A | 1/2010 |

(Continued)

OTHER PUBLICATIONS

English language translation of the following: Office action dated Jan. 10, 2017 from the JPO in a Japanese patent application No. 2014-041014 corresponding to the instant patent application.

*Primary Examiner* — Phillip A Johnston
*Assistant Examiner* — Hsien Tsai
(74) *Attorney, Agent, or Firm* — SOLARIS Intellectual Property Group, PLLC

(57) ABSTRACT

A radiation image capture device includes plural radiation detection panels that each detect incident radiation that has passed through an imaging subject, that each generate a radiation image, and that are disposed in a row in a direction orthogonal to the radiation incident direction. The radiation image capture device designates a display target image from out of plural radiation images respectively generated by the plural radiation detection panels, and transmits the designated display target image to a console. At least a radiation image other than the display target image is stored in an image memory. The console displays on a display section the received display target image and, in response to data indicating a display request for a radiation image other than the display target image, also displays on the display section the radiation image other than the display target image read from the image memory.

27 Claims, 29 Drawing Sheets

(52) U.S. Cl.
    CPC .......... *A61B 6/5205* (2013.01); *A61B 6/5241* (2013.01); *A61B 6/5294* (2013.01); *A61B 6/542* (2013.01); *A61B 6/56* (2013.01); *A61B 6/486* (2013.01); *A61B 6/544* (2013.01)

(56) References Cited

U.S. PATENT DOCUMENTS

| | | |
|---|---|---|
| 2012/0049080 A1 | 3/2012 | Enomoto |
| 2014/0146155 A1* | 5/2014 | Gibby .................. G06T 7/0016 348/77 |

FOREIGN PATENT DOCUMENTS

| | | |
|---|---|---|
| JP | 2010-22752 A | 2/2010 |
| JP | 2010-259688 A | 11/2010 |
| JP | 2012-045159 A | 3/2012 |
| JP | 2013-226243 A | 11/2013 |

* cited by examiner

RADIATION IMAGE CAPTURE DEVICE AND RADIATION IMAGE CAPTURE SYSTEM

CROSS-REFERENCE TO RELATED APPLICATION

This application is based on and claims priority under 35 USC 119 from Japanese Patent Application No. 2014-041014 filed on Mar. 3, 2014, which is incorporated by reference herein.

BACKGROUND

Technical Field

The present invention relates to a radiation image capture device and a radiation image capture system.

Related Art

Recently, radiation detectors such as Flat Panel Detectors (FPDs) are being implemented, in which a radiation sensitive layer is disposed on a Thin Film Transistor (TFT) active matrix substrate and with which radiation can be converted directly into digital data. Radiation image capture devices such as electronic cassettes that employ such radiation detectors to generate radiation images expressing irradiated radiation are also being implemented. Radiation conversion methods to convert radiation into electrical signals include indirect conversion methods, in which radiation is first converted into light with a scintillator and then the converted light is converted into charges by a photodiode, and direct conversion methods in which radiation is converted into charges with a semiconductor layer including amorphous selenium or the like. There are various materials that can be used in the semiconductor layer of the radiation detection panel for each method.

In radiation image capture devices, a known example is one in which plural radiation detection panels are arranged in a row along the image capture plane in a long rectangle, so as to enable image capture spanning a comparatively wide region such as in X-ray image capture of a chest area. For example, in Japanese Patent-Application Laid-Open No. 2000-292546 (Patent Document 1), an X-ray image capture device is described in which sensor units provided with an X-ray detection means (CsI) is provided in an image capture plane of the image detection means (a Charge Coupling Device (CCD)) are disposed as X-ray image sensors in plural overlapping units spread over an image capture region such that portions of captured images overlap with each other, with the exterior shapes of the X-ray detection means encompassing the overlapping regions without exceeding the effective image capture region of each image detection means.

Moreover, a known system includes a radiation image detection device with an FPD, and a console, connected together so as to be capable of communication with each other. For example, JP-A No. 2010-22752 (Patent Document 2) and JP-A No. 2010-17296 (Patent Document 3) describe medical image systems that include an FPD cassette and a console.

The FPD cassette of Patent Document 2 and Patent Document 2 includes: a radiation detection means arrayed in two dimensions with plural elements converting radiation that has passed through an imaging subject into electrical signals; a reading means that reads the electrical signals acquired using the radiation detection means and generates image data of the imaging subject; a divided image data generation means that divides the image data generated by the reading means into divided image data; a transmission management means that sets a transmission sequence for the divided data; and a detection device communication means that externally transmits the divided image data to the according to the transmission sequence. The consoles described in Patent Document 2 and Patent Document 3 include a display means including a two dimensional shaped display region, and a console communication means that acquires divided image data from the FPD cassette, and a display control means that controls the display means.

According to Patent Document 2, the detection device communication means transmits division settings and a transmission sequence as auxiliary data, together with the divided image data, and the display control means, together with dividing the display region of the display means into plural divided display regions based on the division settings in the auxiliary data, the display control means also allocates the divided image data acquired by the console communication means to the respective divided display regions based on the transmission sequence in the auxiliary data, and displays on the display means.

According to Patent Document 3, the display control means, together with dividing the display region of the display means into plural divided display regions based on image capture position data, the display control means also allocates divided image data acquired by the console communication means to respective divided display regions according to a specified allocation sequence, and displays on the respective divided display regions.

As described in Patent Document 1, it is possible to achieve image capture spanning a comparatively large region by configuring a long rectangular shaped radiation image capture device in which plural radiation detection panels are joined together. However, sometimes it is desirable to carry out radiation image capture using only some of the radiation detection panels configuring the long rectangular shaped radiation image capture device. In such cases, if all of the images generated by each of the plural radiation detection panels are transmitted to an external device including a display section such as the console, the time until the images are displayed on the external device becomes long, and workflow is decreased.

In such cases, transmission of only the images generated by the radiation detection panel employed for image capture (also referred to as the employed panel below) to an external device, such as a console, may be considered. The number of images transmitted from the radiation image detection device to the external device such as the console can thereby be reduced, enabling the time waiting until image display to be shortened. However, it is conceivable that in some cases the imaging subject might also be captured by a radiation detection panel other than the employed panel, or that the employed panel might not be appropriately designated. In such cases, in cases in which image capture is not performed in the radiation detection panel other than the employed panel, image recapture is sometimes necessary in cases in which the image generated by the radiation detection panel other than the employed panel is not saved.

SUMMARY

In consideration of the above circumstance, an object of the present invention is to make the waiting time until the image display on an external display device shorter than hitherto, while avoiding the risk of image recapture when an image generated by some radiation detection panels, out of plural radiation detection panels disposed side-by-side along a direction orthogonal to the incidence direction of the radiation, is displayed on a display section of an external device.

According to an aspect of the present invention, a radiation image capture device is provided including plural radiation detection panels that each detect incident radiation that has passed through an imaging subject, that each generate a radiation image, and that are disposed in a row in a direction orthogonal to the radiation incident direction, a designation section that designates a display target image from the plural radiation images respectively generated by the plural radiation detection panels, and a transmission section that transmits to the outside of the radiation image capture device at least the display target image from the plural radiation images.

According to an aspect of the present invention, a radiation image capture system is provided including the above radiation image capture device, a storage medium that stores at least a radiation image other than the display target image from the plurality of radiation images, and a controller including a display controller that displays the display target image received from the radiation image capture device on a display section, and in cases in which a display request has been made, displays on the display section together with the display target image the radiation image other than the display target image stored on the storage medium.

BRIEF DESCRIPTION OF THE DRAWINGS

Exemplary embodiments of the present invention will be described in detail based on the following figures, wherein.

DETAILED DESCRIPTION

Figure 1:
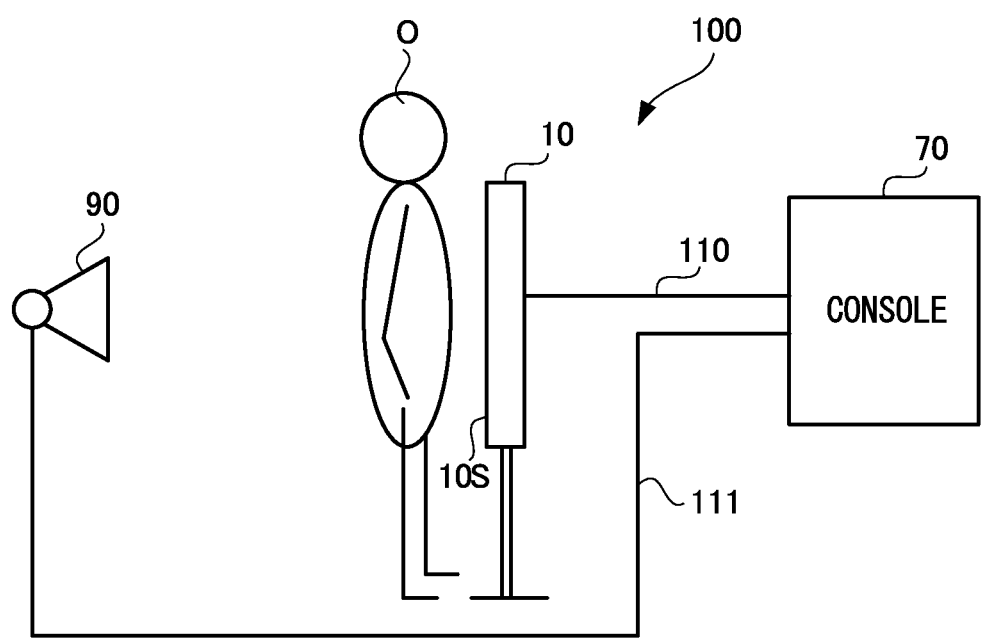
FIG. 1 is a diagram illustrating a configuration of a radiation image capture system 100 according to an exemplary embodiment of the present invention.

Detailed explanation follows regarding embodiments for implementing the present invention, with reference to the drawings. The same configuration elements in each of the drawings are appended with the same reference numerals.

First Exemplary Embodiment

FIG. 1 illustrates a configuration of a radiation image capture system 100 according to an exemplary embodiment of the present invention. The radiation image capture system 100 is configured including a radiation image capture device 10, a console 70, and a radiation irradiation device 90. The radiation image capture device 10 is an example of a radiation image capture device of the present invention, and the console 70 is an example of a controller of the present invention.

The radiation irradiation device 90 includes a function to cause X-rays to be irradiated toward an imaging subject O according to X-ray conditions notified by the console 70 (tube voltage, tube current, and irradiation time). The radiation image capture device 10 generates a radiation image according to a dose distribution of X-rays that have passed through the imaging subject O and arrived at an image capture plane 10S, and includes a function for transmitting the generated radiation image to the console 70. The console 70 performs overall control of the radiation irradiation device 90 and the radiation image capture device 10, and includes a function to display radiation images transmitted from the radiation image capture device 10. The console 70 and the radiation image capture device 10, and the console 70 and the radiation irradiation device 90, transmit and receive image data, control signals, and the like through communication cables 110, and 111, respectively. Wireless communication may be configured between the console 70 and the radiation image capture device 10, and between the console 70 and the radiation irradiation device 90, and the communication cables 110 and 111 are unnecessary in such cases.

Figure 2:
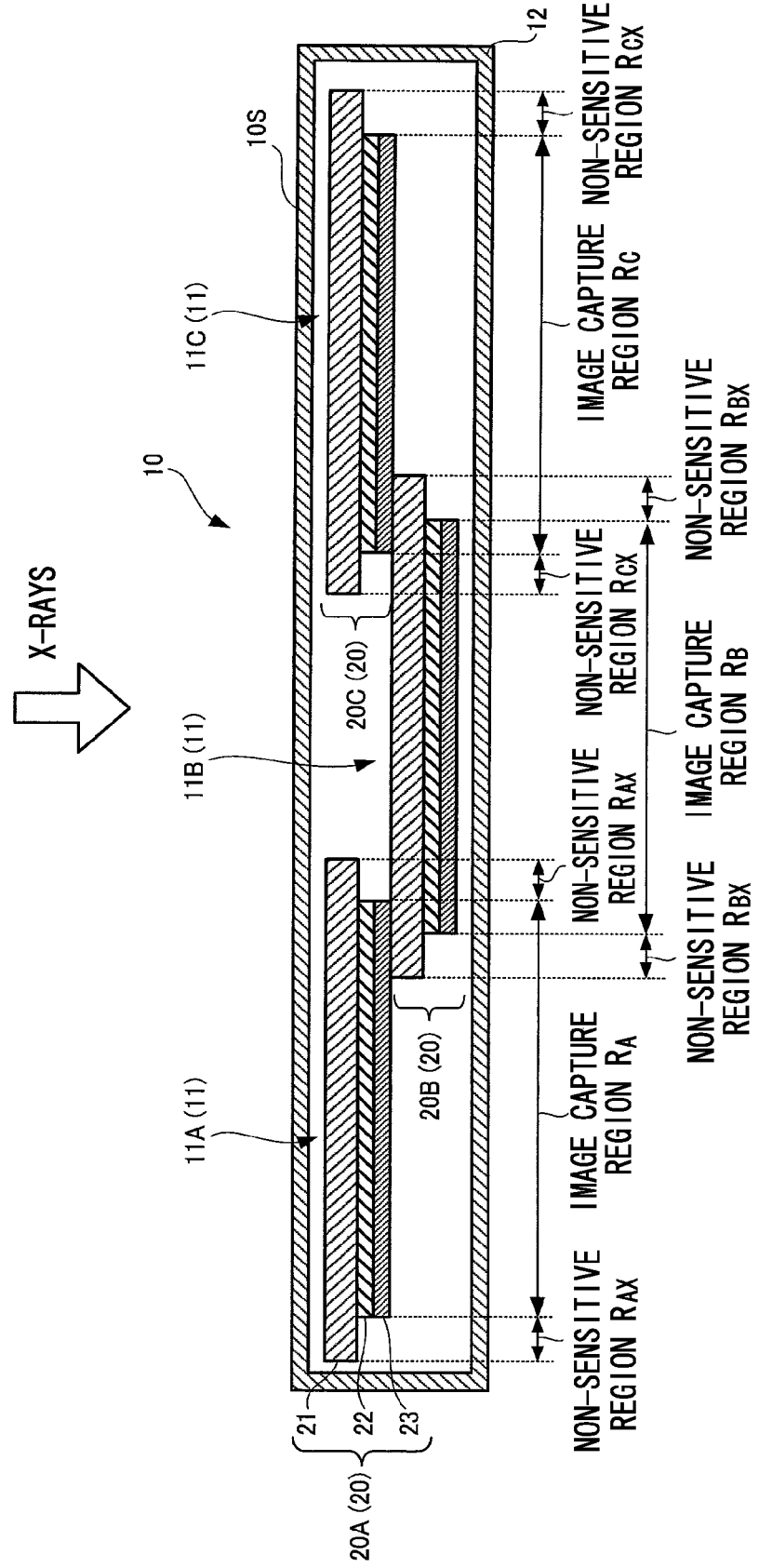
FIG. 2 is a cross-section diagram illustrating a structure of a radiation image capture device according to an exemplary embodiment of the present invention.

FIG. 2 is a cross-section diagram illustrating a structure of the radiation image capture device 10. As illustrated in FIG. 2, the radiation image capture device 10 includes a casing 12, and 3 image capture units 11A, 11B, 11C housed within the casing 12. The image capture units 11A, 11B, 11C each have the same configuration as each other, and respectively include radiation detection panels 20A, 20B, 20C configured including stacked layers of a TFT substrate 21, a photoelectric conversion layer 22, and a scintillator 23. In FIG. 2, configuration elements other than the radiation detection panels 20A, 20B, 20C (such as a gate line driver 41, a signal processor 42, and an image capture unit controller 50, see FIG. 5) are omitted from illustration. The radiation detection panels 20A, 20B, 20C are examples of radiation detection panels of the present invention. In the following the image capture units 11A, 11B, 11C will be referred to as the image capture units 11 when not discriminating between each other and when being referred to collectively. The radiation detection panels 20A, 20B, 20C will likewise be referred to as the radiation detection panels 20 when not discriminating between each other and when being referred to collectively.

The scintillator 23 includes a phosphor that absorbs radiation and radiates visible light. In cases in which X-rays are employed as the radiation, cesium iodide (CsI) is preferably included as the phosphor employed in the scintillator 23, and thallium doped cesium iodide (CsI(Tl)) having a light emission spectrum of from 400 nm to 700 nm on irradiation with X-rays is particularly preferable.

The photoelectric conversion layer 22 is provided between the scintillator 23 and the TFT substrate 21, and is configured with an organic photoelectric conversion material to generate charge by absorbing light emitted from the scintillator 23. The photoelectric conversion layer 22 including the organic photoelectric conversion material has a sharp absorption spectrum in the visible region, and hardly any electromagnetic waves other than the visible light emitted from the scintillator 23 are absorbed in the photoelectric conversion layer 22. This thereby enables effective control of noise generated by radiation, such as X-rays, being absorbed by the photoelectric conversion layer 22. The organic photoelectric conversion material configuring the photoelectric conversion layer 22 preferably has an absorption peak wavelength as close as possible to the emission peak wavelength of the scintillator 23. Examples of organic photoelectric conversion materials capable of satisfying such a condition include quinacridone-based organic compounds and phthalocyanine-based organic compounds. Although omitted in the drawings, electrodes are provided on each side of the photoelectric conversion layer 22, and a bias voltage is applied to the photoelectric conversion layer 22 through these electrodes during image capture. The electrode on the TFT substrate 21 side is divided in a matrix pattern to correspond to the plural pixels.

The TFT substrate 21 is configured including a glass substrate provided with switching elements (TFT 34 in FIG. 3) for reading charges generated in the photoelectric conversion layer 22.

In the radiation detection panels 20A, 20B, 20C, the peripheral end portions of the TFT substrates 21 configure non-sensitive regions $R_{AX}$, $R_{BX}$, $R_{CX}$ that are not layered with the photoelectric conversion layer 22 nor the scintillator 23, and the insides adjacent to the non-sensitive regions $R_{AX}$, $R_{BX}$, $R_{CX}$ (the center sides of the radiation detection panels 20) configure image capture regions $R_A$, $R_B$, $R_C$ that are layered with the photoelectric conversion layer 22 and the scintillator 23. A radiation image can be generated in the respective image capture regions $R_A$, $R_B$, $R_C$.

In the radiation image capture device 10, the radiation detection panels 20A, 20B, 20C are placed in a row along a direction intersecting with the incident direction of X-rays. More specifically, one end portion of the image capture region $R_A$ in the radiation detection panel 20A overlaps in the X-ray incident direction with one end portion of the image capture region $R_B$ of the radiation detection panel 20B, and the other end portion of the image capture region $R_B$ overlaps in the X-ray incident direction with one end portion of the image capture region $R_C$ of the radiation detection panel 20C. Both ends of the centrally placed radiation detection panel 20B are placed at the X-ray incident direction downstream side of the radiation detection panels 20A and 20C. Thus in the radiation image capture device 10, a long rectangular shaped image capture region is formed by connecting the three radiation detection panels 20A, 20B, 20C together. In mutually adjacent radiation detection panels, the continuity of the image capture region can be maintained by overlapping the end portions of the image capture regions. Namely, non-continuous portions of the image capture region (namely missing image portions) can be prevented from occurring at the joints between radiation detection panels, even in cases in which there is a change in the relative positions of the radiation detection panels 20A, 20B, 20C due to manufacturing variance, impact, vibration, change in ambient temperature, or the like. Moreover, non-continuous portions of the image capture region can be prevented from occurring even in cases in which X-rays are incident at an oblique angle to the image capture plane 10S.

The radiation image capture device 10 is placed with the photoelectric conversion layer 22 on the incident side of the X-rays, and employs what is referred to as an irradiation side sampling (ISS) image capture method. Adopting the irradiation side sampling method enables the distance between the high intensity radiation position of the scintillator 23 and the photoelectric conversion layer 22 to be shortened in comparison to cases in which what is referred to as a penetration side sampling (PSS) is employed, and, as a result, enables the resolution of the radiation image to be raised. The radiation image capture device 10 may adopt a penetration side sampling method, and may be a configuration including these methods.

Figure 3:
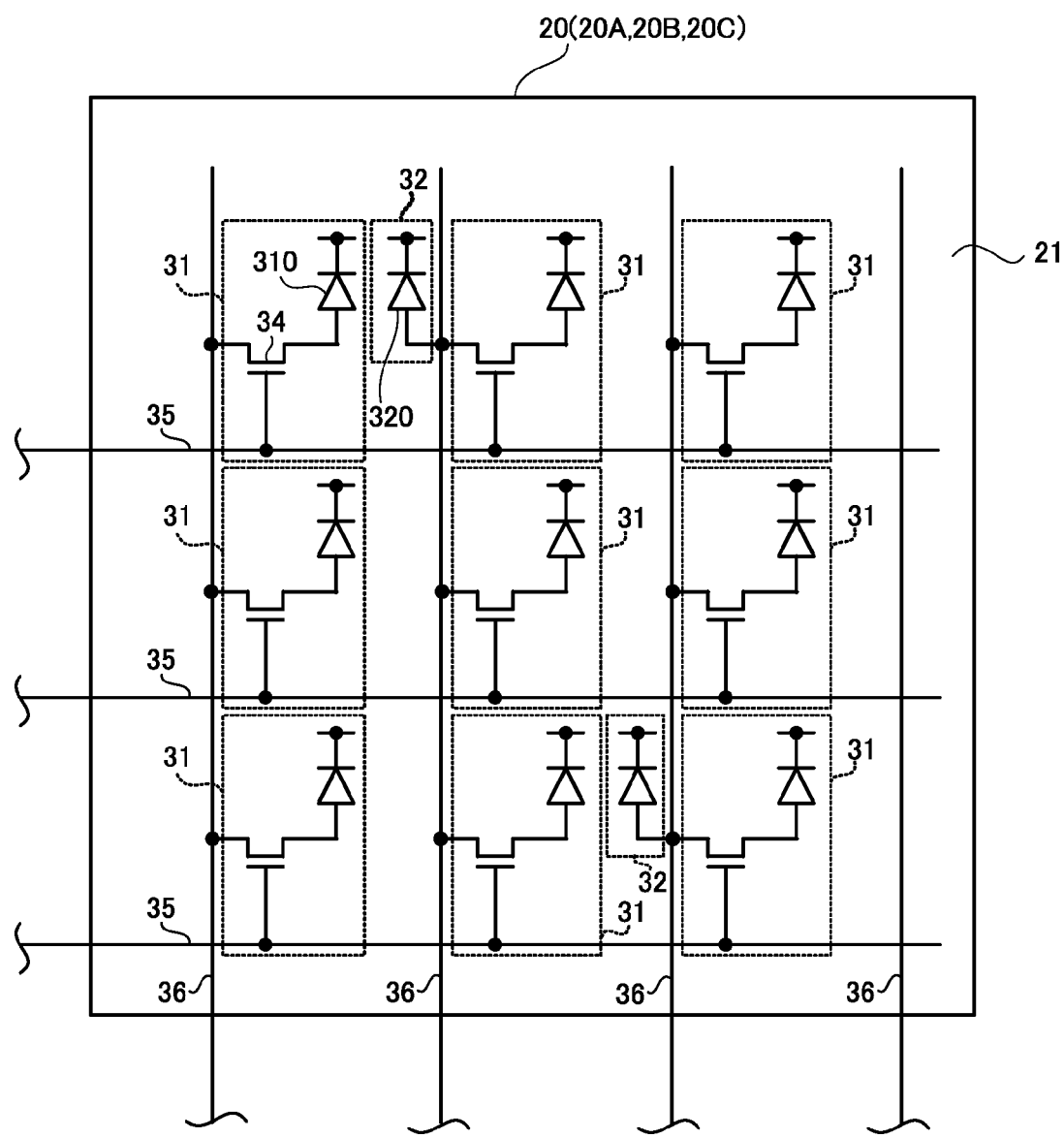
FIG. 3 is a diagram illustrating an electrical configuration of a radiation detection panel according to an exemplary embodiment of the present invention.

FIG. 3 is a diagram illustrating an electrical configuration of the radiation detection panels 20. The radiation detection panels 20 not only have a function to generate a radiation image, but also have an irradiation detection function to detect the presence or absence of irradiated radiation. In order to implement the above irradiation detection function, in addition to plural image capture pixels 31 for capturing radiation images, the radiation detection panels 20 also include plural irradiation detection pixels 32 for detecting the presence or absence of X-ray irradiation.

Each of the image capture pixels 31 includes a radiation image capture sensor 310 configured including the photoelectric conversion layer 22, and a TFT 34 serving as a switching element that adopts an ON state during reading of charges generated in the sensors 310. The image capture pixels 31 are laid out in a two dimensional array so as to form rows and columns over the entire face of the TFT substrate 21.

The radiation detection panels 20 include plural gate lines 35 that extend in a specific direction (row direction) along the array of the image capture pixels 31, and that supply a gate signal to each of the TFTs 34 for switching each of the TFTs 34 ON/OFF. The radiation detection panels 20 also include plural signal lines 36 that extend in a direction intersecting with the extension direction of the gate lines 35 (column direction), and that read charges generated in the sensors 310 through the TFTs 34 that are in the ON state. Each of the image capture pixels 31 is provided so as to correspond with a respective intersection portion between the gate lines 35 and the signal lines 36.

The irradiation detection pixels 32 are configured by irradiation detection sensors 320 configured to include the photoelectric conversion layer 22. The irradiation detection sensors 320 are directly connected to the signal lines 36, and charges generated in the irradiation detection sensors 320 flow as they are through the signal lines 36. The irradiation detection sensors 320 are distributed across the entire region of the TFT substrate 21. In the present exemplary embodiment, the number of the irradiation detection sensors 320 is less than the number of the radiation image capture sensors 310. Namely, the irradiation detection pixels 32 are formed at a lower density on the TFT substrate 21 than the image capture pixels 31. A bias voltage is supplied through a bias line, not illustrated in the drawings, to the radiation image capture sensors 310 and the irradiation detection sensors 320, which both output a detection signal of magnitude according to the dose of irradiated radiation. The radiation image capture sensors 310 and the irradiation detection sensors 320 may be the same size as each other, or different sizes to each other. In the present exemplary embodiment, the irradiation detection pixels 32 are employed as a mechanism to detect the presence or absence of X-ray irradiation, however there is no limitation thereto, and, for example, it is possible to employ another mechanism as described below.

(1) Pixels freely selected out of the image capture pixels 31 may be made to function as pixels that exclusively detect the presence or absence of X-ray irradiation (irradiation detection pixels). In such cases, the sources and drains of the TFT 34 in the image capture pixels 31 that function as the irradiation detection pixels may be shorted (shorted pixel method).

(2) A bias current detection means may be provided to detect a bias current flowing in each of the radiation image capture sensors 310 accompanying application of a bias voltage to each of the radiation image capture sensors 310, and the presence or absence of X-ray irradiation may be detected based on the magnitude of the bias current detected by the bias current detection means.

(3) Additional TFTs may be provided to pixels selected out of the image capture pixels 31, and the presence or absence of X-ray irradiation may be detected based on leak current of the additionally provided TFTs.

(4) The magnitude of current flowing from the gate line driver 41 to each of the gate lines 35 may be detected, and the presence or absence of X-ray irradiation may be detected based on the magnitude of the detected current.

(5) Sensors that detect the presence or absence of radiation irradiation may be provided in a different layer to the layer in which the image capture pixels 31 are provided in the radiation detection panels 20. The sensors for detecting the presence or absence of radiation irradiation may also be provided as a separate body from the radiation detection panels 20.

Figure 4:
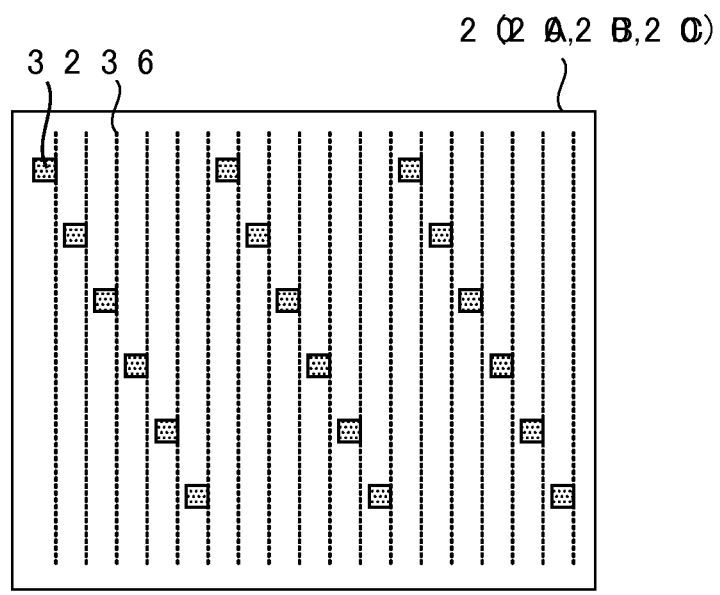
FIG. 4 is a plan view illustrating a placement of radiation detection image capture elements on a radiation detection panel of according to an exemplary embodiment of the present invention.

FIG. 4 is a plan view illustrating an example of a placement of the irradiation detection pixels 32 on the radiation detection panels 20. Each of the irradiation detection pixels 32 is connected to the respective signal line 36, and the irradiation detection pixels 32 are placed so as to be uniformly distributed within the radiation detection panels 20. FIG. 4 illustrates a case in which one of the irradiation detection pixels 32 is connected to one of the signal lines 36, however plural adjacent irradiation detection pixels 32 in the extension direction of the signal lines 36 may be connected to one of the signal lines 36. In such cases, the charges generated by the plural irradiation detection pixels 32 connected to the same signal line 36 merge in the signal line 36 and are thereby summed. In the present exemplary embodiment, the irradiation detection pixels 32 are configured together with the image capture pixels 31 on the TFT substrate 21, however, irradiation detection pixels 32 may be provided in a different layer from the image capture pixels 31.

Figure 5:
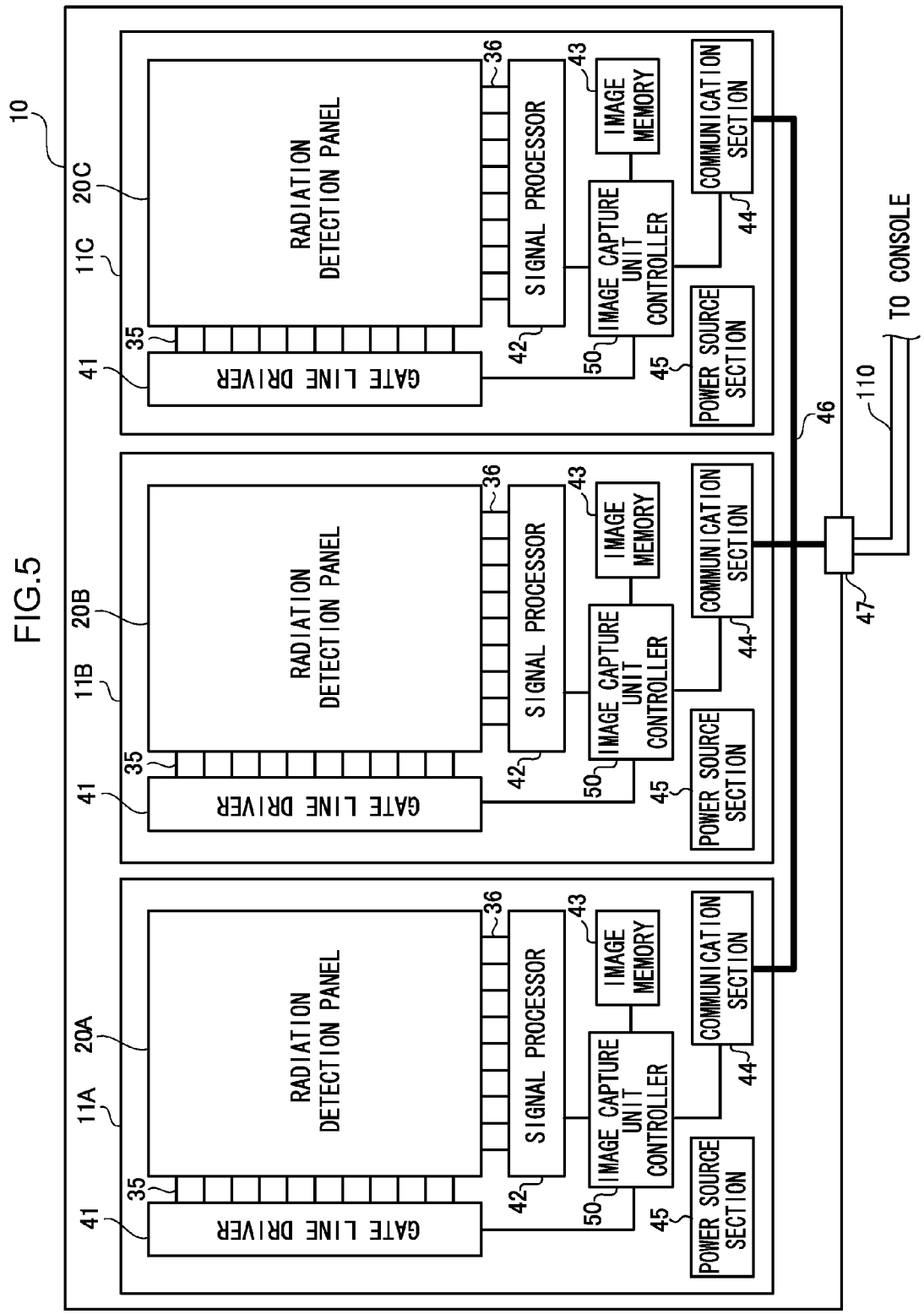
FIG. 5 is a block diagram illustrating an electrical configuration of a radiation image capture device according to an exemplary embodiment of the present invention.

FIG. 5 is a block diagram illustrating an overall electrical configuration of the radiation image capture device 10 configured including the three image capture units 11A, 11B, 11C. The image capture unit 11A includes a gate line driver 41 disposed along one side out of two adjacent sides of the radiation detection panel 20A, and a signal processor 42 disposed along the other side. Each of the gate lines 35 is connected to the gate line driver 41, and each of the signal lines 36 is connected to the signal processor 42. The image capture unit 11A includes an image memory 43, a communication section 44, a power source section 45, and the image capture unit controller 50. The image capture units 11B and 11C have a similar configuration to that of the image capture unit 11A, and so redundant explanation of the image capture units 11B and 11C is omitted.

In the radiation detection panels 20A, 20B, 20C, the TFTs 34 configuring the image capture pixels 31 are made to adopt an ON state in row units by supplying a gate signal from the gate line driver 41 through the gate lines 35 (see FIG. 3, FIG. 5). Due to the TFTs 34 adopting the ON state, the charges generated in the radiation image capture sensors 310 are read as electrical signals by each of the signal lines 36, and transmitted to the signal processor 42 (see FIG. 3, FIG. 5). The charges generated in the irradiation detection sensors 320 configuring the irradiation detection pixels 32 flow out through the signal lines 36 irrespective of the gate signals from the gate line driver 41, and are transmitted to the signal processor 42 (see FIG. 3, FIG. 5).

The signal processor 42 includes an amplifier and a sample-and-hold circuit (not illustrated in the drawings) provided separately for each of the signal lines 36. The charge signals transmitted to the individual signal lines 36 are amplified by the amplifiers in the signal processor 42 and then held in the sample-and-hold circuits. A multiplexer and an analogue-to-digital (A/D) converter (not illustrated in the drawings) are connected in sequence to the output side of the sample-and-hold circuits. The charge signals held in the individual sample-and-hold circuits are input in sequence to the multiplexer, are converted into digital signals by the A/D converter, and supplied to the image capture unit controller 50. As image data, the image capture unit controller 50 generates data in which the digital signal generated by the A/D converter is associated with position data of the image capture pixels 31.

The image memory 43 is connected to the image capture unit controller 50, and the image data generated in the image capture unit controller 50 is stored in the image memory 43. The image memory 43 includes storage capacity capable of storing plural frames worth of image data, and each time image capture of a radiation image is performed, the image data obtained by image capture is sequentially stored in the image memory 43. The image memory 43 according to the first exemplary embodiment of the present invention is an example of a storage medium of the present invention. Moreover, in the present exemplary embodiment, the image memories 43 are configurations inbuilt to the image capture units 11, however the image memories 43 may be detachably installed to the image capture units 11.

The communication section 44 controls communication between other image capture units 11 and the console 70 that are external devices. The image capture units 11A, 11B, 11C are connected together so as to be capable of communicating with each other using a communication line 46 connected to the communication section 44. The image capture units 11A, 11B, 11C thereby share various data. It is moreover possible to synchronize operation between the image capture units 11A, 11B, 11C. The communication sections 44 of the image capture units 11A, 11B, 11C are each connected to a communication terminal 47 through the communication line 46. One end of the communication cable 110 is connected to the console communication terminal 47, and the other end of the communication cable 110 is connected to the console 70. The image capture units 11A, 11B, 11C perform transmission and reception of image data, control signals, and the like with the console 70 through the communication cable 110.

The power source section 45 supplies power to each of the configuration elements of the image capture units 11 (the radiation detection panels 20, the image capture unit controllers 50, the gate line drivers 41, the signal processors 42, the image memories 43, and the communication sections 44). Power lines connecting the power source section 45 to each of the circuits are omitted from illustration in FIG. 5. The present exemplary embodiment is configured with respective power source sections 45 provided to each of the image capture units 11A, 11B, 11C, however there is no limitation thereto, as long as at least one power source section is provided to the radiation image capture device 10.

Figure 6:
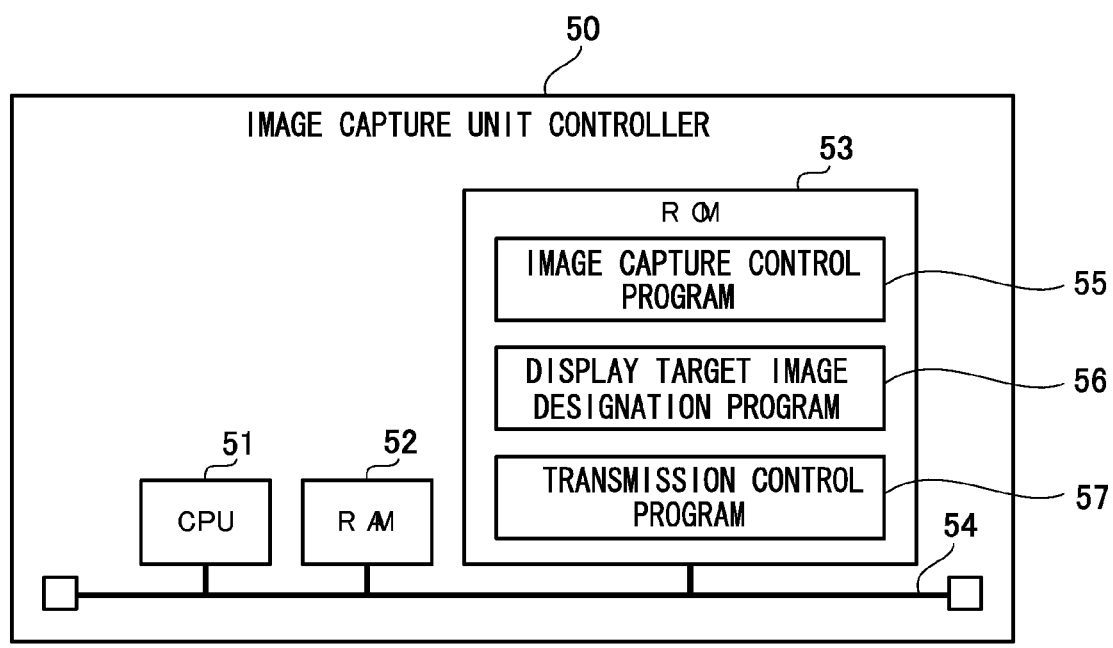
FIG. 6 is a block diagram illustrating a detailed configuration of an image capture unit controller according to an exemplary embodiment of the present invention.

The image capture unit controller 50 is configured including a microcomputer that is connected to the gate line driver 41, the signal processor 42, the image memory 43, and the communication section 44, and that controls the overall operation thereof. FIG. 6 is a block diagram illustrating a detailed configuration of the image capture unit controller 50. The image capture unit controller 50 is configured including a Central Processing Unit (CPU) 51, Random Access Memory (RAM) 52, Read Only Memory (ROM) 53, and a bus 54 that connects these sections to each other. An image capture control program 55, a display target image designation program 56, and a transmission control program 57, described below, are stored in the ROM 53.

Figure 7:
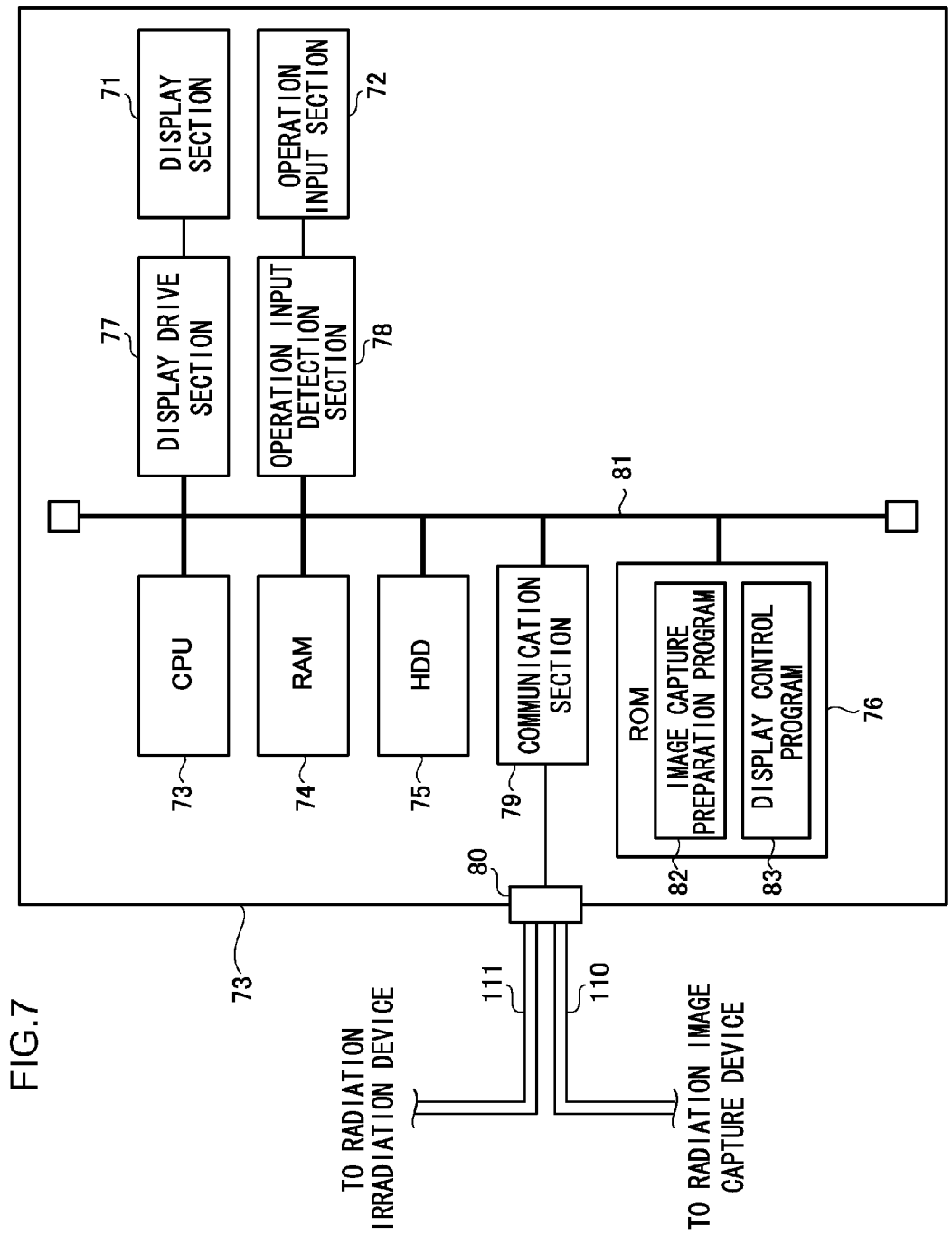
FIG. 7 is a block diagram illustrating a detailed configuration of a console according to an exemplary embodiment of the present invention.

FIG. 7 is a block diagram illustrating a detailed configuration of the console 70 configuring the radiation image capture system 100 according to an exemplary embodiment of the present invention. The console 70 is configured as a computer. The console 70 includes a display section 71 that displays an operation menu, captured radiation images, and the like, and an operation input section 72 configured including plural keys through which various data and operation instructions can be input. The operation input section 72 may, for example, include a keyboard function, and may be touch panel mode integrated to the display section 71. The operation input section 72 may be configured including a camera, and may be configured to input operation instructions by recognizing gestures of an operator using the camera. The console 70 includes a CPU 73, RAM 74, a Hard Disk Drive (HDD) 75, and ROM 76. The console 70 includes a display drive section 77 that controls display of various data on the display section 71 and an operation input detection section 78 that detects operation input to the operation input section 72. The console 70 includes a communication section 79 that controls communication between the radiation image capture device 10 and the radiation irradiation device 90. The communication section 79 is connected to the radiation image capture device 10 through a communication terminal 80 and a communication cable 110, and is connected to the radiation irradiation device 90 through the communication terminal 80 and the communication cable 111. The CPU 73, the RAM 74, the ROM 76, the HDD 75, the display drive section 77, the operation input detection section 78, and the communication section 79 are connected to each other through a bus 81. An image capture preparation program 82 and a display control program 83, described below, are stored in the ROM 76.

Figure 8:
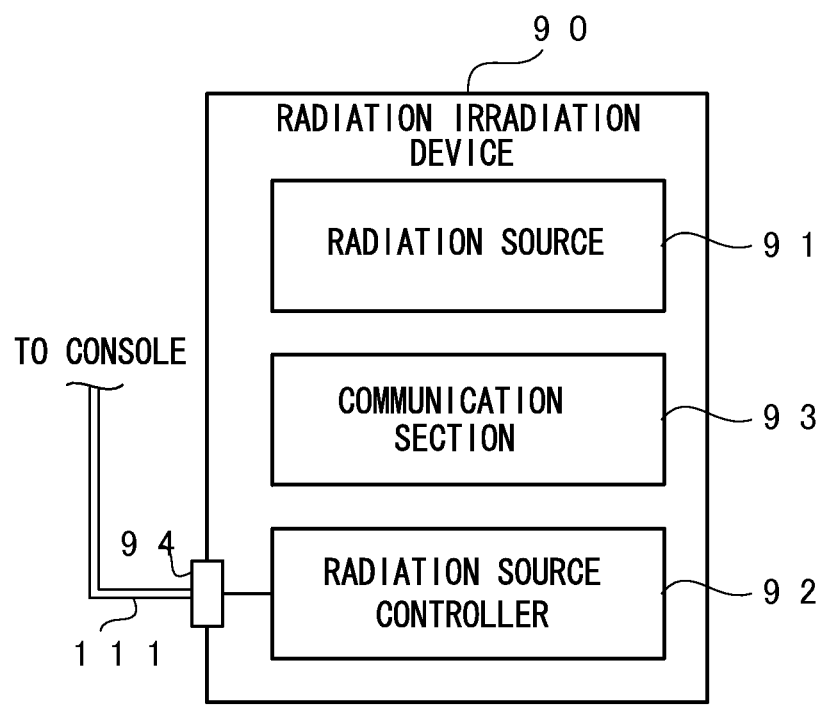
FIG. 8 is a block diagram illustrating a detailed configuration of a radiation irradiation device according to an exemplary embodiment of the present invention.

FIG. 8 is a block diagram illustrating a detailed configuration of a radiation irradiation device 90 that configures the radiation image capture system 100 according to an exemplary embodiment of the present invention. The radiation irradiation device 90 includes a radiation source 91 that generates X-rays, a communication section 92 that controls communication with the console 70 through the communication cable 111, and a radiation source controller 93 that controls the radiation source 91 based on X-ray irradiation conditions received from the console 70 through the communication cable 111. The communication section 92 is connected to the console 70 through a communication terminal 94 and the communication cable 111. The radiation source controller 93 is configured including a microcomputer, and stores X-ray irradiation conditions and the like transmitted from the console 70. The X-ray irradiation conditions transmitted from the console 70 include data such as tube voltage, tube current and irradiation time. The radiation irradiation device 90 may include an operation input section for a user to directly manually set the radiation irradiation device 90 with the X-ray irradiation conditions such as the tube voltage, the tube current and the irradiation time, and may include a display section for displaying set X-ray conditions and the like. The radiation irradiation device 90 transmits data indicating manually setting was made, the manual setting value, and the current status (standby state, preparation state, during exposure, exposure ended) to the console 70

Image Capture Preparation Processing

Figure 9:
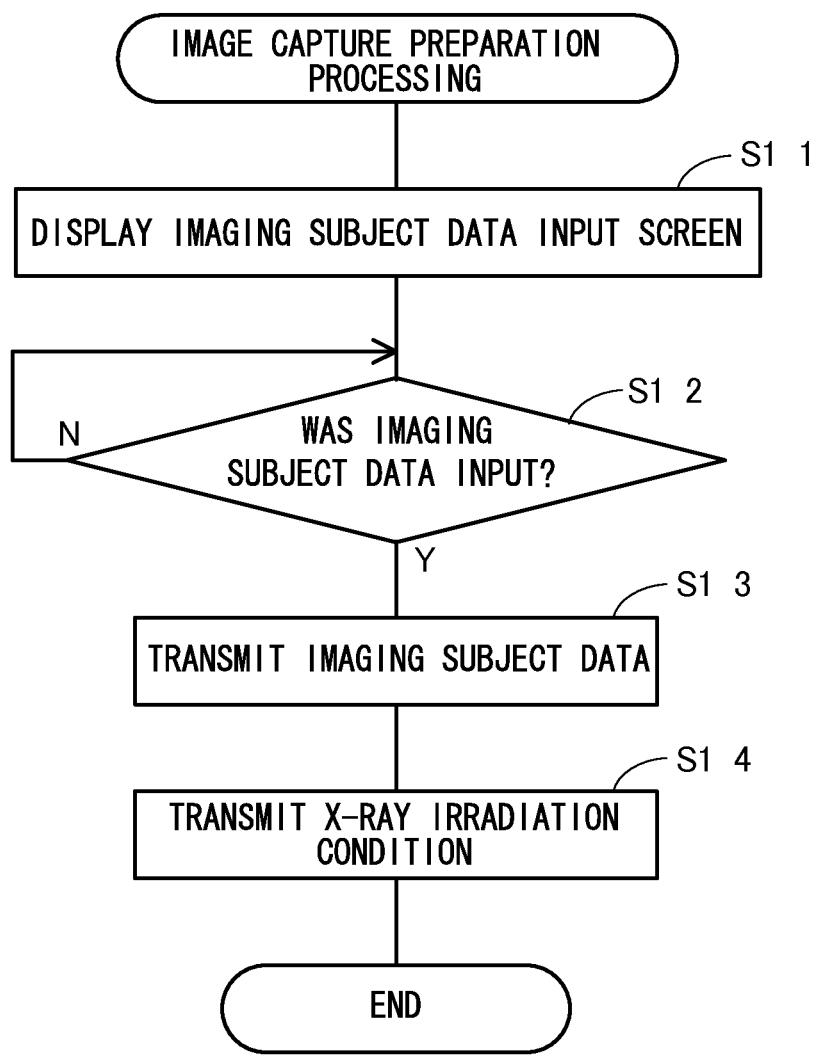
FIG. 9 is a flowchart illustrating a flow of image capture preparation processing implemented by executing an image capture preparation program according an exemplary embodiment of the present invention.

FIG. 9 is a flowchart that illustrates a flow of image capture preparation processing implemented by the CPU 73 of the console 70 executing the image capture preparation program 82 stored on the ROM 76. The image capture preparation program 82 is, for example, started in cases in which a user has instructed start of image capture preparation through the operation input section 72.

At step S11, the CPU 73 controls the display drive section 77 to display an imaging subject data input screen on the display section 71. The imaging subject data input screen displays a message prompting input of the sex, the age, the height, the weight and the body thickness of the patient that is the imaging subject, the image capture target site, the posture during image capture, the X-ray irradiation conditions, and the like, and displays an input region for such information. At step S12, the CPU 73 awaits input for the imaging subject data. Affirmative determination is made at step S12 when input has been made through the operation input section 72 of the imaging subject data, and processing transitions to step S13.

At step S13, the CPU 73 transmits input imaging subject data to the radiation image capture device 10 through the communication section 79. At step S14, the CPU 73 transmits the X-ray conditions input at step S12 to the radiation irradiation device 90 through the communication section 79. The radiation source controller 93 of the radiation irradiation device 90 performs X-ray irradiation preparation required to perform X-ray irradiation with the X-ray conditions received through the communication section 92.

Then, when an operation switch to execute X-ray irradiation (not illustrated in the drawings) has been operated, the radiation source 91 of the radiation irradiation device 90 emits X-rays at a tube voltage, tube current, and irradiation duration corresponding to the X-ray irradiation conditions received from the console 70. The X-rays emitted from the radiation irradiation device 90 are irradiated onto the radiation image capture device 10 through the imaging subject O.

Image Capture Control Processing

Figure 10:
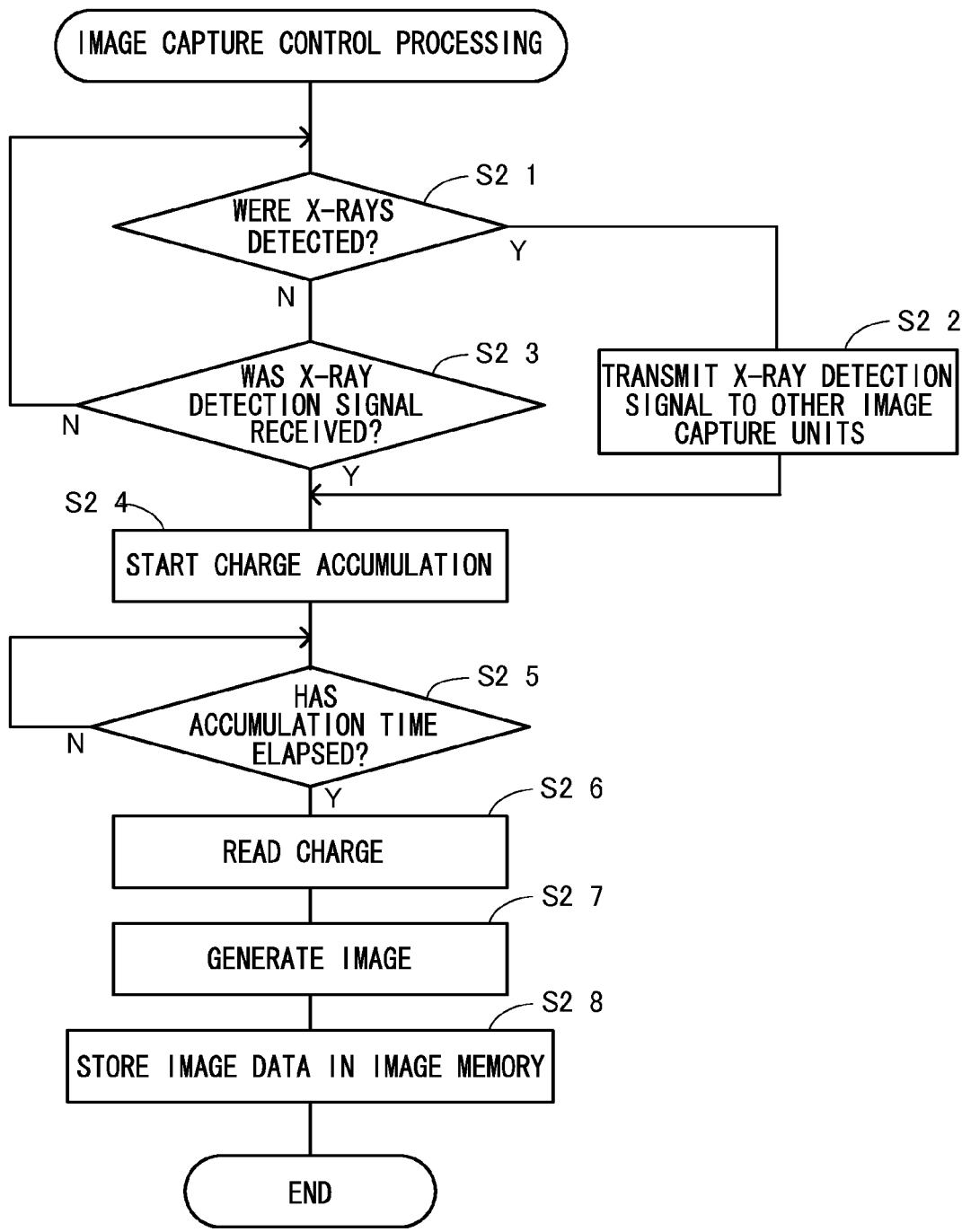
FIG. 10 is a flowchart illustrating a flow of image capture control processing implemented by executing an image capture control program according to an exemplary embodiment of the present invention.

FIG. 10 is a flowchart illustrating a flow of image capture processing implemented by the CPU 51 configuring the image capture unit controller 50 of each of the image capture units 11A, 11B, 11C executing the image capture control program 55 stored in the ROM 53. The image capture control program 55 is started, for example at step S15 of the above image capture preparation processing, by receiving a control signal instructing X-ray irradiation start transmitted from the console 70.

At step S21, the CPU 51 configuring the image capture unit controller 50 in each of the image capture units 11 (the image capture units 11A, 11B, 11C) respectively determines whether or not X-ray irradiation from the radiation irradiation device 90 has been detected. Namely, the CPU 51 of each of the image capture units 11 determines that X-rays have been detected in cases in which the dose of X-rays represented by the amount of charges generated in the irradiation detection pixels 32 provided in its own corresponding radiation detection panel 20 has reached a specific threshold value.

In cases in which some of the image capture units 11A, 11B, 11C are employed to capture radiation images, normally X-rays are only irradiated onto those of the image capture units 11 employed for image capture, and X-rays are not irradiated onto the image capture units 11 not employed for image capture. Thus in cases in which some of the image capture units 11A, 11B, 11C are employed to capture radiation images, X-rays are detected only in the image capture units 11 employed for image capture. Processing transitions to step S22 in cases in which the CPU 51 of each of the image capture units 11 determines that X-rays have been detected at step S21, and processing transitions to step 23 in cases in which X-rays have not been detected.

At step S22, the CPU 51 of the image capture unit 11 that has detected X-rays transmits to the other image capture units 11 an X-ray detection signal indicating that X-rays have been detected, through the communication section 44 and the communication line 46, and processing transitions to step S24. At step S23, the image capture units 11 that have not detected X-rays await receipt of X-ray detection signals from the other image capture units 11. Processing transitions to step S24 when the image capture units 11 that have not detected X-rays have received an X-ray detection signal from another image capture unit 11, and processing returns to step S21 in cases in which an X-ray detection signal is not received from the other image capture units 11.

Due to the processing of steps S21 to S23, in cases in which X-rays have been detected by some of the image capture units 11, detection data indicating that X-rays have been detected in some of the image capture units 11 is shared with the other image capture units 11 that have not detected X-rays.

At step S24, the CPU 51 of each of the image capture units 11 transitions to image capture operation. Namely, the CPU 51 of each of the image capture units 11 supplies a control signal to its own corresponding gate line driver 41 to drive all the TFTs 34 of the image capture pixels 31 to an OFF state. The charges generated in the sensors 310 of each of the image capture pixels 31 accompanying irradiation with X-rays are thereby accumulated in the sensors 310. Thus at the present step S24 charge accumulation processing is performed in all the image capture units 11, including any image capture units 11 that did not detect X-rays at step S21 (were not used for image capture). However, charges generated in the sensors 320 of the irradiation detection pixels 32 accompanying X-ray irradiation are supplied to the signal processor 42 through the signal lines 36 without being accumulated.

At step S25, the CPU 51 of each of the image capture units 11 determines whether or not a specific accumulation period has elapsed since the start of charge accumulation at step S24. Processing transitions to step S26 in cases in which the CPU 51 of each of the image capture units 11 determines that the specific accumulation period has elapsed.

At step S26, the CPU 51 of each of the image capture units 11 supplies a control signal to the gate line driver 41 and reads the charges accumulated in the sensors 310 of the image capture pixels 31 of each of the radiation detection panels 20. The gate line driver 41 of each of the image capture units 11 that has received the control signal from the CPU 51 outputs an ON signal in sequence to each of the gate lines 35, and switches the TFTs 34 connected to each of the gate lines 35 ON in sequence one line at a time. The charges accumulated in the sensors 310 of each of the image capture pixels 31 are thereby read as electrical signals through each of the signal lines 36, and transmitted to the signal processor 42. The signal processor 42 of each of the image capture units 11 generates a digital signal representing the pixel values of each of the image capture pixels 31 (pixel value of each of the image capture pixels 31) based on the electrical signals supplied through each of the signal lines 36, and supplies the generated digital signal to the CPU 51. At step S26, processing is performed to read charges from all the image capture units 11, including any image capture units 11 that did not detect X-rays at step S21 (were not used for image capture).

At step S27, the CPU 51 of each of the image capture units 11 generates, as image data, data in which a digital signal supplied from the signal processor 42 (pixel value of each of the image capture pixels 31) is associated with position data of the image capture pixels 31. At step S27, image data generation processing is performed in all the image capture units 11, including any image capture units 11 that did not detect X-rays at step S21 (were not used for image capture).

At step S28, the CPU 51 of each of the image capture units 11 stores the generated image data in its own corresponding image memory 43 and ends the current routine. In the processing of step S28, image data storage processing is performed in all the image capture units 11, including any image capture units 11 that did not detect X-rays at step S21 (were not used for image capture).

As described above, in the radiation image capture device 10, the charge accumulation processing, the charge reading processing, the image data generation processing, and the image data storage processing are implemented at the same timing in all of the image capture units, even in cases in which only some of the image capture units 11A, 11B, 11C are employed for image capture. Namely, for single time of X-ray irradiation, when radiation irradiation start has been detected in any of the image capture units 11, then radiation image generation is performed in each of the image capture units 11A, 11B, 11C even if X-rays have not been detected itself, and image data is stored in the image memory 43. For example, in cases in which radiation image capture is performed employing only the image capture unit 11B, processing for generating radiation images is implemented also in the image capture units 11A and 11C, and the generated radiation images are stored in the image memory 43 of each of the image capture units 11.

Display Target Image Designation Processing

In the radiation image capture device 10, the image to be displayed on the display section 71 of the console 70 (referred to below as the display target image) is designated from out of the radiation images generated in the image capture units 11A, 11B, 11C by the above image capture control processing. For example, the radiation image capture device 10 designates as the display target image the image estimated to contain the imaging subject image from out of the radiation images generated in the respective image capture units 11A, 11B, 11C. For example, in cases in which only the image generated in the image capture unit 11B is estimated to include the imaging subject image, the radiation image capture device 10 designates only the image generated by the image capture unit 11B as the display target image, and transmits the designated image to the console 70.

Figure 11:
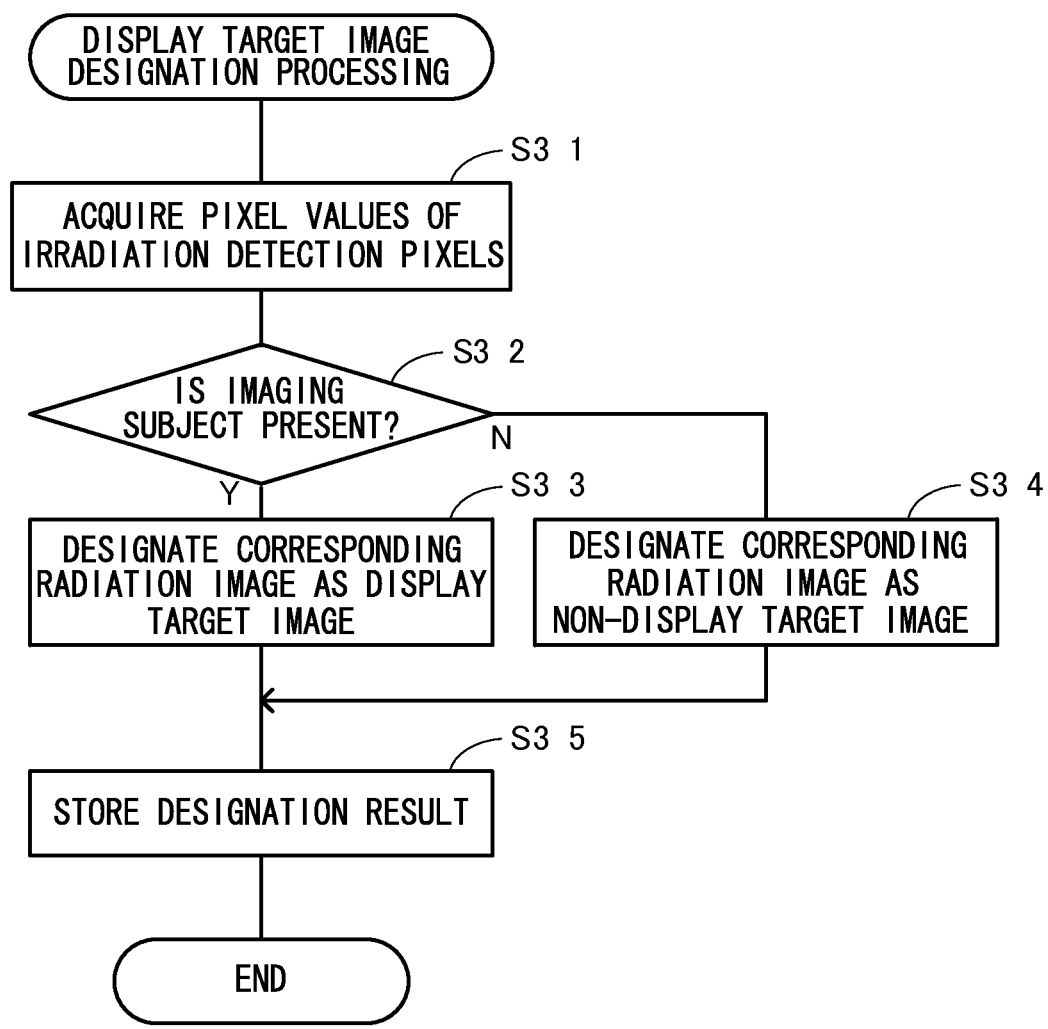
FIG. 11 is a flowchart illustrating a flow of display target image designation processing implemented by executing a display target image designation program according to an exemplary embodiment of the present invention.

FIG. 11 is a flow chart illustrating a flow of display target image designation processing implemented by the CPU 51 of the image capture unit controller 50 of each of the image capture units 11A, 11B, 11C executing the display target image designation program 56 stored in the ROM 53. The display target image designation program 56 is started, for example, at the same time as the above image capture control processing (see FIG. 10). Namely, the display target image designation program 56 and the image capture control program 55 are executed in parallel to each other. The CPU 51 of each of the image capture units 11 executing the display target image designation program 56 is an example of a designation section of the present invention.

At step S31, the CPU 51 of each of the image capture units 11 acquires pixel values from each of the irradiation detection pixels 32 from the signal processor 42. Electrical signals from charges generated in each of the sensors 320 of the irradiation detection pixels 32 of each of the image capture units 11 are supplied to the signal processor 42 through each of the signal lines 36. The signal processor 42 of each of the image capture units 11 generates a digital signal representing the pixel values of each of the irradiation detection pixels 32 based on the electrical signals supplied through each of the signal lines 36, and supplies the digital signals to the CPU 51. Step S31 is executed prior to step S26 (charge reading) in the above image capture control processing (see FIG. 10).

Step S31 is processing for detecting the presence or absence of X-ray irradiation onto the radiation detection panels 20. In the present exemplary embodiment, the irradiation detection pixels 32 are employed for detecting the presence or absence of X-ray irradiation onto the radiation detection panels 20, however, as described above, the irradiation detection pixels 32 may be substituted with another means, enabling the presence or absence of X-ray irradiation onto the radiation detection panels 20 to be detected by the substituted means.

For example, instead of the irradiation detection pixels 32, in cases (above case (1)) in which pixels freely selected from out of the image capture pixels 31 function as pixels (shorted pixels) that exclusively detect the presence or absence of irradiated X-rays, at step S31, the CPU 51 of each of the image capture units 11 detects the presence or absence of X-ray irradiation onto the radiation detection panels 20 by acquiring pixel values of the pixels (shorted pixels) that exclusively detect the presence or absence of irradiated X-rays from the signal processor 42.

In cases in which a bias current detection means is provided to detect a bias current flowing in each of the sensors 310 and a method is adopted (above case (2)) in which the presence or absence of X-ray irradiation is detected based on the magnitude of the bias current detected by the bias current detection means, the presence or absence of X-ray irradiation onto the radiation detection panels 20 is detected by the CPU 51 of each of the image capture units 11 acquiring data representing the magnitude of the bias current from the bias current detection means at step S31.

Moreover, in cases in which additional TFTs are provided to selected pixels within the image capture pixels 31 and a method is used in which the presence or absence of X-ray irradiation is detected based on leak current of the additionally provided TFTs (above case (3)), the presence or absence of X-ray irradiation onto the radiation detection panels 20 is detected by the CPU 51 of each of the image capture units 11 acquiring data representing the magnitude of the leak current from the additional TFTs at step S31.

Moreover, in cases in which a method is adopted in which the magnitude of current flowing from the gate line driver 41 to each of the gate lines 35 is detected and a method of detecting the presence or absence of X-ray irradiation based on the magnitude of the detected current (above case (4)) is adopted, the presence or absence of X-ray irradiation onto the radiation detection panels 20 is detected by the CPU 51 of each of the image capture units 11 acquiring data representing the magnitude of the current flowing in each of the gate lines 35 at step S31.

Moreover, in cases in which sensors that detect the presence or absence of radiation irradiation are provided in a different layer to the layer in which the image capture pixels 31 are provided in the radiation detection panels 20, or sensors for detecting the presence or absence of radiation irradiation are provided as a separate body to the radiation detection panels 20 (above case (5)), the presence or absence of X-ray irradiation onto the radiation detection panels 20 is detected by the CPU 51 of each of the image capture units 11 based on the output values of the sensors provided in a separate layer to the layer in which the image capture pixels 31 are provided, or the output values (pixel values) of the sensors provided as a separate body to the radiation detection panels 20.

At step S32, the CPU 51 of each of the image capture units 11 determines whether or not the imaging subject is placed over its own corresponding radiation detection panel 20 based on each of the pixel values of the irradiation detection pixels 32 acquired at step S31. For example, the CPU 51 of each of the image capture units 11 determines that the imaging subject is placed over its own corresponding radiation detection panel 20 in cases in which the proportion of pixels outputting pixel value exceeding a specific threshold value, out of the plural irradiation detection pixels 32, is determined to be a specific value or greater.

For example, in cases in which radiation image capture is performed using only the image capture unit 11B, normally X-rays are not irradiated onto the image capture units 11A and 11C not used for image capture. In such cases, a significant difference arises between the pixel values of the irradiation detection pixels 32 of the image capture unit 11B use for image capture and the pixel values of the irradiation detection pixels 32 of the image capture units 11A and 11C not used for image capture, enabling determination of the presence or absence of the imaging subject to be made by the determination described above. The X-rays irradiated onto the imaging subject placed over the image capture unit 11B are also scattered, and sometimes the X-rays are also incident to the image capture units 11A and 11C not used for image capture. In such cases there is a concern that detection of the scattered radiation in the image capture units 11A and 11C may result in false determination that the imaging subject is disposed above the radiation detection panels 20A and 20C. It is consequently preferable that the threshold value for the pixel values is set at appropriately in order to prevent such false determination. The dose of the scattered radiation is extremely small, enabling the effects of scattered radiation to be excluded by setting the threshold value for the pixel values appropriately.

Moreover, the plural irradiation detection pixels 32 are uniformly provided in the respective radiation detection panels 20 of each of the image capture units 11, enabling easy radiation image generation based on each of the irradiation detection pixels 32. The CPU 51 of each of the image capture units 11 may accordingly determine whether or not the imaging subject is placed its own corresponding radiation detection panel 20 by easy analysis of the radiation image generated based on the pixel values of each of the irradiation detection pixels 32. Continuous regions where the X-rays irradiation amount is comparatively small above the radiation detection panels 20 have a high probability of being regions where the X-rays have passed through the imaging subject. Based on the pixel value of the irradiation detection pixels 32, the CPU 51 of each of the image capture units 11 may, as an example, determine that the imaging subject is placed above a radiation detection panel 20 in cases in which a region where the X-ray dose is comparatively large, and a continuous region where the X-ray dose is comparatively small, are detected. In order to eliminate the influence from scattered radiation in such cases, preferably image patterns arising from scattered radiation are pre-determined, such that a pattern of an image due to scattered radiation can be clearly distinguished from a subject image.

In cases in which a substitute means is employed for the irradiation detection pixels 32 described above, determination is made as to whether or not the imaging subject is placed above its own corresponding radiation detection panels 20 based on the data acquired by the substitute means.

In the CPU 51 of each of the image capture units 11, processing transitions to step S33 in cases in which, as a result of the determination processing at step S32, determination is made that the imaging subject is placed above its own corresponding radiation detection panel 20. At step S33, the CPU 51 of each of the image capture units 11 designates as the display target image the radiation image (the radiation image based on the image capture pixels 31) generated in that image capture unit 11 at step S27 of the above image capture control processing (see FIG. 10).

In the CPU 51 of each of the image capture units 11, processing transitions to step S34 in cases in which determination is made that the imaging subject is not placed above its own corresponding radiation detection panel 20 as a result of the determination processing at step S32. At step S34, the CPU 51 of each of the image capture units 11 designates the radiation image generated in that image capture unit 11 at step S27 of image capture control processing (see FIG. 10) as a non-display target image.

At step S35 the CPU 51 of each of the image capture units 11 stores the designation result from step S33 or step S34 in the RAM 52 associated with the radiation image.

As described above, in each of the image capture units 11A, 11B, 11C, in parallel to generating the radiation images based on the pixel values of each of the image capture pixels 31, determination is made of the presence or absence of the subject image in the radiation images based on the pixel value of each of the irradiation detection pixels 32. Based on the results of the determination of the presence or absence of the subject image, the radiation images generated in each of the image capture units 11A, 11B, 11C are designated as either a display target image or a non-display target image. Thus for a single time of radiation irradiation, the radiation image capture device 10 performs processing to generate the radiation image in each of the image capture units 11, and performs processing to designate the display target image from out of the radiation images generated in each of the image capture units 11, in parallel to each other.

In the present exemplary embodiment, the processing to determine whether or not the imaging subject is placed above its own corresponding radiation detection panel 20 is performed by the radiation image capture device 10 based on the pixel values of each of the irradiation detection pixels 32 (step 32), however this processing may be performed by the console 70. In such cases, each of the image capture units 11 of the radiation image capture device 10 transmit to the console 70 data associating position data of the irradiation detection pixels 32 with pixel values of the irradiation detection pixels 32. The console 70 determines whether or not the imaging subject is placed above one of the radiation detection panels 20 based on the data, and transmits the determination result to the radiation image capture device 10. The radiation image capture device 10 designates the display target image and the non-display target images based on the determination result received from the console 70.

Transmission Control Processing

The radiation image capture device 10 transmits only the display target image designated by the display target image designation processing (see FIG. 11) to the console 70. Sometimes the display target image designation processing according to the present exemplary embodiment designates plural radiation images generated by the respective plural image capture units 11 as display target images. For example, in cases in which it is determined that the subject image is included in respective radiation images generated by both the image capture unit 11A and the image capture unit 11B, these two radiation images are designated as display target images. In such cases in which plural radiation images are designated as the display target image, the radiation image capture device 10 derives a transmission sequence for the respective plural radiation images designated as display target images, and transmits each of the display target images to the console 70 according to the derived transmission sequence.

Figure 12:
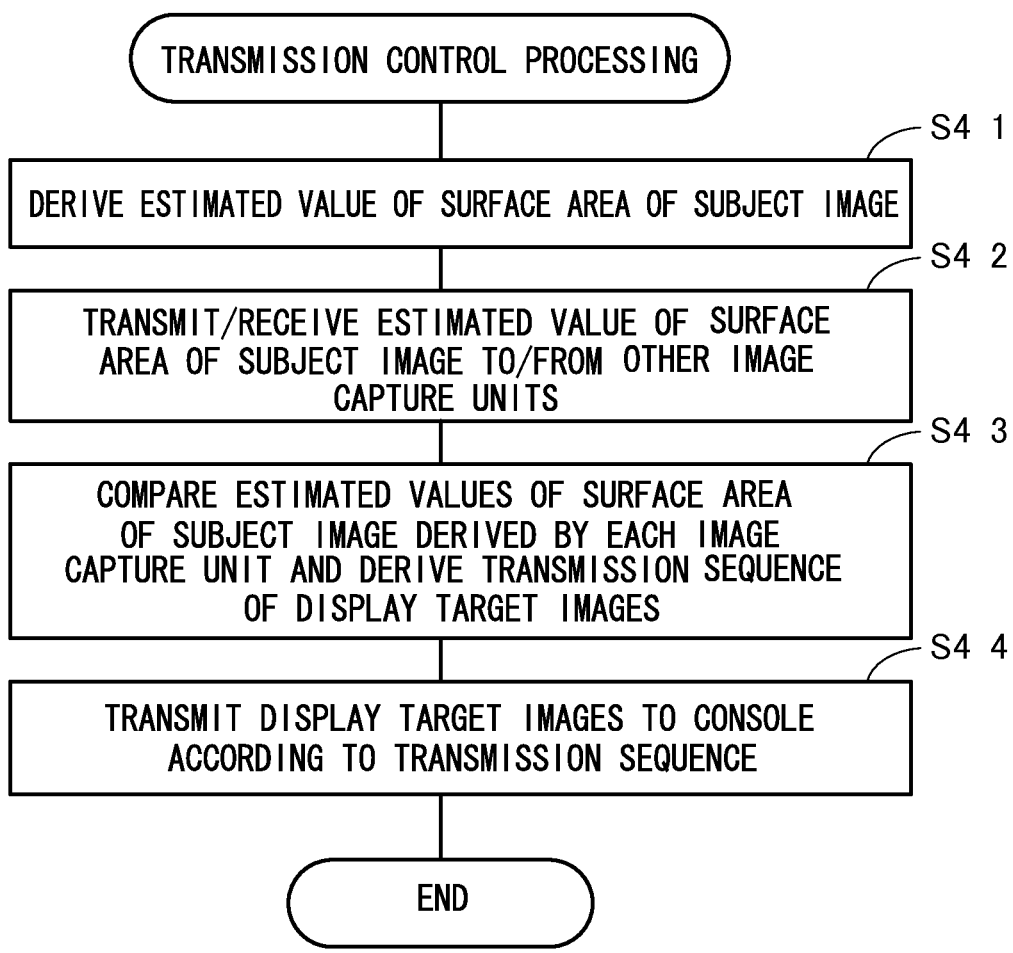
FIG. 12 is a flowchart illustrating a flow of transmission control processing implemented by executing a transmission control program according to an exemplary embodiment of the present invention.

FIG. 12 is a flowchart illustrating a flow of transmission control processing implemented by the CPU 51 configuring the image capture unit controller 50 of each of the image capture units 11A, 11B, 11C executing the transmission control program 57 stored in the ROM 53. The transmission control program 57 is, for example, executed by the CPU 51 of each of the image capture units 11 after completing the image capture control processing (see FIG. 10) and the display target image designation processing (see FIG. 11). The CPU 51 of each of the image capture units 11 that execute the transmission control program 57 are examples of a transmission section of the present invention.

At step S41, the CPU 51 of each of the image capture units 11 that have generated the display target images derives an estimated value of the surface area of the subject image included in their own corresponding radiation images (display target images) based on the pixel values of the irradiation detection pixels 32 obtained at step S31 of the display target image designation processing (see FIG. 11). The continuous regions where the X-ray irradiation dose is relatively small on the radiation detection panels 20 are highly likely to be regions where the X-rays have been irradiated after passing through the imaging subject. The CPU 51 of each of the image capture units 11 that have generated the display target images, for example, may identify the continuous regions where the X-ray irradiation dose is relatively small based on the pixel values of the irradiation detection pixels 32, and derive the surface area of the continuous regions as the estimated value of the surface area of the subject image.

At step S42, the CPU 51 of each of the image capture units 11 that generated the display target images transmit the estimated values of surface area of the subject image derived in the previous step S41 to the other image capture units 11 through the communication line 46, and also receive estimated values of surface area of the subject image derived by the other image capture units 11 from the other image capture units 11 through the communication line 46. The estimated values of surface area of the subject image derived in each of the image capture units 11 are thereby shared with the other image capture units 11.

At step S43, the CPU 51 of each of the image capture units 11 that generated the display target images derives a transmission sequence of their own corresponding radiation image (display target image) by comparing the estimated value of surface area of the subject image derived by that image capture unit 11 against the estimated value of surface area of the subject image derived by the other image capture units 11. Namely, the CPU 51 of each of the image capture units 11 that generated the display target images derives transmission sequences for the display target images such that display target images with larger estimated values of surface area of the subject image included in the display target image are transmitted to the console 70 first.

At step S44, the CPU 51 of each of the image capture units 11 that generated the display target images transmit the display target image generated by themselves to the console 70 through the communication cable 110 according to the transmission sequence derived at step S43. Each of the display target images to be transmitted may be appended with identification data indicating that the respective image is a display target image and representing the transmission sequence of the respective image. The images other than the display target images (the non-display target images) are not transmitted to the console 70, and are retained in the image memory 43. Each of the display target images transmitted to the console 70 is stored in the RAM 74 or the HDD 75 of the console 70.

Explanation follows regarding a specific example of flow of the above transmission control processing. For example, in a case in which a radiation image $I_A$ generated by the image capture unit 11A and a radiation image $I_B$ generated by the image capture unit 11B are designated as display target images, consider a case in which an estimated value of the surface area of the subject image included in the radiation image $I_B$ is larger than the estimated value of surface area of the subject image included in the radiation image $I_A$. In such a case, the CPU 51 of the image capture unit 11B derives "1" as the transmission sequence of the radiation image $I_B$ generated by the image capture unit 11B. The CPU 51 of the image capture unit 11A derives "2" as the transmission sequence of the radiation image $I_A$ generated by the image capture unit 11A.

The CPU 51 of the image capture unit 11B that generated the radiation image $I_B$, this being the display target image to be transmitted first, transmits the radiation image $I_B$ to the console 70. The CPU 51 of the image capture unit 11B then notifies the other image capture units 11A and 11C that transmission of the radiation image $I_B$ has been completed. From out of the image capture units 11A, 11C that received notification of transmission completion of the radiation image $I_B$, the CPU 51 of the image capture unit 11A that generated the radiation image $I_A$, this being the display target image to be transmitted second, then transmits the radiation image $I_A$ to the console 70. The radiation image $I_C$ generated by the image capture unit 11C is not designated as a display target image, and so the radiation image $I_C$ is not transmitted at this stage to the console 70, and is retained in the image memory 43.

As described above, the radiation image capture device 10 according to the present exemplary embodiment derives the transmission sequence to the console 70 for plural display target images generated by plural image capture units 11 based on the estimated values of surface area of the subject images included in the display target images. More specifically, the transmission sequence of the display target images is derived such that the display target image with the larger estimated values of surface area of subject image included in the display target image are transmitted to the console 70 first. The radiation image capture device 10 transmits the plural display target images in sequence to the console 70 according to the derived sequence. The radiation image capture device 10 does not transmit images other than the display target images (non-display target images) to the console 70, and retains these in the image memory 43.

The transmission control processing according to the present exemplary embodiment enables the more important images to be transmitted to the console 70 first. The images other than the display target images (non-display target images) are not transmitted to the console 70, enabling the volume of data transmitted to the console 70 to be suppressed. This thereby enables the data transmission time to be shortened in comparison to cases in which all the radiation images generated by each of the image capture units 11 are transmitted to the console 70.

In the present exemplary embodiment, processing to derive estimated values of surface area of the subject image based on the pixel values of the irradiation detection pixels 32 (step S41), sharing the derived estimated value of surface area of the subject image with each of the image capture units 11 (step S42), and processing to derive the transmission sequence of the radiation images (the display target images) (step S43), are performed by the radiation image capture device 10, however each of these types of processing may be performed by the console 70.

In such cases, each of the image capture units 11 of the radiation image capture device 10 transmits data associating position data of the irradiation detection pixels 32 with the pixel values of the irradiation detection pixels 32 to the console 70. The console 70 then derives the estimated value of surface area of the subject image based on this data, and derives the transmission sequence of radiation images based on the derived estimated values. The console 70 transmits data representing the derived transmission sequence of the radiation images to each of the image capture units 11. Each of the image capture units 11 then transmits the display target image to the console 70 according to the transmission sequence derived in the console 70.

Display Control Processing

Figure 13:
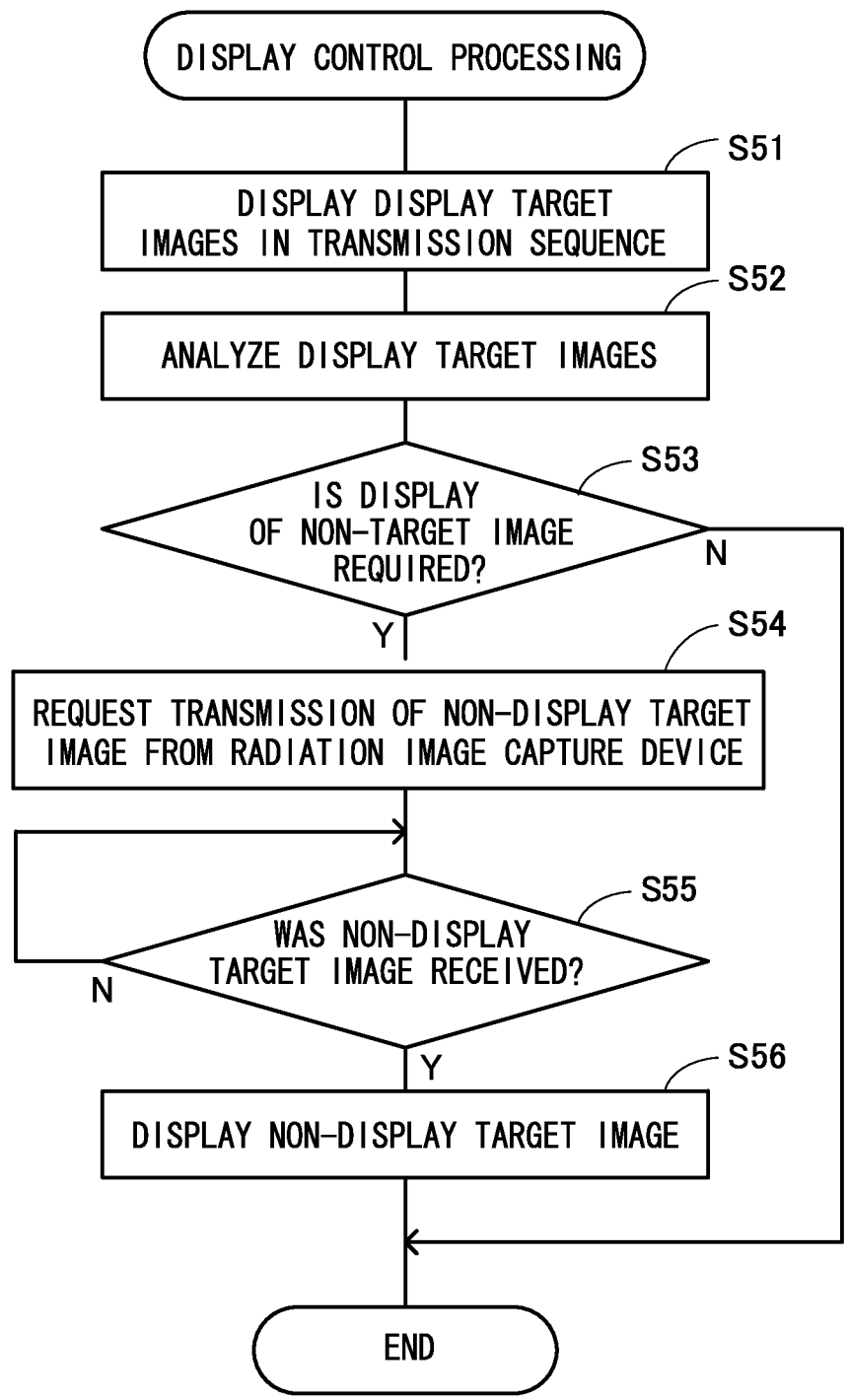
FIG. 13 is a flowchart illustrating a flow of display control processing implemented by executing a display control program according to an exemplary embodiment of the present invention.

FIG. 13 is a flowchart illustrating a flow of display control processing implemented by the CPU 73 of the console 70 executing the display control program 83 stored in the ROM 76. The display control program 83 is, for example, started when the display target image transmitted from the radiation image capture device 10 is received by the console 70. The CPU 73 of the console 70 executing the display control program 83 is an example of a display controller of the present invention.

At step S51, the CPU 73 of the console 70 controls the display drive section 77, and displays on the display section 71 the display target images transmitted from the radiation image capture device 10 in turn for each of the image capture units 11, in the sequence they were received. Namely, the display target images are displayed on the display section 71 in the transmission sequence set in the radiation image capture device 10. The CPU 73 of the console 70 may display each of the display target images on the display section 71 in sequence according to the transmission sequence represented by identification data appended to each of the display target images.

At step S52, the CPU 73 of the console 70 analyzes the display target image already displayed on the display section 71, and, at step S53, determines whether or not there is a need to display on the display section 71 any image other than the display target images (a non-display target image).

As described above, the radiation image capture device 10 determines the presence or absence of the subject image based on the pixel values of the irradiation detection pixels 32 provided to each of the radiation detection panels 20 of each of the image capture units 11, and designates images determined to include the subject image as display target images. However, the number of pixels of the irradiation detection pixels 32 provided in each of the radiation detection panels 20 is small compared to the number of pixels of the image capture pixels 31, and sometimes it is not possible to make appropriate determination of the presence or absence of the subject image. Namely, in the radiation image capture device 10, it is conceivable that there are cases in which the subject image is not included in an image designated as being a display target image, and that there are cases in which a subject image is actually included in a non-display target image. The CPU 73 of the console 70 therefore performs image analysis on the display target image transmitted from the radiation image capture device 10, and determines whether or not the subject image is appropriately included in the display target image. The display target image is a high precision image generated with the image capture pixels 31, thereby enabling higher precision analysis to be performed than when employing the irradiation detection pixels 32.

Figure 14:
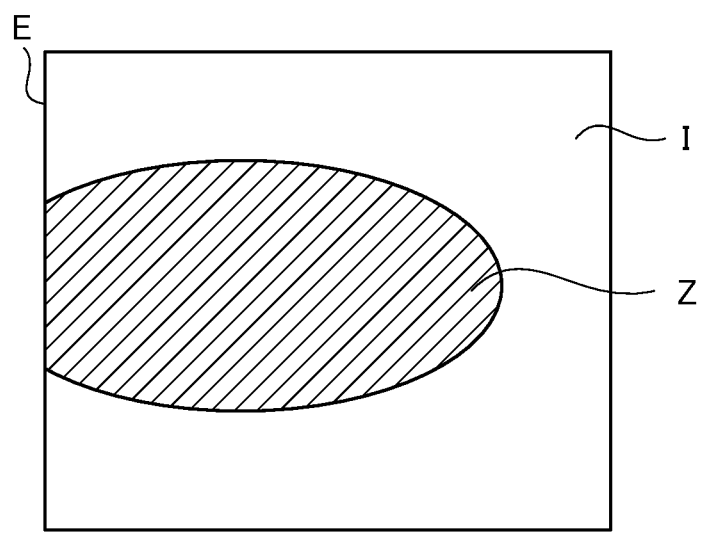
FIG. 14 is a diagram illustrating an example of a radiation image generated by a radiation image capture device according to an exemplary embodiment of the present invention.

The CPU 73 of the console 70 may, for example, perform shape recognition based on the display target images transmitted from the radiation image capture device 10, and determine that there is a need to display an image other than the display target image (a non-display target image) on the display section 71 in cases in which all of the estimated shape of the subject image is not included in the display target image. The CPU 73 of the console 70 may also, for example, determine that there is a need to display on the display section 71 an image other than the display target image (a non-display target image) in cases in which a pattern of a histogram of the pixel values in the display target image transmitted from the radiation image capture device 10 does not satisfy a specific condition. The CPU 73 of the console 70 may also, for example, determine that there is a need to display on the display section 71 a non-display target image in cases in which a subject image Z recognized in a display target image I transmitted from the radiation image capture device 10 contacts an image end portion E, and the subject image Z is determined to also be included in a non-display target image that has not been transmitted to the radiation image capture device 10, as illustrated in FIG. 14.

The CPU 73 of the console 70 transitions processing to step S54 in cases in which it was determined at step S53 that display of an image other than the display target image (a non-display target image) on the display section 71 is required, and ends the present routine in cases in which it is determined not to be required.

At step S54, the CPU 73 of the console 70 requests transmission of an image other than the display target image (a non-display target image) from the radiation image capture device 10 by generating data indicating that display of an image other than the display target image (a non-display target image) is required on the display section 71, and transmitting this data to the radiation image capture device 10. For example, in cases in which the subject image is not recognized in the display target images transmitted from the radiation image capture device 10, the CPU 73 of the console 70 may request transmission of all of the non-display target images retained the image memories 43 of the radiation image capture device 10. Moreover, in cases in which the display target image transmitted from the radiation image capture device 10 is cut off as illustrated in FIG. 14, the CPU 73 of the console 70 may request transmission of the non-display target images estimated to include the missing portion of the subject image Z. On receipt of the non-display target image transmission request from the console 70, the radiation image capture device 10 may read in the transmission requested non-display target image from the image memories 43, and transmit these to the console 70.

At step S55, the CPU 73 of the console 70 awaits reception of non-display target images, and processing transitions to step S56 on receipt of a non-display target image.

At step S56, the CPU 73 of the console 70 controls the display drive section 77 such that the received non-display target images are displayed together with the display target images already being displayed on the display section 71. Namely, a combination image of the images designated as the display target images in the radiation image capture device 10, and the non-display target images subsequently transmitted in response to a request from the console 70, is displayed on the display section 71. The CPU 73 of the console 70 may, in cases in which the subject image is not recognizable in the display target image as a result of image analysis at step S52, control the display drive section 77 such that the non-display target image subsequently transmitted is displayed on the display section 71 in place of the display target image.

As described above, the console 70 displays the display target images received from the radiation image capture device 10 on the display section 71 in reception sequence, and displays the non-display target image read from the image memory 43 of the radiation image capture device 10 in response to a non-display target image display request on the display section 71, either together with the display target image or in place of the display target image.

Processing of the System Overall

Figure 15:
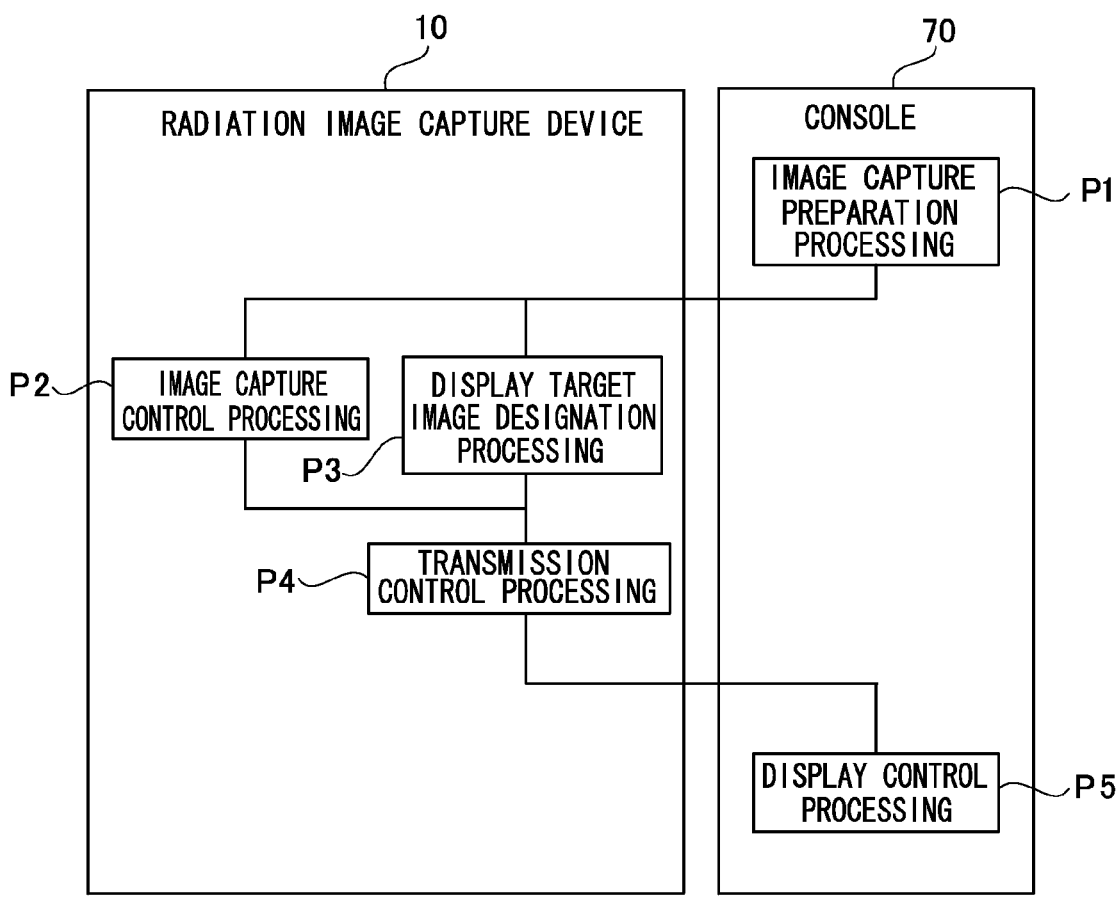
FIG. 15 is a diagram illustrating an overall flow of processing of a radiation image capture system according to an exemplary embodiment of the present invention.

FIG. 15 is a diagram illustrating a flow of processing of the system overall, including the display control processing (see FIG. 10), the display target image designation processing (see FIG. 11), and the transmission control processing (see FIG. 12) implemented in the radiation image capture device 10, and the image capture preparation processing (see FIG. 9) and the display control processing (see FIG. 13) implemented in the console 70.

First, the image capture preparation processing P1 illustrated in FIG. 9 is implemented in the console 70. In the image capture preparation processing P1, when a control signal representing an instruction for X-ray irradiation start has been transmitted from the console 70 to the radiation image capture device 10 (step S15 of FIG. 9), image capture control processing P2 and display target image designation processing P3 are implemented in parallel in the radiation image capture device 10.

In the image capture control processing P2, each of the image capture units 11 generate radiation images based on pixel values of the image capture pixels 31, and store each of the generated radiation images in the image memories 43. Each of the image capture units 11 shares detection data indicating that X-rays have been detected, and starts operation to generate a radiation image based on the detection data. Each of the image capture units 11 implement image capture processing such as charge accumulation and charge reading at the same timing as each other. For example, even in cases in which the imaging subject is placed above the image capture unit 11B and image capture is performed of a radiation image employing only the image capture unit 11B, the processing to generate a radiation image is implemented in not just the image capture unit 11B, but also in the image capture units 11A and 11C, and the generated radiation images are stored in the image memory 43 of the image capture unit itself.

In the display target image designation processing P3, each of the image capture units 11 determines whether or not the subject image is included in the radiation image generated by that image capture unit 11 based on the pixel values of the irradiation detection pixels 32. Each of the image capture units 11 designates the image as a display target image in cases in which determination is made that the subject image is included in the radiation image generated by that image capture unit 11, and designates the image as a non-display target image in cases in which determination is made that the subject image is not included in the radiation image generated itself by that image capture unit 11.

After completing image capture control processing P2 and display target image designation processing P3, a transmission control processing P4 is implemented in the radiation image capture device 10. In the transmission control processing P4, each of the image capture units 11 that has generated a display target image derives an estimated value of surface area of the subject image included in the display target image generated by that image capture unit 11, based on the pixel values of the irradiation detection pixels 32. Each of the image capture units 11 that has generated a display target image then derives a transmission sequence for display target images such that display target images with larger estimated value of surface area of the subject image included in the display target image are transmitted to the console 70 first, and then transmits the display target image sequentially to the console 70 according to the derived transmission sequence.

When the display target image transmitted from the radiation image capture device 10 has been received by the console 70, display control processing P5 is implemented in the console 70. In the display control processing P5, the display target images transmitted from the radiation image capture device 10 are displayed in reception sequence on the display section 71 of the console 70. Moreover, image analysis is performed of the display target image in the console 70, and determination is made as to whether or not there is a requirement to display a non-display target image on the display section 71 according to a determination result of whether or not the subject image is appropriately included in the display target image. In cases in which determination is made that there is a requirement to display a non-display target image on the display section 71, the console 70 requests the radiation image capture device 10 to transmit a non-display target image. On receipt of the non-display target image transmission request from the console 70, the radiation image capture device 10 reads the non-display target image according to the transmission request from the image memory 43, and transmits this image to the console 70. The console 70 then displays the non-display target image subsequently transmitted from the radiation image capture device 10 on the display section 71, either together with the display target image already being displayed on the display section 71, or in place of the display target image already being displayed on the display section 71.

As is clear from the above explanation, the radiation image capture device 10 according to the present exemplary embodiment of the present invention designates as display target images, and transmits to the console 70, only images estimated to include the subject image from out of the radiation images respectively generated by the plural image capture units 11A, 11B, 11C. In this manner, the volume of data transmitted to the console 70 can be suppressed by stringent selection of the images to be transmitted to the console 70, thereby enabling the data transmission time to be shortened in comparison to cases in which all the radiation images generated by each of the image capture units 11 are transmitted to the console 70. This thereby enables the waiting time until image display on the display section 71 of the console 70 to be shortened compared to previously.

The transmission sequence of the display target images is determined according to the estimated value of surface area of the imaging subject included in the display target images generated in each of the image capture units 11, enabling more important images to be displayed on the display section 71 of the console 70 as fast as possible.

The designation processing of the display target images and the derivation processing of the transmission sequence of the display target images that are implemented in the radiation image capture device 10 are performed employing the irradiation detection pixels 32, of which there are few compared to the image capture pixels 31, thus enabling each of the types of processing to be performed in a comparatively short time. This thereby limits the influence on the display waiting time caused by the designation processing of the display target images and the derivation processing of the transmission sequence of the display target images.

Moreover, in the console 70, the display target images are analyzed, and a transmission request for non-display target image is sent to the radiation image capture device 10 in cases in which it is determined that there is a need to display an image in the radiation image capture device 10 that has been designated as a non-display target image. The images of radiation images generated in each of the image capture units 11A, 11B, 11C are stored in the respective image memory 43 irrespective of whether the image is designated as a display target image or not, and the display target images are also retained in the image memories 43 after transmitting to the console 70. Thus in cases in which a transmission request for a non-display target image is received from the console 70, the radiation image capture device 10 is able to transmit non-display target images to the console 70 according to the transmission request. Thus in the radiation image capture system 100 configuration is made such that even in cases in which inappropriate designation of display target images has been made in the radiation image capture device 10, non-display target images can be displayed, enabling the risk of having to re-capture an image to be avoided.

Moreover, by each of the image capture units 11A, 11B, 11C sharing detection data representing detection of X-rays generated in whichever of the image capture units, image capture operation is started all at the same time, enabling radiation images to also be generated in the image capture units 11 that are not expected to be used. This thereby enables the subject image to be displayed even in cases in which the subject image is included in a radiation image generated by an image capture unit 11 not initially anticipated to be used. In this respect also, the radiation image capture device 10 according to present exemplary embodiment of the present invention is able to avoid the image recapture risk. Moreover, a user is also able to set the placement of the imaging subject with respect to the radiation image capture device 10 without consideration of the boundaries between each of the image capture units 11A, 11B, 11C.

As described above, the radiation image capture system 100 according to the present exemplary embodiment of the present invention is able to shorten the waiting time until image display is made on an external device compared to previously, while also avoiding an image recapture risk.

In the present exemplary embodiment, even after the display target image has been transmitted to the console 70, the corresponding radiation images (display target images or non-display target images) are respectively retained in each of the image memories 43 of the image capture units 11A, 11B, 11C, however there is no limitation to such embodiments. For example, configuration may be made such that after the display target images have been transmitted to the console 70 (after the display target images have been received by the console 70), only the non-display target image are retained in the image memories 43. Namely, configuration may be made such that after the display target images have been transmitted to the console 70 (after the display target images have been received by the console 70), the display target images are then erased from the image memories 43. This thereby enables a storage space to be secured in the image memories 43.

Moreover, from the viewpoint of securing the storage region in the image memory 43 of each of the image capture units 11, the images stored in the image memories 43 are preferably erased as appropriate. The method of erasing images from the image memory 43 may, for example, be performed at any of the following timings: (1) prior to performing the next X-ray irradiation; (2) after completing image capture for the same patient; (3) after a user operating the console 70 has confirmed an image for use in consultation; (4) an image generated by the radiation image capture device 10 has been transmitted to a picture archiving and communication system (PACS) connected to the radiation image capture system 100 through a network; (5) after consultation by a doctor has been completed and input has been completed, such as to an electronic patient record; or (6) after image erasure has been specified by a user operating the console 70 by operating the operation input section 72.

In any of these cases, an instruction is transmitted from the console 70 to the radiation image capture device 10 to erase images. The radiation image capture device 10 erases all of, or some of, the images from the image memory 43 based on the above instruction. The user may erase all of, or some of, the images stored in the image memory 43 by direct manual operation of the radiation image capture device 10.

Second Exemplary Embodiment

Figure 16:
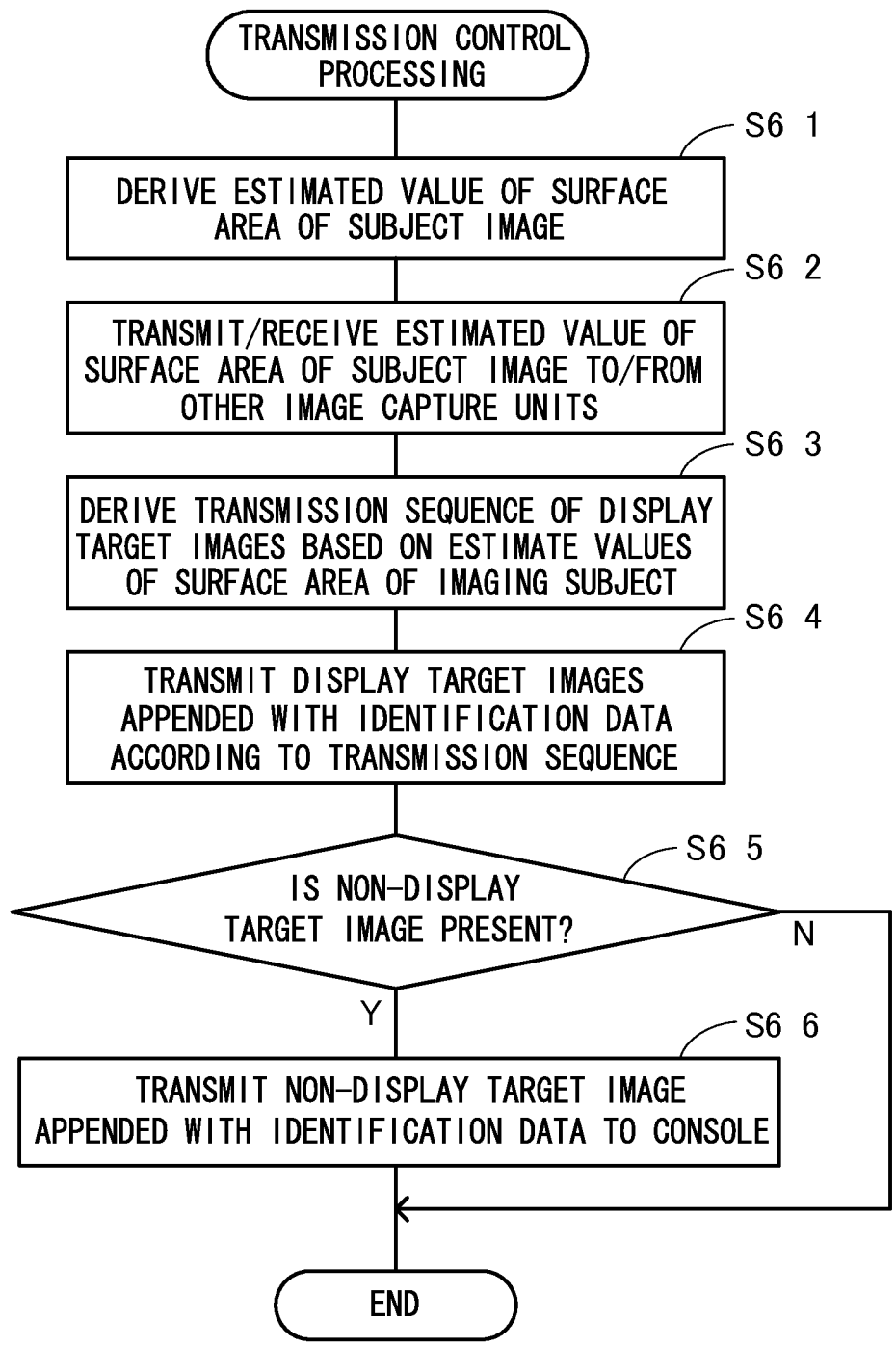
FIG. 16 is a flowchart illustrating a flow of transmission control processing implemented by executing a transmission control program according to an exemplary embodiment of the present invention.

FIG. 16 is a flowchart illustrating a flow of transmission control processing according to a second exemplary embodiment of the present invention, implemented by the CPU 51 configuring the image capture unit controller 50 of each of the image capture units 11A, 11B, 11C executing a transmission control program 57 stored in the ROM 53.

The processing of steps S61 to S63 in the transmission control processing according to the second exemplary embodiment is similar to the processing of steps S41 to S43 of the transmission control processing (see FIG. 12) according to the first exemplary embodiment described above, and so duplicate explanation will be omitted thereof.

At step S64, the CPU 51 of each of the image capture units 11 that has generated a display target image transmits the display target image generated by that image capture unit 11 to the console 70 through the communication cable 110 according to the transmission sequence derived at step S63. Identification data indicating that the image is a display target image and representing the transmission sequence of the image is appended to each of the display target images transmitted. At step S65, the CPU 51 of each of the image capture units 11 determine whether or not there is a non-display target image present. Processing transitions to step S66 in cases in which the CPU 51 of each of the image capture units 11 determines that there is a non-display target image present, and the present routine is ended in cases in which it is determined that a non-display target image is not present.

At step S66, the CPU 51 of each of the image capture units 11 that generated a non-display target image transmits the non-display target image generated in that image capture unit 11 to the console 70 through the communication cable 110. Identification data indicating that the image is a non-display target image is appended to each of the non-display target images transmitted. The display target images and the non-display target images transmitted to the console 70 are stored in the RAM 74 or the HDD 75 of the console 70. Note that the RAM 74 or the HDD 75 according to the second exemplary embodiment of the present invention are each an example of a storage medium of the present invention.

Thus in the transmission control processing according to the second exemplary embodiment, all of the radiation images generated in each of the image capture units 11A, 11B, 11C are transmitted to the console 70, irrespective of whether they are display target images or non-display target images. Display target images are transmitted prior to the non-display target images, and so the display target images are received by the console 70 prior to the non-display target images.

In the present exemplary embodiment, processing to derive the estimated values of surface area of the subject image based on the pixel values of the irradiation detection pixels 32 (step S61), sharing the derived estimated value of surface area of the subject image between each of the image capture units 11 (step S62), and processing to derive the transmission sequence of the radiation images (the display target images) (step S63) are all performed in the radiation image capture device 10, however each of the types of processing may be performed in the console 70.

Figure 17:
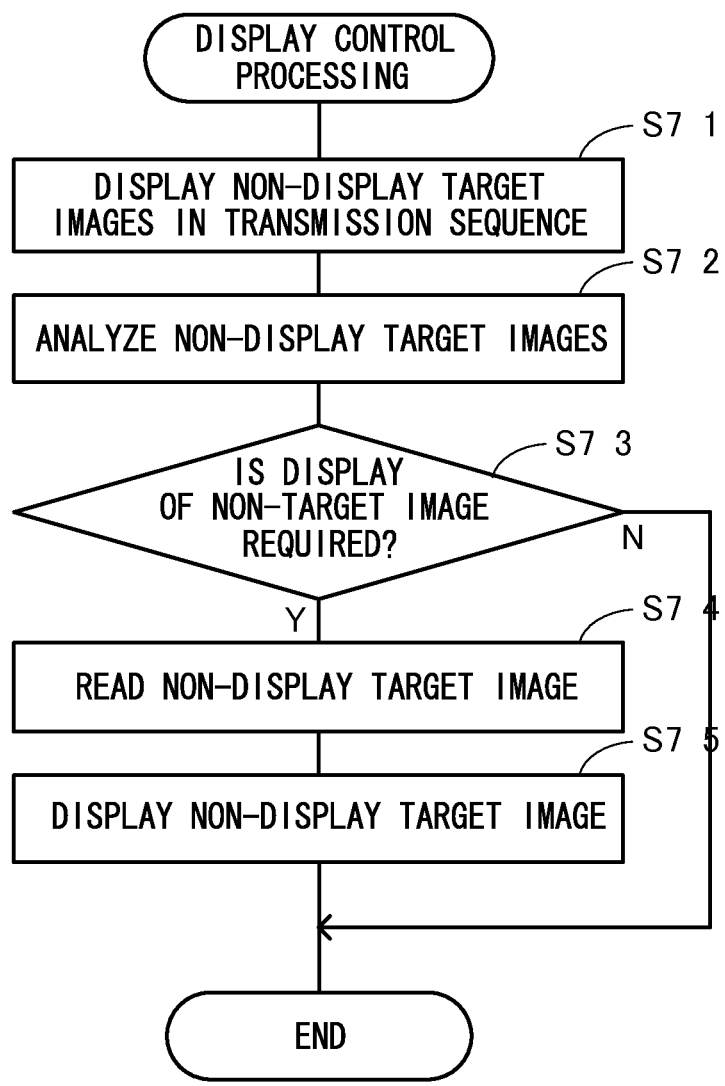
FIG. 17 is a flowchart illustrating a flow of display control processing implemented by executing a display control program according to an exemplary embodiment of the present invention.

FIG. 17 is a flowchart illustrating a flow of display control processing according to the second exemplary embodiment of the present invention implemented by the CPU 73 of the console 70 executing a display control program 83 stored in the ROM 76.

The processing of step S71 to S73 in the display control processing according to the second exemplary embodiment is similar to the processing of step S51 to step S53 in the display control processing according to the first exemplary embodiment described above (see FIG. 13), and so duplicate explanation will be omitted thereof. In step S71, the CPU 73 of the console reads the display target image from the RAM 74 or the HDD 75 and displays the display target image on the display section 71. In such cases, the display target images can be identified by reference to the identification data appended to the display target images.

At step S74, the CPU 73 of the console 70 reads the non-display target images transmitted from the radiation image capture device 10 and stored in the RAM 74 or the HDD 75. In such cases, the non-display target images may be identified by reference to the identification data appended to the non-display target images.

At step S75, the CPU 73 of the console 70 controls the display drive section 77 such that the non-display target image read from the RAM 74 or the HDD 75 is displayed together with the display target image already being displayed on the display section 71. Namely, a combined image of the image designated as the display target image in the radiation image capture device 10 and the non-display target image is displayed on the display section 71. In cases in which the subject image cannot be recognized in the display target images from the image analysis result at step S72, the CPU 73 of the console 70 may also control the display drive section 77 such that the non-display target image is read from the RAM 74 or the HDD 75, and displayed on the display section 71 in place of the display target image.

As described above, in the radiation image capture system 100 according to the second exemplary embodiment of the present invention, all of the radiation images generated in each of the image capture units 11A, 11B, 11C are transmitted to the console 70. Images designated as display target images from out of the radiation images generated in each of the image capture units 11A, 11B, 11C are transmitted to the console 70 prior to the non-display target images, and displayed on the display section 71 of the console 70. Accordingly, the radiation image capture system 100 according to the second exemplary embodiment is capable of shortening the waiting time until image display compared to previously, similarly to in the first exemplary embodiment.

Moreover, since non-display target images can be displayed even in cases in which display target images have not been appropriately designated in the radiation image capture device 10, the image recapture risk can also be avoided.

The radiation image capture system 100 according to the second exemplary embodiment retains the non-display target images in the RAM 74 or the HDD 75 of the console 70, and so the time from determining that there is a need to display the non-display target images until display of the non-display target images on the 71 is shortened compared to in the first exemplary embodiment. The radiation image capture system 100 according to the first exemplary embodiment is, however, capable of shortening the data transmission time since transmission of non-display target images by the radiation image capture device 10 is not required unless there is a transmission request from the console 70. The radiation image capture device 10 according to the first exemplary embodiment is thereby able to transition quickly to the next image capture processing.

From the viewpoint of securing a storage region in the RAM 74 or the HDD 75 of the console 70, these stored images are preferably erased as appropriate. Image erasure from the RAM 74 or the HDD 75 may be performed at, for example, any of the timings (1) to (6) given above.

Third Exemplary Embodiment

Figure 18:
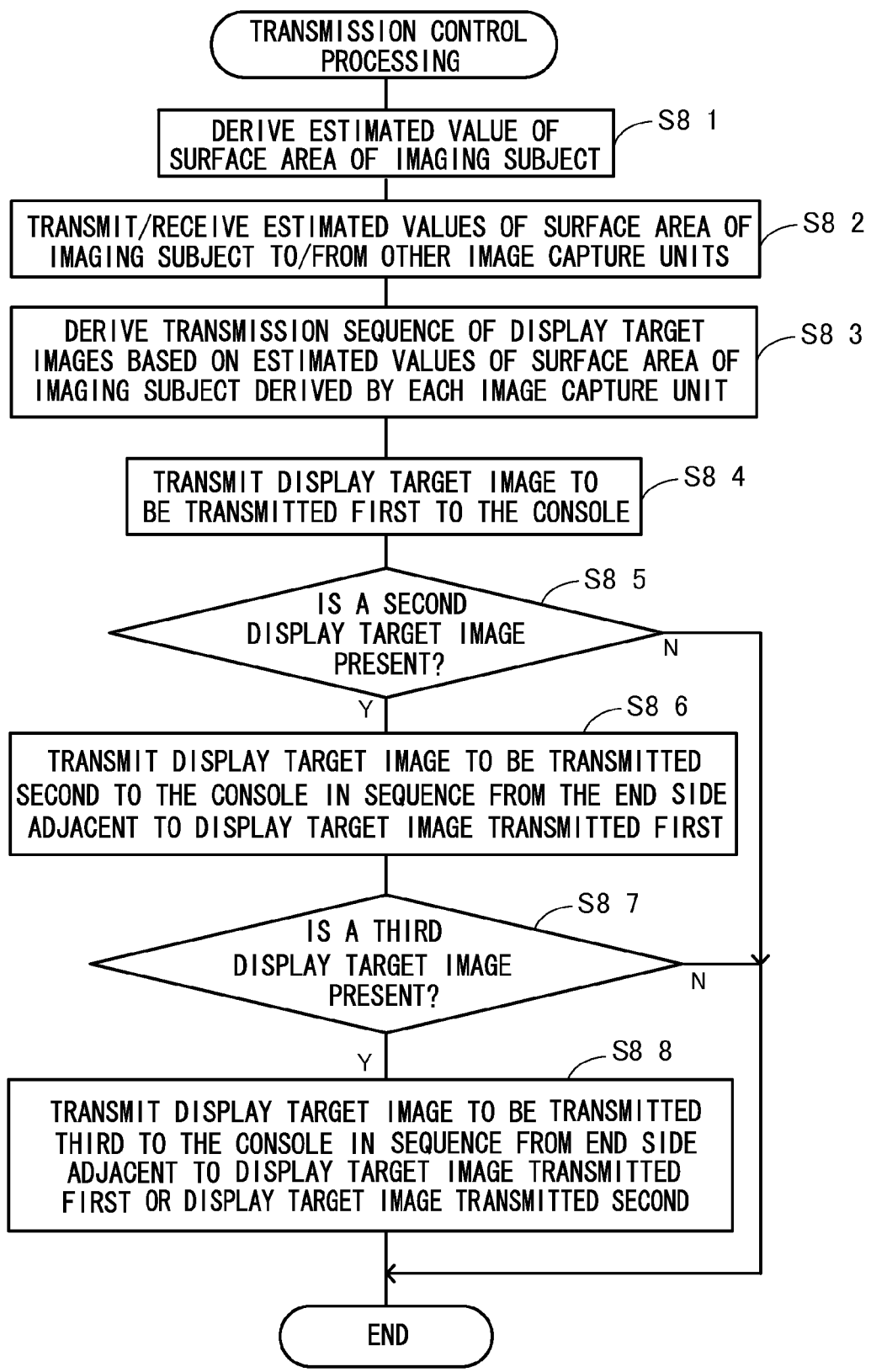
FIG. 18 is a flowchart illustrating a flow of transmission control processing implemented by executing a transmission control program according to an exemplary embodiment of the present invention.

FIG. 18 is a flowchart representing a flow of transmission control processing according to a third exemplary embodiment of the present invention implemented by the CPU 51 configuring the image capture unit controller 50 of each of the image capture units 11A, 11B, 11C executing a transmission control program 57 stored in the ROM 53.

The processing of steps S81 to S83 in the transmission control processing according to the third exemplary embodiment are similar to the processing of steps S41 to S43 of the transmission control processing according to the first exemplary embodiment (see FIG. 12), and so duplicate explanation will be omitted thereof.

At step S84, the CPU 51 of the image capture unit 11 that generated the display target image that is to be transmitted first transmits the display target image generated by that image capture unit 11 to the console 70 through the communication cable 110.

At step S85, the CPU 51 of each of the image capture units 11 determines whether or not there is a display target image present to be transmitted second. Processing transitions to step S86 in cases in which the CPU 51 of each of the image capture units 11 have determined that a display target image to be transmitted second is present, and the present routine is ended in cases in which it is determined that no display target image to be transmitted second is present.

At step S86, the CPU 51 of the image capture unit 11 that generated the display target image to be transmitted second transmits the display target image generated by that image capture unit 11 to the console 70 in sequence from the side of the end adjacent to the display target image first transmitted. Namely, the CPU 51 of the image capture unit 11 that generated the display target image to be transmitted second transmits the display target image generated by that image capture unit 11 so that image data at the side of the end adjacent to the display target image transmitted first is transmitted to the console 70 first. In other words, the CPU 51 of the image capture unit 11 that generated the display target image to be transmitted second transmits the display target image generated by that image capture unit 11 to the console 70 in sequence from the side of the end of the image capture region that configures an image capture region of an overlap portion between the radiation detection panel 20 that generated the display target image first transmitted and its own corresponding radiation detection panel 20.

At step S87, the CPU 51 of each of the image capture units 11 determines whether or not there is a display target image present to be transmitted third. Processing transitions to step S88 if the CPU 51 of each of the image capture units 11 have determined that a display target image to be transmitted third is present, and the present routine is ended if they have determined that no display target image to be transmitted third is present.

At step S88, the CPU 51 of the image capture unit 11 that generated the display target image to be transmitted third transmits the display target image generated by that image capture unit 11 to the console 70 in sequence from the side of the end adjacent to the display target image transmitted first or second. Namely, the CPU 51 of the image capture unit 11 that generated the display target image to be transmitted third transmits the display target image generated by that image capture unit 11 so that image data at the side of the end adjacent to the display target image transmitted first or second is transmitted to the console 70 first. In other words, the CPU 51 of the image capture unit 11 that generated the display target image to be transmitted third transmits the display target image generated by that image capture unit 11 to the console 70 in sequence from the side of the end of the image capture region that configures an image capture region of an overlap portion between the radiation detection panel 20 that generated the display target image transmitted first, or second, and its own corresponding radiation detection panels 20.

In the present exemplary embodiment, processing to derive the estimated values of surface area of the subject image based on the pixel values of the irradiation detection pixels 32 (step S81), sharing the derived estimated value of surface area of the subject image between each of the image capture units 11 (step S82), and processing to derive the transmission sequence of the radiation images (the display target images) (step S83) are all performed in the radiation image capture device 10, however each of the types of processing may be performed in the console 70.

Figure 19:
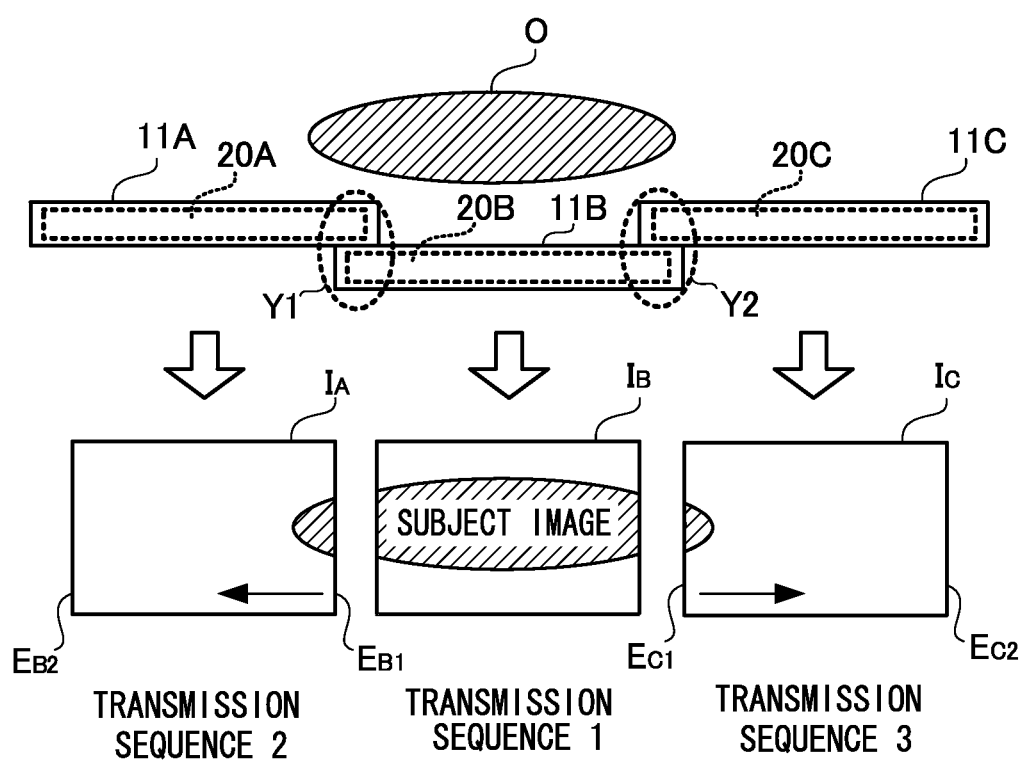
FIG. 19 is a diagram illustrating content of transmission control processing according to an exemplary embodiment of the present invention.

The content of the transmission control processing according to the third exemplary embodiment will now be explained with reference to FIG. 19. This is a case in which the imaging subject O is placed so as to span the three image capture units 11A, 11B, 11C. The radiation image $I_B$ generated by the image capture unit 11B is designated as a display target image, and the transmission sequence of the radiation image $I_B$ is set as first. The radiation image $I_A$ generated by the image capture unit 11A is designated as a display target image and the transmission sequence of the radiation image $I_A$ is set as second. The radiation image $I_C$ generated by the image capture unit 11C is designated as a display target image and the transmission sequence of the radiation image $I_C$ is set as third.

The CPU 51 of the image capture unit 11A that generated the display target image $I_A$ to be transmitted second transmits the display target image $I_A$ generated by the image capture unit 11A to the console 70 in sequence first from the side of end $E_{B1}$ adjacent to the display target image $I_B$ transmitted, and from there onward toward the side of opposing end $E_{B2}$. In other words, the CPU 51 of the image capture unit 11A that generated the display target image $I_A$ to be transmitted second transmits the display target image $I_A$ to the console 70 in sequence first transmitting from the side of the end $E_{B1}$ that forms a portion Y1 where the image capture regions of the radiation detection panel 20A that generated the display target image $I_A$ to be transmitted second, and the radiation detection panel 20B that generated the display target image $I_B$, overlap with each other, and then from there onward toward the opposing side $E_{B2}$. Namely, the display target image $I_A$ is transmitted such that transmission of the image data from the side of the end $E_{B1}$ is prior to transmission of the image data of the end $E_{B2}$ side.

Similarly, the CPU 51 of the image capture unit 11C that generated the display target image $I_C$ to be transmitted third transmits the display target image $I_C$ generated by the image capture unit 11C to the console 70, transmitted in sequence first from the side of end $E_{C1}$ adjacent to the display target image $I_B$ the then onward toward the side of opposing end $E_{C2}$. In other words, the CPU 51 of the image capture unit 11C that generated the display target image $I_C$ to be transmitted third transmits the display target image $I_C$ to the console 70 transmitted first in sequence from the side of the end $E_{C1}$ that forms a portion Y2 where the image capture regions of the radiation detection panel 20C that generated the display target image $I_C$ to be transmitted third, and the radiation detection panel 20B that generated the display target image $I_B$, overlap with each other, and from then onward toward the opposing side $E_2$. Namely, the display target image $I_C$ is transmitted such that transmission of the image data from the side of the end $E_{C1}$ is prior to transmission of the image data of the end $E_{C2}$ side.

After the display target image $I_B$ has been displayed on the display section 71 of the console 70, the display target image $I_A$ is displayed in sequence from the end $E_{B1}$ side adjacent to the display target image $I_B$, and after the display target image $I_A$ has been displayed, the display target image $I_C$ is displayed in sequence from the side of the end $E_{C1}$ adjacent to the display target image b.

Accordingly, out of the display target images generated by each of two adjacent radiation detection panels 20, transmitting the latter transmitted image in sequence from the side of the end that forms the overlapping portion of the two radiation detection panels 20 enables the overall image of the imaging subject to be displayed on the display section 71 of the console 70 as fast as possible.

Fourth Exemplary Embodiment

Figure 20:
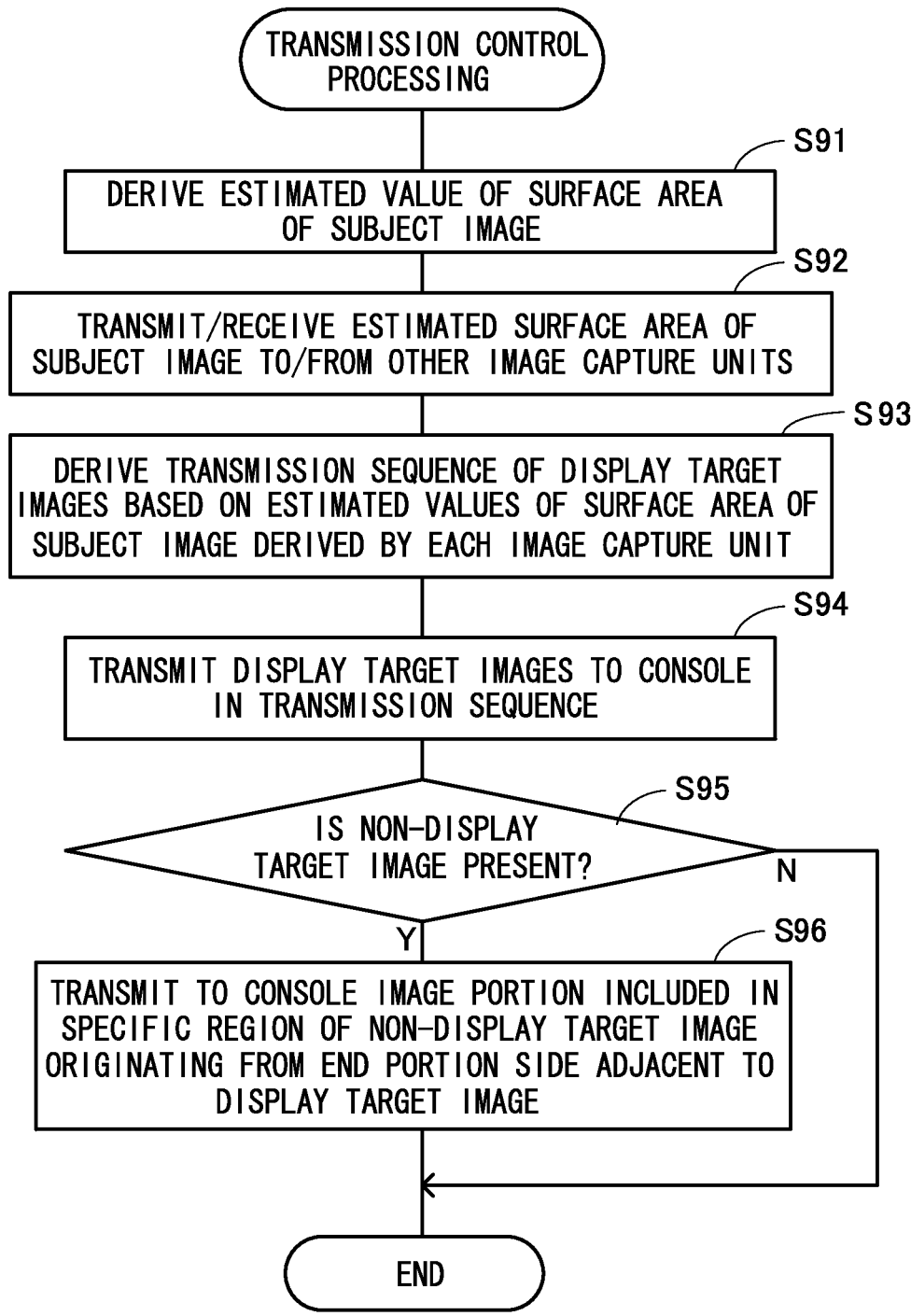
FIG. 20 is a flowchart illustrating a flow of transmission control processing implemented by executing a transmission control program according to an exemplary embodiment of the present invention.

FIG. 20 is a flowchart illustrating a flow of transmission control processing according to a fourth exemplary embodiment of the present invention implemented by the CPU 51 of the image capture unit controller 50 of each of the image capture units 11A, 11B, 11C executing a transmission control program 57 stored in the ROM 53.

The processing of steps S91 to S94 of the transmission control processing according to the fourth exemplary embodiment is similar to the processing of steps S41 to S44 in the transmission control processing according to the first exemplary embodiment (see FIG. 12) and so duplicate explanation will be omitted thereof.

At step S95, the CPU 51 of each of the image capture units 11 determines whether or not there is a non-display target image present. Processing transitions to step S96 in cases in which the CPU 51 of each of the image capture units 11 have determined that there is a non-display target image present, and the present routine is ended in cases in which it is determined that there is no non-display target image present.

At step S96, the CPU 51 of the image capture unit 11 that generated the non-display target image transmits an image portion including a specific range in the non-display target image originating at an end portion on the side adjacent to the display target image to the console 70.

The content of the transmission control processing according to the fourth exemplary embodiment will now be explained with reference to FIG. 21. In this example case only the radiation image $I_B$ generated by the image capture unit 11B is designated as a display target image, and the radiation image $I_A$ generated by the image capture unit 11A and the radiation image $I_C$ generated by the image capture unit 11C are treated as non-display target images.

The CPU 51 of the image capture unit 11A transmits an image portion including a specific range $I_{AE}$ in the non-display target image $I_A$ generated by the image capture unit 11A originating at the end $E_{B1}$ on the side adjacent to the display target image $I_B$ to the console 70. Similarly, the CPU 51 of the image capture unit 11C transmits an image portion including a specific range $I_{CE}$ in the non-display target image $I_C$ generated by the image capture unit 11C originating at the end $E_{C1}$ on the side adjacent to the display target image $I_B$ to the console 70.

In the present exemplary embodiment, processing to derive the estimated values of surface area of the subject image based on the pixel values of the irradiation detection pixels 32 (step S91), sharing the derived estimated value of surface area of the subject image between each of the image capture units 11 (step S92), and processing to derive the transmission sequence of the radiation images (the display target images) (step S93) are all performed in the radiation image capture device 10, however each of the types of processing may be performed in the console 70.

Figure 21:
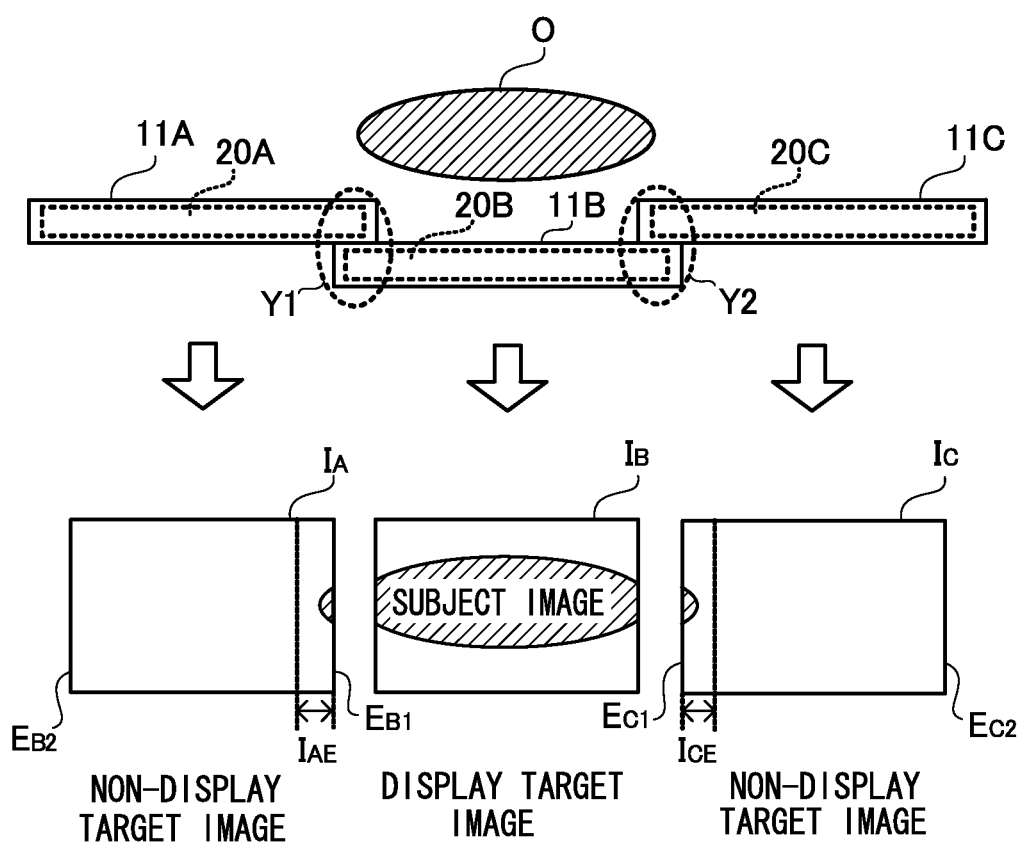
FIG. 21 is a diagram illustrating content of transmission control processing according to an exemplary embodiment of the present invention.

As described above, since the precision of imaging subject recognition is not high in the display target image designation processing (see FIG. 11) when using the irradiation detection pixels 32, sometimes the radiation images $I_A$ and $I_C$ including a portion of the subject image are not designated as the display target images, as illustrated in FIG. 21. In such cases, in the mode of the transmission control processing according to the first exemplary embodiment (FIG. 12) the radiation images $I_A$ and $I_C$ are not transmitted to the console 70. Accordingly, in response to the result of image analysis in the display control processing implemented in the console 70 (see FIG. 13), the radiation images $I_A$ and $I_C$ are displayed later than the radiation image $I_B$, and the waiting time until the whole image of the imaging subject is displayed on the display section 71 is lengthened.

The transmission control processing according to the fourth exemplary embodiment transmits to the console 70 an image portion including a specific range originating at an end portion on the side adjacent to the display target image even for non-display target image. Thus, as illustrated in FIG. 21, even if the imaging subject O is placed spanning the image capture units 11A, 11B, 11C (the radiation detection panels 20A, 20B, 20C) and the image generated by one of the image capture units 11 is treated as a non-display target image, it is still possible to display the whole image of the imaging subject on the display section 71 of the console 70 as fast as possible.

Fifth Exemplary Embodiment

Figure 22:
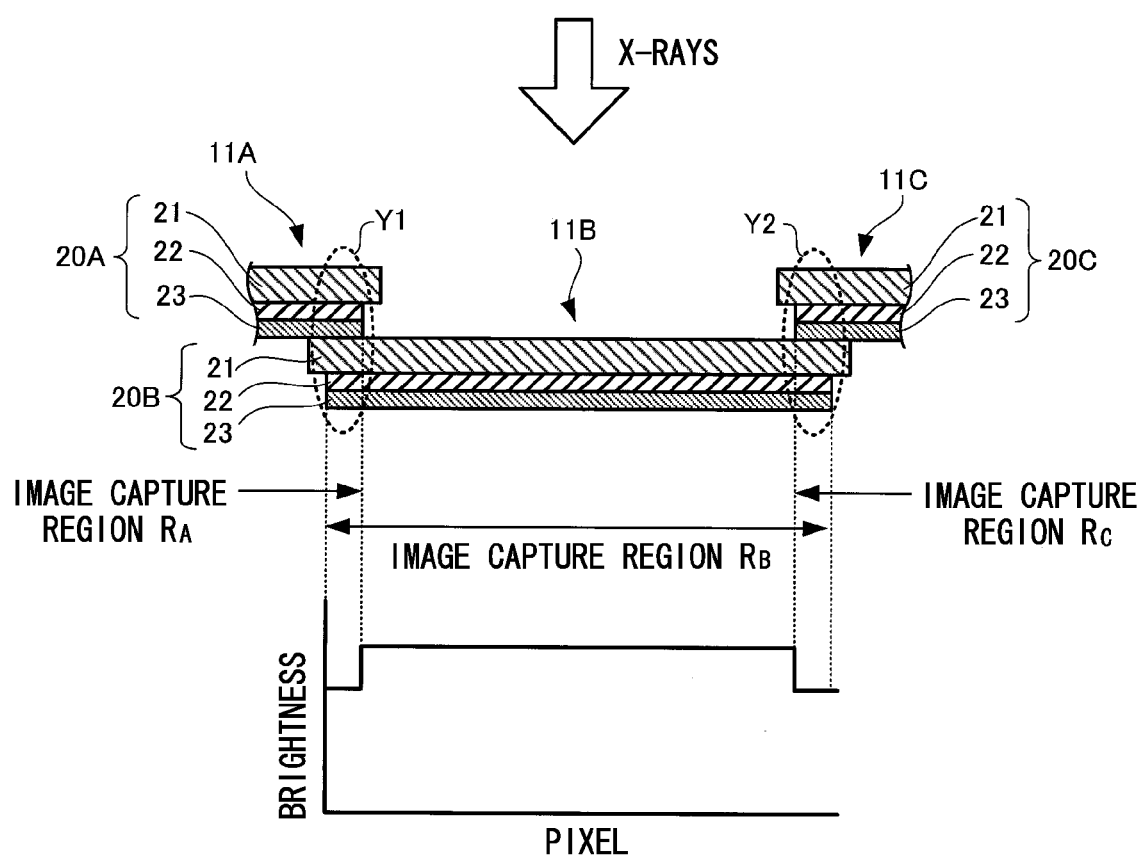
FIG. 22 is a flowchart illustrating a flow of transmission control processing implemented by executing a transmission control program according to an exemplary embodiment of the present invention.

FIG. 22 is a diagram illustrating a brightness distribution of a radiation image generated in cases of a uniform X-ray irradiation dose onto the radiation detection panel 20B of the image capture unit 11B disposed at the center. The radiation detection panel 20B is disposed at the X-ray irradiation direction downstream side of the radiation detection panel 20A of the image capture unit 11A and the radiation detection panel 20C of the image capture unit 11C. One end of the image capture region $R_B$ in the radiation detection panel 20B overlaps in the X-rays irradiation direction with one end of the image capture region $R_A$ of the radiation detection panel 20A, and the other end of the image capture region $R_B$ in the radiation detection panel 20B overlaps in the X-rays irradiation direction with one end of the image capture region $R_C$ of the radiation detection panel 20C. Hereafter the portion where the image capture region $R_A$ and the image capture region $R_B$ overlap is referred to as the overlapping portion Y1, and the portion where the image capture region $R_B$ and the image capture region $R_C$ overlap is referred to as the overlapping portion Y2.

The overlapping portions Y1 and Y2 of the radiation detection panel 20B are irradiated with X-rays attenuated by passing through the image capture region $R_A$ of the radiation detection panel 20A and the image capture region $R_C$ of the radiation detection panel 20C. Accordingly, as illustrated in FIG. 22, the brightness of the portions corresponding to the overlapping portions Y1 and Y2 of the radiation image generated by the radiation detection panel 20B is lower than the brightness of the other portions thereof. Brightness correction is therefore preferably performed to the portions corresponding to the overlapping portions Y1 and Y2 of the radiation image generated by the radiation detection panel 20B.

The brightness correction of the image portions corresponding to the overlapping portion Y1 of the radiation image generated by the radiation detection panel 20B may be performed by employing the pixel values of the corresponding image portions in the overlapping portion Y1 of the radiation image generated by the radiation detection panel 20A. This is because the above pixel values are based on X-rays that include image data corresponding to the image portion corresponding to the overlapping portion Y1 of the radiation image generated by the radiation detection panel 20B, and have not been attenuated.

Similarly, the brightness correction of the image portions corresponding to the overlapping portion Y2 of the radiation image generated by the radiation detection panel 20B may be performed by employing the pixel values of the corresponding image portions in the overlapping portion Y2 of the radiation image generated by the radiation detection panel 20C. This is because the above pixel values are based on X-rays that include image data corresponding to the image portion corresponding to the overlapping portion Y2 of the radiation image generated by the radiation detection panel 20B, and have not been attenuated.

In an radiation image capture system according to the fifth exemplary embodiment of the present invention, even in cases in which the radiation images generated by the image capture unit 11A (the radiation detection panel 20A) and the image capture unit 11C (the radiation detection panel 20C) are non-display target images, the radiation image capture device 10 still transmits image portions corresponding to the overlapping portions Y1 and Y2 to the console 70 as images for use in correction. The console 70 corrects the radiation image as the display target image generated by the image capture unit 11B (the radiation detection panel 20B) using the images for use in correction.

Figure 23:
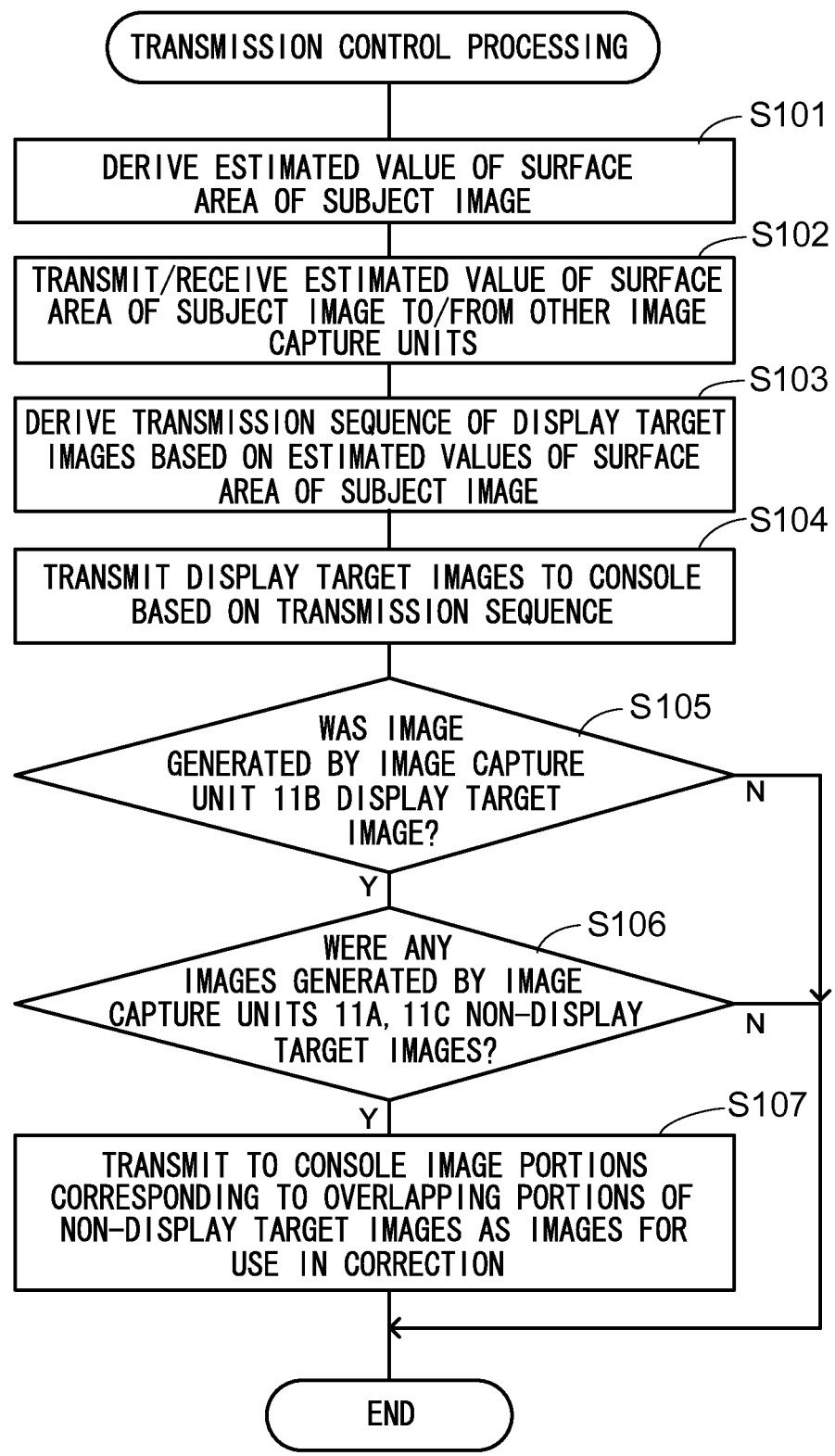
FIG. 23 is a flowchart illustrating a flow of transmission control processing implemented by executing a transmission control program according to an exemplary embodiment of the present invention.

FIG. 23 is a flowchart illustrating a flow of transmission control processing according to a fifth exemplary embodiment of the present invention implemented by the CPU 51 configuring the image capture unit controller 50 of each of the image capture units 11A, 11B, 11C executing the transmission control program 57 stored in the ROM 53.

The processing of steps S101 to S104 in the transmission control processing according to the fifth exemplary embodiment is similar to the processing of steps S41 to S44 of the transmission control processing (see FIG. 12) according to the first exemplary embodiment described above, and so duplicate explanation will be omitted thereof.

At step S105, the CPU 51 of each of the image capture units 11 determines whether or not the radiation image generated by the image capture unit 11B disposed at the X-ray irradiation direction downstream side is a display target image. Processing transitions to step S106 in cases in which the CPU 51 of each of the image capture units 11 have determined that the radiation image generated by the image capture unit 11B disposed at the X-rays irradiation direction downstream side is a display target image, and the present routine is ended if determined that it is not a display target image.

At step S106, the CPU 51 of each of the image capture units 11 determine whether or not the radiation images generated the image capture units 11A and 11C disposed at the X-rays irradiation direction upstream side are non-display target images. Processing transitions to step S107 in cases in which the CPU 51 of each of the image capture units 11 have determined that the radiation images generated by the image capture units 11A and 11C are non-display target images, and the present routine is ended if determined that they are not non-display target images.

At step S107, the CPU 51 of the image capture units 11 that generated the non-display target images (one of the image capture units 11A or 11C, or both) transmit to the console 70 image portions in the non-display image generated by that respective image capture unit 11 corresponding to the overlapping portion Y1 or Y2 as images for use in correction.

In the present exemplary embodiment, processing to derive the estimated values of surface area of the subject image based on the pixel values of the irradiation detection pixels 32 (step S101), sharing the derived estimated value of surface area of the subject image between each of the image capture units 11 (step S102), and processing to derive the transmission sequence of the radiation images (the display target images) (step S103) are all performed in the radiation image capture device 10, however each of the types of processing may be performed in the console 70.

Figure 24:
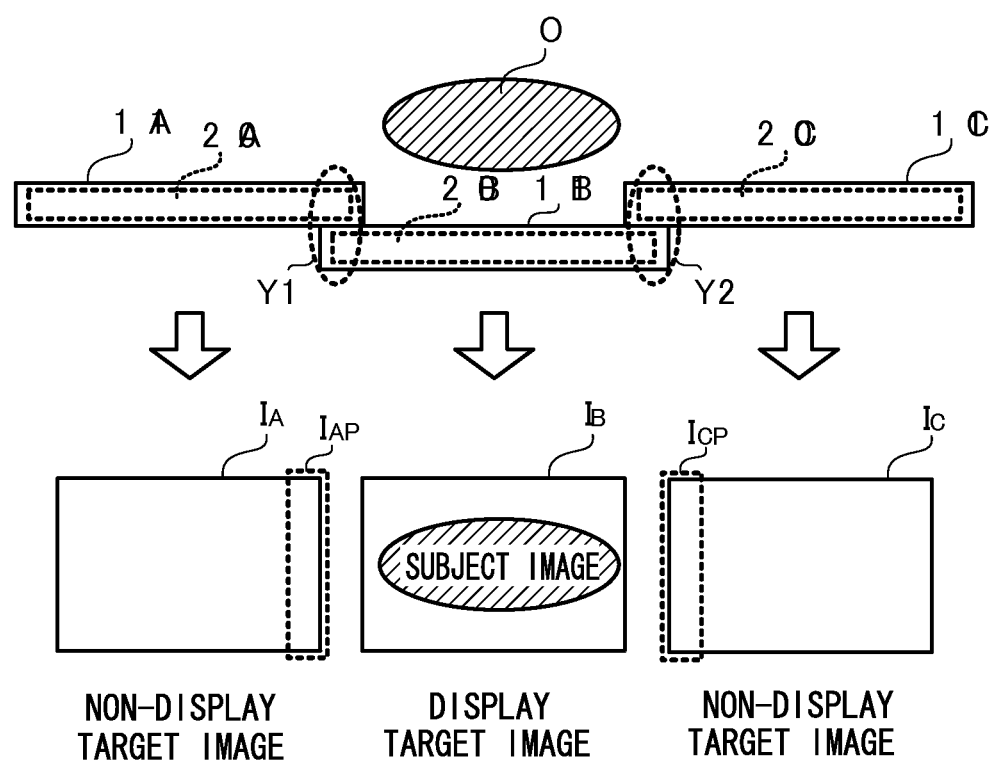
FIG. 24 is a flowchart illustrating content of transmission control processing according to an exemplary embodiment of the present invention.

Explanation follows regarding content of the transmission control processing according to the fifth exemplary embodiment, with reference to FIG. 24. In this example case, only the radiation image $I_B$ generated by the image capture unit 11B (the radiation detection panel 20B) is designated as a display target image, and the radiation image $I_A$ generated by the image capture unit 11A (the radiation detection panel 20A) and the radiation image $I_C$ generated by the image capture unit 11C (the radiation detection panel 20C) are treated as non-display target images.

The CPU 51 of the image capture unit 11A transmits an image portion $I_{AP}$ in the non-display image $I_A$ generated in the image capture unit 11A corresponding to the overlapping portion Y1 as an image for use in correction to the console 70. Similarly, the CPU 51 of the image capture unit 11C transmits to the console 70 an image portion $I_{CP}$ in the non-display image $I_C$ generated by the image capture unit 11C corresponding to the overlapping portion Y2 of the image capture region as an image for use in correction.

Figure 25:
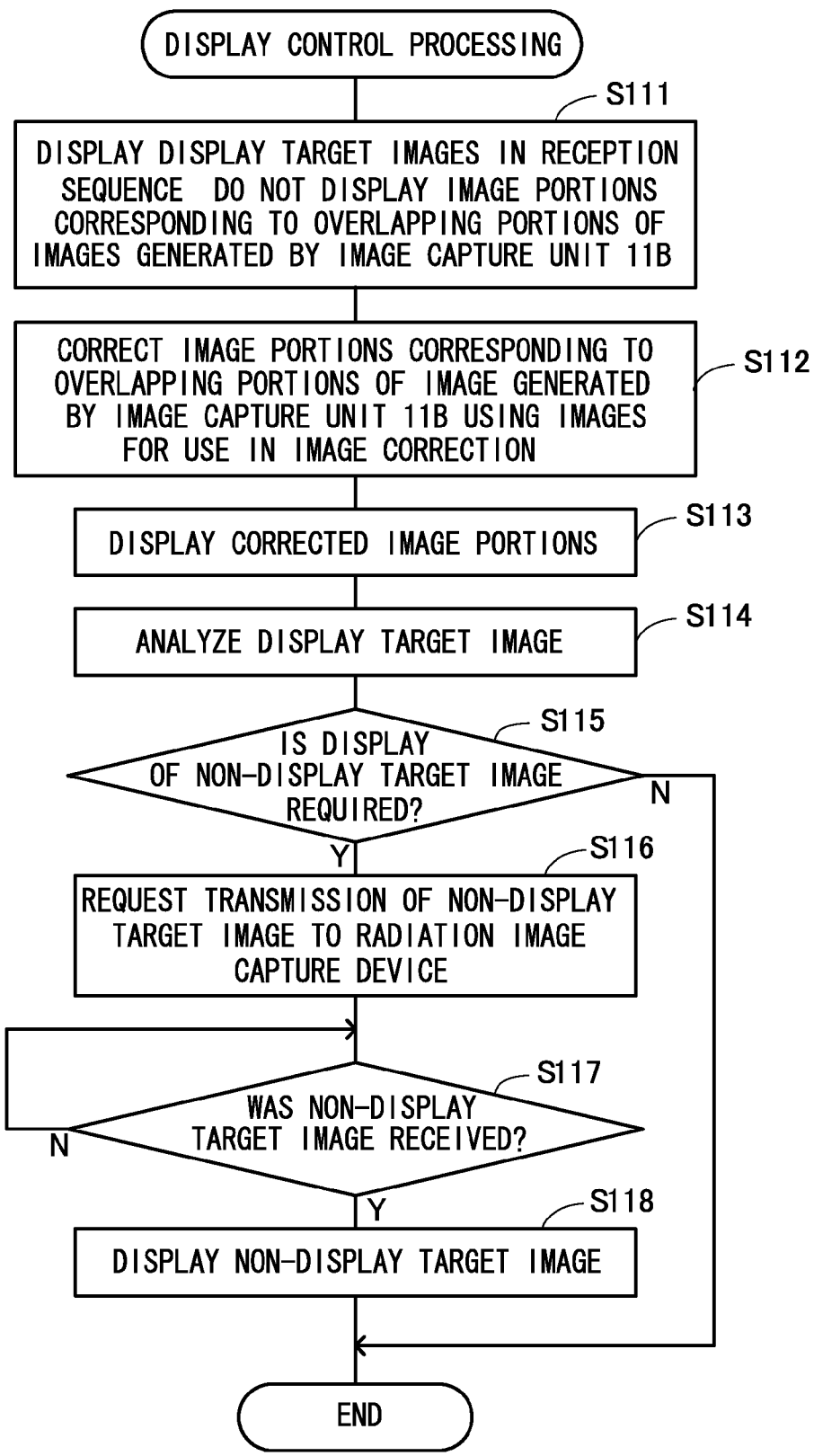
FIG. 25 is a flowchart illustrating a flow of display control processing implemented by executing a display control program according to an exemplary embodiment of the present invention.

FIG. 25 is a flowchart illustrating a flow of display control processing according to a fifth exemplary embodiment of the present invention implemented by the CPU 73 of the console 70 executing a display control program 83 stored in the ROM 76.

At step S111, the CPU 73 of the console 70 displays the display target images transmitted from the radiation image capture device 10 on the display section 71 in their reception sequence. In this example case, the end portions of the display target image (the image portions corresponding to the overlapping portions Y1 and Y2) generated by the image capture unit 11B (the radiation detection panel 20B) are either not displayed or displayed in black.

At step S112, the CPU 73 of the console 70 corrects the end portions of the display target image (the image portions corresponding to the overlapping portions Y1 and Y2) generated by the image capture unit 11B (the radiation detection panel 20B) using the images for use in correction transmitted from the radiation image capture device 10. Namely, the brightness values of each of the pixels in the end portions of the display target image (the image portions corresponding to the overlapping portions Y1 and Y2) generated by the image capture unit 11B (the radiation detection panel 20B) are corrected based on the brightness values of the pixels corresponding to the images for use in correction. Such correction removes the influence from X-ray attenuation at the end portions of the display target image (the image portions corresponding to the overlapping portions Y1 and Y2) generated by the image capture unit 11B (the radiation detection panel 20B).

At step S113, the CPU 73 of the console 70 displays the image portions corrected at step S112 on the display section 71. Namely, the image portions not being displayed or displayed in black at step S111 are displayed through the correction processing. The above correction processing eliminates the brightness difference from the radiation image generated by the image capture unit 11B (the radiation detection panel 20B), as illustrated in FIG. 21.

The processing subsequent to steps S114 to S118 is similar to the processing of steps S52 to S56 in the display control processing of the first exemplary embodiment (see FIG. 13), and so duplicate explanation will be omitted thereof.

As described above, according to the radiation image capture system according to the fifth exemplary embodiment of the present invention, even in cases in which at least one of the radiation images generated by the image capture unit 11A (the radiation detection panel 20A) and the image capture unit 11C (the radiation detection panel 20C) is a non-display target image, brightness correction processing can still be performed using a portion of the non-display target image as an image for use in correction, enabling the quality of the display target image generated by the image capture unit 11B (the radiation detection panel 20B) to be improved.

The rest of the display target image other than the end portions of the display target image (the image portions corresponding to the overlapping portions Y1 and Y2) generated by the image capture unit 11B (the radiation detection panel 20B) are displayed on immediately after being received by the console 70, without waiting for the above correction processing to be completed, enabling a large increase in the waiting time until image display to be avoided. Alternatively, all of the display target image may be displayed at once on the display section 71 when the above correction processing has been completed.

The radiation image capture device 10 only transmits the image portions in the non-display target image required for correction to the console 70, enabling the data transmission time and the correction processing time to be shortened compared to cases in which all the non-display target images are transmitted, and enabling the waiting time to display the image after correction processing to be shortened as a result.

In the present exemplary embodiment, in cases in which the radiation image generated in the image capture unit 11B is treated as a display target image and at least one of the radiation images generated in the image capture units 11A and 11C is treated as a non-display target image, the non-display target image is always transmitted to the console 70 as the image for use in correction, however there is no limitation to such embodiments. For example, the radiation image capture device 10 may transmit an image for use in correction to the console 70 in response to a transmission request from the console 70. The console 70 may, for example, issue a transmission request for an image for use in correction to the radiation image capture device 10 based on a result of analysis of the display target image or based on an instruction through the operation input section 72, and may perform correction processing after reception of the image for use in correction.

Figure 26:
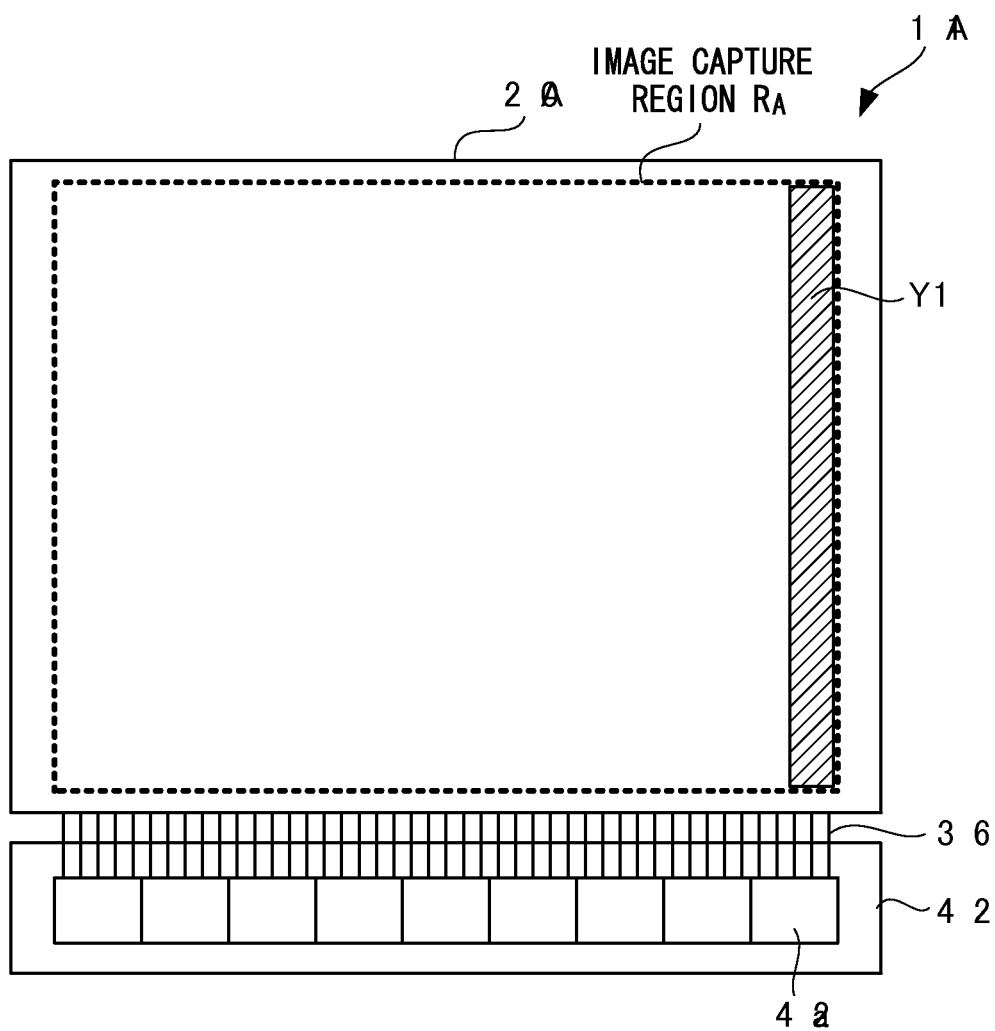
FIG. 26 is a schematic configuration diagram of radiation detection panel 20 and a signal processing section according to an exemplary embodiment of the present invention.

FIG. 26 is a schematic configuration diagram of a radiation detection panel 20A and a signal processor 42 configuring the image capture unit 11A. The signal processor 42 includes plural signal processing circuits 42a respectively connected to plural signal lines 36. Namely, the signal transmitted by each of the signal lines 36 provided to the radiation detection panel 20A are processed in the corresponding signal processing circuit 42a. In FIG. 26, an overlapping portion between the image capture region $R_A$ and the image capture region $R_B$ (omitted from illustration in FIG. 26) is illustrated by hatching as an overlapping portion Y1. As illustrated in FIG. 26, the overlapping portion Y1 is preferably accommodated within a processing target range in a single signal processing circuit 42a. Thus it is possible to create the image data for an image for use in correction by driving a single signal processing circuit 42a (the signal processing circuit 42a on the far right side in FIG. 26), enabling generation of the image for use in correction to be performed quickly. Similarly, in the image capture unit 11C, the overlapping portion Y2 is preferably accommodated within the processing target range of a single signal processing circuit 42a.

Sixth Exemplary Embodiment

A method is known in the field of image processing to identify image blurring with a point spread function (PSF). Namely, a point image is not projected unaltered, and instead is projected while spreading out as a point spread function.

If a source image prior to degradation is denoted by f (x, y), an image after degradation is denoted by g (x, y), and a spatial filter equivalent to a point spread function is denoted h (x, y), then the image after degradation g (x, y) can be expressed by the following Equation (1).

$$g(x,y)=f(x,y)*h(x,y) \qquad \text{Equation (1)}$$

Taking the Fourier transform of Equation (1) yields the following Equation (2).

$$G(u,v)=F(u,v)H(u,v) \qquad \text{Equation (2)}$$

The following Equation (3) is obtained from Equation (2).

$$F(u,v)=G(u,v)/H(u,v) \qquad \text{Equation (3)}$$

Thus the source image prior to degradation can be reproduced by inverse Fourier transformation of the product of the degradation image Fourier transform G (u, v) and the inverse filter 1/H (u, v). In the following such reproduction processing is referred to as point spread correction processing.

Since the image after degradation is an image formed by spreading out of each point image configuring the source image prior to degradation, the spread range of the image after degradation (range over which the source image spreads, the outer edge of a blurred image), namely the spread range of point images based on the point spread function, needs to be identified in order to perform the point spread correction processing. The spread range of the image after degradation may be considered to change according to spread angle and spread distance. The spread angle and spread distance may be considered to correlate to the thickness of the imaging subject (the height, or body thickness, from the imaging plane). Namely, as the thickness (body thickness) of the imaging subject gets thicker, the spread range of the point images gets larger, and it can be considered that the spread range of the subject image also gets larger.

Thus in the radiation image capture system according to a sixth exemplary embodiment of the present invention, at step S13 of the image capture preparation program (see FIG. 9), the radiation image capture device 10 identifies the spread range of the subject image based on the thickness (body thickness) of the imaging subject included in the imaging subject data notified by the console 70, and based on a point spread function. In cases in which the identified spread range of the subject image is included in the non-display target image, the radiation image capture device 10 transmits image portions from the non-display target images including at least the subject image spread range to the console 70 as images for use in correction for point spread correction processing. Note that all of the non-display target images may be transmitted to the console 70 as images for use in correction for point spread correction processing. In cases in which the subject image spread range is included in the non-display target images, the console 70 performs the point spread correction processing on a series of images including the display target images and image portions of the non-display target image that are images for use in correction, as an image after degradation g (x, y).

Figure 27:
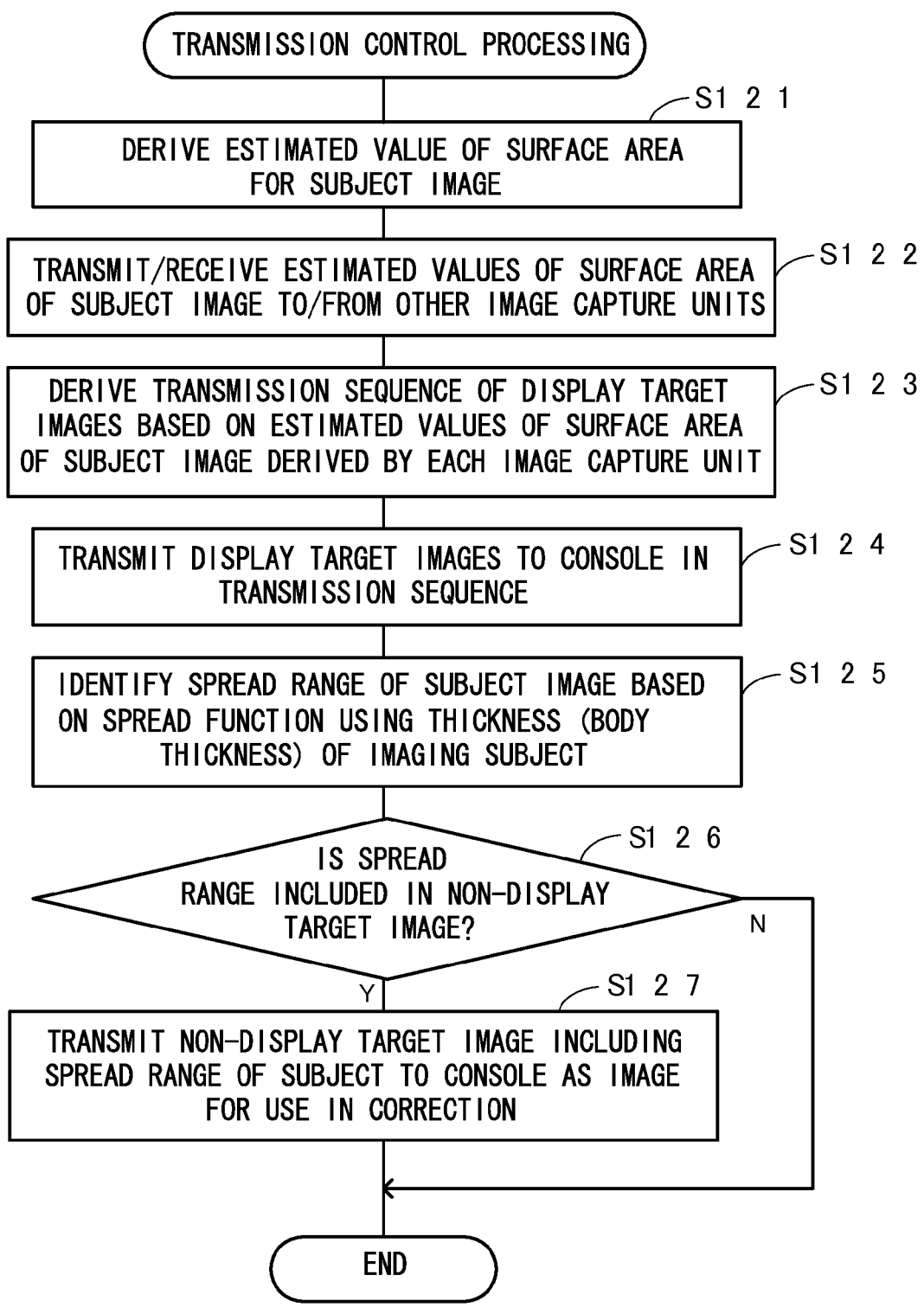
FIG. 27 is a flowchart illustrating a flow of transmission control processing implemented by executing a transmission control program according to an exemplary embodiment of the present invention.

FIG. 27 is a flowchart illustrating a flow of transmission control processing according to the sixth exemplary embodiment of the present invention implemented by the CPUs 51 that configure the image capture unit controllers 50 in each of the image capture units 11A, 11B, 11C executing a transmission control program 57 stored in the ROM 53.

The processing of steps S121 to S124 in the transmission control processing according to the sixth exemplary embodiment is similar to the processing of steps S41 to S44 in the transmission control processing according to the first exemplary embodiment (see FIG. 12), and so duplicate explanation will be omitted thereof.

At step S125, the CPU 51 of each of the image capture units 11 estimates the subject image spread range (range over which the source image spreads, the outer edge of blurred image) based on the result of imaging subject recognition using the thickness (body thickness) of the imaging subject included in the imaging subject data notified by the console 70 at step S13 of the image capture preparation processing (see FIG. 9) and the irradiation detection pixels 32. A table defining correspondence relationships between the thickness (body thickness) of the imaging subject and the spread range of the subject image may, for example, be employed in estimation of the subject image spread range. The table described above may be created based on test measurements using a phantom.

At step S126, the CPU 51 of each of the image capture units 11 determines whether or not the spread range of the subject image estimated at step 125 is included in the non-display target images. Processing transitions to step S127 in cases in which the CPU 51 of each of the image capture units 11 have determined that the subject image spread range is included in the non-display target images, and the present routine is ended in cases in which determination is that the subject image spread range is not included in the non-display target images.

At step S127, the CPU 51 of each of the image capture units 11 that generated a non-display target image including the spread range of the subject image transmit image portions, transmits an image portion that includes the subject image spread range from out of its own generated non-display target image, to the console 70.

In the present exemplary embodiment, the processing to derive the estimated values of surface area of the subject image based on the pixel values of the irradiation detection pixels 32 (step S121), sharing the derived estimated value of surface area of the subject image between each of the image capture units 11 (step S122), and processing to derive the transmission sequence of the radiation images (the display target images) (step S123) are all performed in the radiation image capture device 10, however each of the types of processing may be performed in the console 70.

Figure 28:
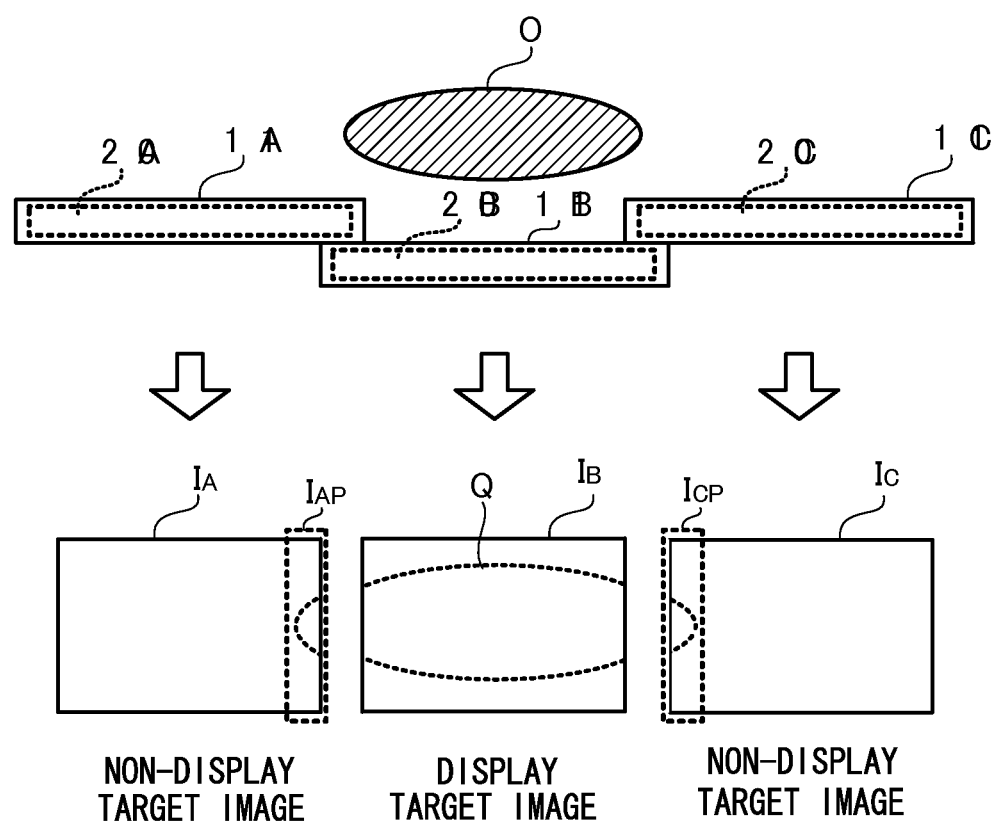
FIG. 28 is a diagram illustrating content of transmission control processing according to an exemplary embodiment of the present invention.

Explanation follows regarding the content of the transmission control processing according to the sixth exemplary embodiment, with reference to FIG. 28. In this example case, only the radiation image $I_B$ generated by the image capture unit 11B (the radiation detection panel 20B) is designated as a display target image, and the radiation image $I_A$ generated by the image capture unit 11A (the radiation detection panel 20A) and the radiation image $I_C$ generated by the image capture unit 11C (the radiation detection panel 20C) are treated as non-display target images. The subject image spread range Q estimated by each of the image capture units 11 is included in each of the radiation images $I_A$, $I_B$, $I_C$, as illustrated in FIG. 27.

The CPU 51 of the image capture unit 11A transmits an image portion $I_{AP}$ from its own generated non-display target image $I_A$ that includes the subject image spread range Q to the console 70 as an image for use in correction. Similarly, the CPU 51 of the image capture unit 11C transmits an image portion $I_{CP}$ from its own generated non-display target image $I_C$ that includes the subject image spread range Q to the console 70 as an image for use in correction.

Figure 29:
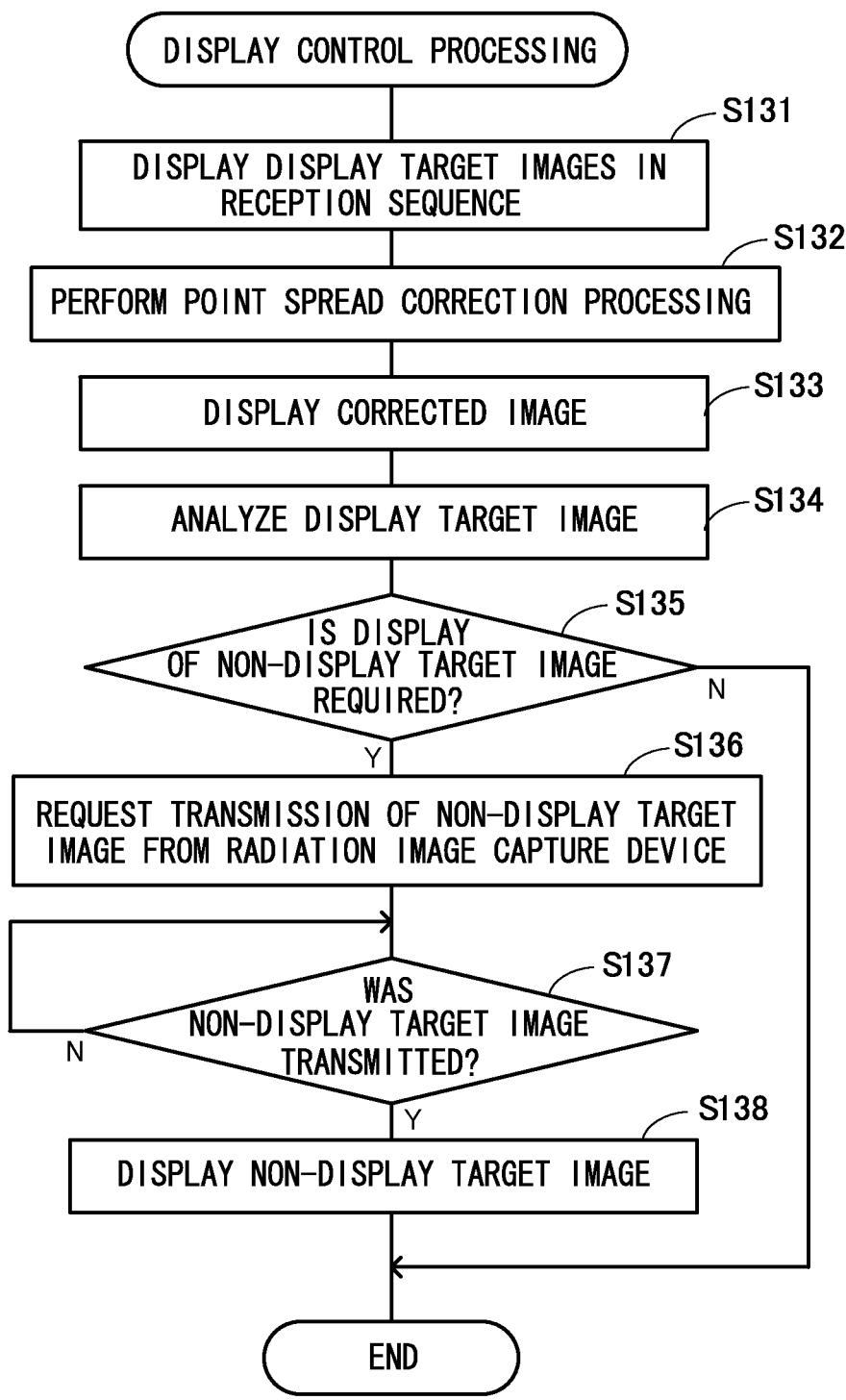
FIG. 29 is a flowchart illustrating a flow of display control processing implemented by executing a display control program according to an exemplary embodiment of the present invention.

FIG. 29 is a flowchart illustrating a flow of display control processing according to the sixth exemplary embodiment of the present invention implemented by the CPU 73 of the console 70 executing a display control program 83 stored in the ROM 76.

At step S131, the CPU 73 of the console 70 controls the display drive section 77 and displays the display target images stored in the RAM 74 or the HDD 75 of each of the image capture units 11 on the display section 71 in the reception sequence from the radiation image capture device 10. Namely, at step S131, the images prior to point spread correction processing are displayed on the display section 71.

At step S132, the CPU 73 of the console 70 implements the point spread correction processing for the display target images displayed on the display section 71. In cases in which the CPU 73 of the console 70 transmits image portions of the non-display target images from the radiation image capture device 10 as images for use in correction, a series of images, including the display target images and the image portions of the non-display target images that are the images for use in correction, are treated as the image after degradation g (x, y), and point spread correction processing is performed thereon.

At step S133, the CPU 73 of the console 70 displays the display target image that has been subjected to point spread correction processing on the display section 71.

The subsequent processing of steps S134 to S138 is similar to the processing of steps S52 to S56 in the display control processing according to the first exemplary embodiment (see FIG. 13), and so duplicate explanation will be omitted thereof.

As described above, the radiation image capture system according to the sixth exemplary embodiment of the present invention uses point spread correction processing on the image portions that include the spread range of the subject image, as images for use in correction, even for the non-display target images. This thereby enables point spread correction processing to be performed for the display target images even in cases in which the spread range of the subject image is included in the non-display target images.

Moreover, the display target images are displayed in the state prior to correction processing immediately after receipt by the console 70, without waiting to complete the point spread correction processing, enabling a large increase in the waiting time until image display to be avoided. The post-correction processing display target images may be displayed on the display section 71 after the point spread correction processing has been completed.

The radiation image capture device 10 only transmits the image portions in the non-display target image that require correction to the console 70, enabling the data transmission time and the correction processing time to be shortened compared to cases in which the whole of the non-display target images is transmitted. The waiting time to display the post-correction processing images can be shorted as a result.

In the present exemplary embodiment, the image portions of the non-display target images are always transmitted as images for use in correction to the console 70 in cases in which the spread range of the subject image is included in the non-display target images, however there is no limitation to such a mode. For example, the radiation image capture device 10 may transmit the images for use in correction to the console 70 in response to a transmission request from the console 70. The console 70 may, for example, issue a transmission request for image for use in correction to the radiation image capture device 10 based on results of analysis on the display target image or in response to an instruction from a user via the operation input section 72, and then implement the correction processing after receipt of the images for use in correction.

In the present exemplary embodiment, the subject image spread range Q is estimated based on the results of imaging subject recognition using the thickness of the imaging subject (body thickness) included in the imaging subject data notified by the console 70 and the irradiation detection pixels 32, and the image portions $I_{AP}$, $I_{CP}$ extracted as images for use in correction, however there is no limitation thereto. For example, the radiation image capture device 10 may estimate the spread range of the subject image by performing imaging analysis in each of the image capture units 11 on the image generated by that image capture unit 11, and extract the image portions $I_{AP}$, $I_{CP}$ as images for use in correction.

Moreover, the radiation image capture device 10 may consider information in the imaging subject data notified by the console 70 other than the body thickness (for example the sex, weight, age) to extract the image portions $I_{AP}$, $I_{CP}$ as images for use in correction. The subject image spread range Q is presumed to be governed by scattered radiation, and much scattered radiation is generated at high density sites such as bones. Consequently, the scattered radiation generation conditions may be estimated by estimating the skeletal structure of the imaging subject based on various data included in the imaging subject data (sex, weight, age, body thickness), enabling the subject image spread range Q to be estimated.

The radiation image capture device 10 may extract the image portions $I_{AP}$, $I_{CP}$, as images for use in correction, based on the X-ray irradiation conditions notified by the console 70, such as the tube voltage, tube current, source-image distance (SID). For example, the higher the tube voltage, the higher the linearity of the X-rays, and the smaller the effect of scattered radiation, leading to a small subject image spread range Q. The tube current is proportional to the X-ray dose, and affects the density of the radiation images. The incident angle of the X-rays to the imaging subject changes according to the SID. Namely, the larger the SID, the nearer the incident angle of the X-rays on the imaging subject is to orthogonal. The effect of scattered radiation is less liable to be received as a result, leading to a small subject image spread range Q. However, as the SID gets smaller, this leads to oblique incidence at the side edges of the imaging subject. The effect of scattered radiation is more liable to be received as a result, leading to a large subject image spread range Q.

Modified Examples

Explanation has been given above of radiation image capture systems according to exemplary embodiments of the present invention, however the present invention is not limited to the exemplary embodiments described above, and various modifications are possible.

In each of the exemplary embodiments above, designation of the display target images was performed based on pixel values of the irradiation detection pixels 32, however there is no limitation thereto. For example, the radiation image capture device 10 may designate the display target images based on imaging subject attribute data, such as sex, age, height, imaging target site, posture during image capture of the patient who is the imaging subject, included in the imaging subject data transmitted from the console 70 at step S13 of the image capture preparation processing (see FIG. 9). For example, as illustrated in FIG. 1, in cases in which the radiation image capture device 10 is disposed for use in upright imaging, for an adult male patient as the imaging subject and the chest region as the imaging site, radiation images generated by the image capture unit 11A positioned uppermost of the image capture units 11A, 11B, 11C and the image capture unit 11B positioned in the middle thereof may be designated as the display target images. When performing display target image designation based on such imaging subject data, a table may be employed in which correspondence relationships are defined between the imaging subject attribute data, such as sex, age, height, target site, posture during image capture of the patient who is the imaging subject, and the image capture unit 11 to be employed for imaging. Thus designating the display target images by employing imaging subject attribute data and the table enables the processing time to be shorted compared with cases in which display target image designation is performed based on pixel values of the irradiation detection pixels 32.

Moreover, in preparation for imaging, in cases in which the image capture units 11 to be employed for imaging are designated by the user, the radiation images generated by the designated image capture units 11 may be designated as the display target images. For example, designation data designating the display target image or the image capture units 11 to be used may be transmitted from the console 70 to the radiation image capture device 10 together with the imaging subject data at step S13 of the image capture preparation processing (see FIG. 9). The radiation image capture device 10 may designate the display target images based on the designation data. This thereby enables the processing time for designating the display target images to be shortened by designating the display target images based on the user designation, and enables more appropriate images to be designated as the display target images.

Moreover, in the display target image designation processing (see FIG. 11), in cases in which it is determined that the CPUs 51 of the respective image capture units 11 have failed to detect the imaging subject based on the pixel values of the irradiation detection pixels 32 (error cases), all of the radiation images generated by the respective image capture units 11A, 11B, 11C may be designated as the display target images. In such error cases, since all the images are treated as display target images, there is no execution of processing to additionally display the non-display target images, with the result that it is highly likely that waiting time to display the desired image can be shortened. Moreover, in cases in which the imaging subject was detected at the two end image capture units 11A, 11C, then this may be taken as detecting the imaging subject in the image capture unit 11B at the center, and all of the radiation images generated in the respective image capture units 11A, 11B, 11C may be designated as the display target images.

In each of the exemplary embodiments described above, the transmission sequence of the display target images to the console 70 is derived based on estimated values of the surface area of the subject image derived based on the pixel values of the irradiation detection pixels 32, however there is no limitation thereto. For example, radiation image capture device 10 may derive the transmission sequence of the display target images based on the imaging subject attribute data, such as sex, age, height, imaging target site, and posture during image capture, of the patient who is the imaging subject included in the imaging subject data transmitted by the console 70 at step 13 of the image capture preparation processing (see FIG. 9). For example, as illustrated in FIG. 1, in cases in which the radiation image capture device 10 is disposed for use in upright imaging, for an adult male patient as the imaging subject and the chest region as the imaging site, a transmission sequence may be determined such that the radiation image generated by the image capture unit 11A positioned uppermost is transmitted to the console 70 first, and the radiation image generated by the image capture unit 11B positioned in the middle is transmitted second. Thus when determining the transmission sequence of the display target images based on the imaging subject attribute data, a table may be employed in which correspondence relationships are defined between the imaging subject attribute data, such as sex, age, height, imaging target site, posture during image capture of the imaging subject, and transmission sequence of the display target images. This deriving the transmission sequence of the display target images using the imaging subject attribute data and a table thereby enables the processing time to be shorted in comparison to cases in which the transmission sequence is derived based on the pixel values of the irradiation detection pixels 32.

Moreover, in preparation for imaging, in cases in which the user has designated the image capture units 11 to employ in imaging and the transmission sequence of the display target images, as well as designating the radiation images generated in the designated image capture units 11 as the display target images, the transmission sequence of the display target images to the console 70 may be determined according to the designated sequence. For example, together with the imaging subject data, at step S13 in the image capture preparation processing (see FIG. 9), designation data designating display target images or the image capture units 11 to be employed, and transmission sequence data indicating the transmission sequence for each of the plural display target images imaging subject data, may be transmitted from the console 70 to the radiation image capture device 10. Together with designating the display target images based on the designation data and the transmission sequence data, the radiation image capture device 10 may also determine the transmission sequence of the display target images. Determining the transmission sequence of the display target images based on user designation in this manner enables the processing time of the transmission control processing (see FIG. 12) to be shortened, and enables the user desired image to be displayed on the display section 71 of the console 70 as fast as possible.

In cases in which the CPU 51 of each of the image capture units 11 determines that imaging subject detection based on the pixel values of the irradiation detection pixels 32 has failed (error cases), all of the radiation images generated by the respective image capture units 11A, 11B, 11C may be designated as the display target images. In such cases, the transmission sequence for each of the display target image may be a predetermined sequence for transmission. Moreover, in cases in which the imaging subject was detected at the two end image capture units 11A, 11C, then this may be taken as detecting the imaging subject in the image capture unit 11B at the center, and all of the radiation images generated in the respective image capture units 11A, 11B, 11C may be designated as the display target images. In such cases, the radiation images generated by the image capture units 11A, 11C may be transmitted to the console 70 first, and the image generated in the image capture unit 11B may be transmitted to the console 70 last.

Configuration may be made such that in cases in which the display target images generated in the two mutually adjacent image capture units 11A and 11B or image capture units 11B and 11C are transmitted to the console 70, the display target image generated by the image capture unit 11B disposed at the center is always transmitted to the console 70 first. There is generally a high probability of the region of interest being disposed on the central image capture unit 11B, and so determining the transmission sequence as described above enables images of higher importance to be transmitted to the console 70 first.

Moreover, in each of the above exemplary embodiments, designation of the display target images, and deriving of the transmission sequence for the display target images, are performed based on the pixel values of the irradiation detection pixels 32 provided in each of the radiation detection panels 20; however there is no limitation thereto. For example, it is possible to employ a known radiation detection device, such as an ion chamber, externally to the radiation image capture device 10 in place of the irradiation detection pixels 32. An ion chamber is configured with a high voltage electrode and a signal electrode disposed facing each other in a metal container enclosing an inert gas having a high X-ray absorption coefficient, such as xenon gas. X-rays penetrating the metal container of the ion chamber electrolyze the enclosed gas, and X-rays can be detected by current that flows between the high voltage electrode and the signal electrode. In cases in which an ion chamber is employed in place of the irradiation detection pixels 32, preferably plural ion chambers are respectively provided to each of the image capture units 11A, 11B, 11C. In such cases, the ion chambers can perform equivalent roles to the irradiation detection pixels 32 by defining the positional relationships between each of the ion chambers and the radiation detection panels 20. Namely, it is possible to designate the display target images and to derive the transmission sequence of the display target images based on the output from each of the ion chambers. Using the ion chambers enables the display target images to be designated and the transmission sequence of the display target images to be derived based on the X-rays irradiation doses, even in a radiation image capture device not including irradiation detection pixels.

In the display control processing according to each of the exemplary embodiments described above, determination is made as to whether or not display of the non-display target images is required based on the result of image analysis of the display target image in the console 70, however there is no limitation to such embodiments. For example, determination may be made as to whether or not display of the non-display target images is required based on an instruction from a user through the operation input section 72 of the console 70. Namely, a user checks the display target image displayed on the display section 71 of the console 70, and requests display of non-display target images if required by operating the operation input section 72. In the embodiment of display control processing according to the first exemplary embodiment (see FIG. 13), a transmission request for a non-display target image is transmitted from the console 70 to the radiation image capture device 10 according to the user operation, and in the embodiment of the display control processing according to the second exemplary embodiment (see FIG. 17), a non-display target image is read from the RAM 74 or the HDD 75 of the console 70 according to the user operation.

Moreover, in each of the above exemplary embodiments, the display target images are displayed on the display section 71 in the sequence received (namely in the transmission sequence set in the radiation image capture device 10); however there is no limitation to such a mode. For example, the console 70 may perform image analysis prior to displaying the display target images, and display the display target images in a display sequence derived according to the results of analysis.

In each of the exemplary embodiment described above, examples have been given of cases in which the radiation images generated in the radiation image capture device 10 are displayed on the display section 71 of the console 70, however there is no limitation to such embodiments. The radiation images generated in the radiation image capture device 10 may, for example, be displayed on a display screen of a separate device to the console 70, such as a portable display terminal device. In such cases, the portable display terminal device or the like may include functions substantially similar to those of the console 70, and may execute display control processing according to the above exemplary embodiments. The display control processing according to each of the above exemplary embodiments may also be executed in the console 70, and the portable display terminal device or the like only perform image display under control of the console 70. Namely, the portable display terminal device or the like may be a device including the function of the display section 71 of the console 70.

In each of the above exemplary embodiments, the radiation images generated in each of the image capture units 11A, 11B, 11C are stored in the respective image memories 43 of the radiation image capture device 10, or the RAM 74 or the HDD 75 of the console 70, however there is no limitation to such embodiments. For example, the radiation images generated in the respective image capture units 11A, 11B, 11C may be stored on an external storage medium connected to enable communication with both the radiation image capture device 10 and the console 70. In such cases the non-display target images may be read from the external storage medium in response to a transmission request from the console 70.

Moreover, in each of the exemplary embodiments above, examples are given of cases in which an intermediate conversion type of radiation detection panel is employed, however a direction conversion type radiation detection panel may be employed. Moreover, although in each of the exemplary embodiments described above explanation has been given in which X-rays are employed as the radiation that is irradiated during radiation image capture, other radiation may be employed therefore, such as gamma rays, ultraviolet light, a neutron beam or the like. It is also possible to implement combinations of each of the types of processing and each of the exemplary embodiments described above.

According to an aspect of the present invention, a radiation image capture device is provided, wherein the designation section designates the display target image based on detection signals from respective sensors that are provided corresponding to each of the plural radiation detection panels and output detection signals of magnitude according to a dose of irradiated radiation.

According to an aspect of the present invention, a radiation image capture device is provided, wherein the designation section designates the display target image based on attribute data indicating attributes of the imaging subject.

According to an aspect of the present invention, a radiation image capture device is provided, wherein the designation section designates the display target image based on data supplied from the outside of the radiation image capture device designating the display target image.

According to an aspect of the present invention, a radiation image capture device is provided, wherein an external device outside of the radiation image capture device determines the presence or absence of an imaging subject on each of the radiation detection panels based on detection signals from respective sensors that are provided to correspond to each of the plural radiation detection panels and output detection signals of magnitude according to a dose of irradiated radiation, and the designation section designates the display target image based on the determination result of the presence or absence of the imaging subject by the external device.

According to an aspect of the present invention, a radiation image capture device is provided, wherein in cases in which plural images have been designated as display target images, the transmission section derives a transmission sequence for the plural display target images and transmits to the outside of the radiation image capture device the plural display target images in sequence according to the derived transmission sequence.

According to an aspect of the present invention, a radiation image capture device is provided, wherein the transmission section derives the transmission sequence for the plural display target images based on detection signals from respective sensors that are provided corresponding to each of the plural radiation detection panels and output detection signals of magnitude according to a dose of irradiated radiation.

According to an aspect of the present invention, a radiation image capture device is provided, wherein the transmission section derives the transmission sequence of the plural display target images based on attribute data indicating attributes of the imaging subject.

According to an aspect of the present invention, a radiation image capture device is provided, wherein in cases in which plural images have been designated as display target images, the transmission section transmits to the outside of the radiation image capture device the plural display target images in sequence according to a transmission sequence represented by data supplied from the outside of the radiation image capture device designating the transmission sequence for each of the plural display target images.

According to an aspect of the present invention, a radiation image capture device is provided, wherein, in cases in which plural images have been designated as display target images, an external device outside of the radiation image capture device derives a transmission sequence for the plural display target images based on detection signals from respective sensors that are provided corresponding to each of the plural radiation detection panels and output detection signals of magnitude according to a dose of irradiated radiation, and the transmission section transmits to the outside of the radiation image capture device the plural display target images in sequence according to the transmission sequence derived by the external device.

According to an aspect of the present invention, a radiation image capture device is provided, wherein the plural respective radiation detection panels are disposed such that end portions of image capture regions able to generate radiation images overlap between mutually adjacent radiation detection panels, and the transmission section transmits to the outside of the radiation image capture device the latter transmitted image, from two display target images respectively generated by two mutually adjacent radiation detection panels, in sequence from the end portion on the side adjacent to the previously transmitted image.

According to an aspect of the present invention, a radiation image capture device is provided, wherein the plural respective radiation detection panels are disposed such that end portions of image capture regions are able to generate radiation images overlapping with mutually adjacent radiation detection panels, and the transmission section transmits to the outside of the radiation image capture device an image portion included in a specific range originating at an end portion on a side adjacent to the display target image in a radiation image other than the display target image.

According to an aspect of the present invention, a radiation image capture device is provided, wherein the plural respective radiation detection panels share detection data indicating that radiation has been detected by one of the radiation detection panels, and transition to an image capture operation of radiation images based on the detection data.

According to an aspect of the present invention, a radiation image capture device is provided, wherein the plural respective radiation detection panels are disposed such that end portions of image capture regions are able to generate radiation images overlapping in the radiation irradiation direction with mutually adjacent radiation detection panels, and, out of radiation images generated by a first radiation detection panel that is disposed at the radiation irradiation direction downstream side out of plural radiation detection panels and that generates the display target image, and by an adjacent second radiation detection panel that is disposed and at the radiation irradiation direction upstream side and that generates a radiation image other than the display target image, a transmission section transmits to the outside of the radiation image capture device at least an image portion corresponding to an overlapping portion where the image capture region of the first radiation detection panel and the image capture region of the second radiation detection panel overlap with each other as an image for use in correction.

According to an aspect of the present invention, a radiation image capture device is provided, wherein, based on data representing at least one selected from the group consisting of an attribute of a subject imaging, the plural radiation images, and an image capture condition, the transmission section identifies a spread range of an imaging subject based on a point spread function, and in cases in which the identified subject image spread range is included in a radiation image other than the display target image, out of the radiation image other than the display target image, at least an image portion including the spread range of the subject image is transmitted to the outside of the radiation image capture device as an image for use in correction.

According to an aspect of the present invention, a radiation image capture device is provided further including a storage medium that stores at least a radiation image other than the display target image from the plural radiation images, wherein the transmission section transmits to the outside of the radiation image capture device the display target image from the plural radiation images.

According to an aspect of the present invention, a radiation image capture system is provided including, any one of the above radiation image capture devices, a storage medium that stores at least a radiation image other than the display target image from the plural radiation images, and a controller including a display controller that displays the display target image received from the radiation image capture device on a display section, and in cases in which a display request has been made, displays on the display section together with the display target image the radiation image other than the display target image stored on the storage medium, and corrects the display target image generated by the first radiation detection panel using the image for use in correction.

According to an aspect of the present invention, a radiation image capture system is provided, wherein the display controller displays image portions of the display target image generated by the first radiation detection panel not corresponding to the overlapping portion on the display section prior to displaying the image portion corresponding to the overlapping portion, and displays the image portion corresponding to the overlapping portion on the display section after being corrected using the image for use in correction.

According to an aspect of the present invention, a radiation image capture system is provided, including any one of the above radiation image capture devices, a storage medium that stores at least a radiation image other than the display target image from the plural radiation images, and a controller including a display controller that displays the display target image received from the radiation image capture device on a display section, and in cases in which a display request has been made, displays on the display section together with the display target image the radiation image other than the display target image stored on the storage medium, and corrects the display target image using the image for use in correction.

According to an aspect of the present invention, a radiation image capture system is provided, including any one of the above the radiation image capture devices, and a controller including a display controller that displays the display target image received from the radiation image capture device on a display section, and in cases in which a display request has been made, requests the radiation image capture device to transmit the radiation image other than the display target image stored on the storage medium, and displays the radiation image other than the display target image received from the radiation image capture device on the display section.

According to an aspect of the present invention, a radiation image capture system is provided, wherein, in cases in which there are plural display target images transmitted from the radiation image capture device, the display controller displays the plural display target images on the display section in the sequence received.

According to an aspect of the present invention, a radiation image capture system is provided, wherein the display controller issues the display request based on shape recognition based on the display target image received from the radiation image capture device, and based on each of the pixel values of the display target image received from the radiation image capture device.

According to an aspect of the present invention, a radiation image capture system is provided, wherein the display target image is erased from the storage medium after the controller has received the display target image.

According to an aspect of the present invention, a radiation image capture system is provided, wherein the image stored on the storage medium is erased based on an instruction from the controller.

According to the present invention, the waiting time until the image is displayed on the external display device can be made shorter than conventional waiting times, while avoiding the risk of image recapture when an image generated by some radiation detection panels, out of plural radiation detection panels lined up in a direction orthogonal to the incidence direction of the radiation, is displayed on a display section of an external device.

What is claimed is:

1. A radiation image capture device comprising:
a plurality of radiation detection panels that each detect a same single dose of incident radiation that has passed through an imaging subject, that each generate a radiation image, and that are disposed in a row in a direction orthogonal to the radiation incident direction;
a designation section that designates a display target image from a plurality of radiation images respectively generated by the plurality of radiation detection panels; and
a transmission section that transmits to the outside of the radiation image capture device at least the display target image from the plurality of radiation images;
wherein the plurality of respective radiation detection panels are disposed such that end portions of image capture regions are able to generate radiation images overlapping with mutually adjacent radiation detection panels.

2. The radiation image capture device of claim 1, wherein the designation section designates the display target image based on detection signals from respective sensors that are provided corresponding to each of the plurality of radiation detection panels and output detection signals of magnitude according to a dose of irradiated radiation.

3. The radiation image capture device of claim 1, wherein the designation section designates the display target image based on attribute data indicating attributes of the imaging subject.

4. The radiation image capture device of claim 1, wherein the designation section designates the display target image based on data supplied from the outside of the radiation image capture device designating the display target image.

5. The radiation image capture device of claim 1, wherein:
an external device outside of the radiation image capture device determines the presence or absence of an imaging subject on each of the radiation detection panels based on detection signals from respective sensors that are provided to correspond to each of the plurality of radiation detection panels and output detection signals of magnitude according to a dose of irradiated radiation; and
the designation section designates the display target image based on the determination result of the presence or absence of the subject image by the external device.

6. The radiation image capture device of claim 1, wherein in cases in which a plurality of images have been designated as display target images, the transmission section derives a transmission sequence for the plurality of display target images and transmits to the outside of the radiation image capture device the plurality of display target images in sequence according to the derived transmission sequence.

7. The radiation image capture device of claim 6, wherein the transmission section derives the transmission sequence for the plurality of display target images based on detection signals from respective sensors that are provided corresponding to each of the plurality of radiation detection panels and output detection signals of magnitude according to a dose of irradiated radiation.

8. The radiation image capture device of claim 6, wherein the transmission section derives the transmission sequence of the plurality of display target images based on attribute data indicating attributes of the imaging subject.

9. The radiation image capture device of claim 1, wherein in cases in which a plurality of images have been designated as display target images, the transmission section transmits to the outside of the radiation image capture device the plurality of display target images in sequence according to a transmission sequence represented by data supplied from the outside of the radiation image capture device designating the transmission sequence for each of the plurality of display target images.

10. The radiation image capture device of claim 1, wherein, in cases in which a plurality of images have been designated as display target images:
an external device outside of the radiation image capture device derives a transmission sequence for the plurality of display target images based on detection signals from respective sensors that are provided corresponding to each of the plurality of radiation detection panels and output detection signals of magnitude according to a dose of irradiated radiation; and
the transmission section transmits to the outside of the radiation image capture device the plurality of display target images in sequence according to the transmission sequence derived by the external device.

11. The radiation image capture device of claim 6, wherein:
the transmission section transmits to the outside of the radiation image capture device the latter transmitted image, from two display target images respectively generated by two mutually adjacent radiation detection panels, in sequence from the end portion on the side adjacent to the previously transmitted image.

12. The radiation image capture device of claim 9, wherein:
the transmission section transmits to the outside of the radiation image capture device the latter transmitted image, from two display target images respectively generated by two mutually adjacent radiation detection panels, in sequence from the end portion on the side adjacent to the previously transmitted image.

13. The radiation image capture device of claim 10, wherein:
the transmission section transmits to the outside of the radiation image capture device the latter transmitted image, from two display target images respectively generated by two mutually adjacent radiation detection panels, in sequence from the end portion on the side adjacent to the previously transmitted image.

14. The radiation image capture device of claim 1, wherein:
the transmission section transmits to the outside of the radiation image capture device an image portion included in a specific range originating at an end portion on a side adjacent to the display target image in a radiation image other than the display target image.

15. The radiation image capture device of claim 1, wherein the plurality of respective radiation detection panels share detection data indicating that radiation has been detected by one of the radiation detection panels, and transition to an image capture operation of radiation images based on the detection data.

16. The radiation image capture device of claim 1, wherein:
the plurality of respective radiation detection panels are disposed such that end portions of image capture regions are able to generate radiation images overlapping in the radiation irradiation direction with mutually adjacent radiation detection panels; and out of radiation images generated by a first radiation detection panel that is disposed at the radiation irradiation direction downstream side out of plural radiation detection panels and that generates the display target image, and by an adjacent second radiation detection panel that is disposed at the radiation irradiation direction upstream side and that generates a radiation image other than the display target image, a transmission section transmits to the outside of the radiation image capture device at least an image portion corresponding to an overlapping portion where the image capture region of the first radiation detection panel and the image capture region of the second radiation detection panel overlap with each other as an image for use in correction.

17. The radiation image capture device of claim 1, wherein, based on data representing at least one selected from the group consisting of an attribute of a subject imaging, the plurality of radiation images, and an image capture condition, the transmission section identifies a spread range of an imaging subject based on a point spread function, and in cases in which the identified subject image spread range is included in a radiation image other than the display target image, out of the radiation image other than the display target image, at least an image portion including the spread range of the subject image is transmitted to the outside of the radiation image capture device as an image for use in correction.

18. The radiation image capture device of claim 1, further comprising a storage medium that stores at least a radiation image other than the display target image from the plurality of radiation images, wherein
    the transmission section transmits to the outside of the radiation image capture device the display target image from the plurality of radiation images.

19. A radiation image capture system comprising:
    the radiation image capture device of claim 1;
    a storage medium that stores at least a radiation image other than the display target image from the plurality of radiation images; and
    a controller including a display controller that displays the display target image received from the radiation image capture device on a display section, and in cases in which a display request has been made, displays on the display section together with the display target image the radiation image other than the display target image stored on the storage medium.

20. A radiation image capture system comprising:
    the radiation image capture device of claim 16;
    a storage medium that stores at least a radiation image other than the display target image from the plurality of radiation images; and
    a controller including a display controller that displays the display target image received from the radiation image capture device on a display section, and in cases in which a display request has been made, displays on the display section together with the display target image the radiation image other than the display target image stored on the storage medium, and corrects the display target image generated by the first radiation detection panel using the image for use in correction.

21. The radiation image capture system of claim 20, wherein:
    the display controller displays image portions of the display target image generated by the first radiation detection panel not corresponding to the overlapping portion on the display section prior to displaying the image portion corresponding to the overlapping portion, and displays the image portion corresponding to the overlapping portion on the display section after being corrected using the image for use in correction.

22. A radiation image capture system comprising:
    the radiation image capture device of claim 17;
    a storage medium that stores at least a radiation image other than the display target image from the plurality of radiation images; and
    a controller including a display controller that displays the display target image received from the radiation image capture device on a display section, and in cases in which a display request has been made, displays on the display section together with the display target image the radiation image other than the display target image stored on the storage medium, and corrects the display target image using the image for use in correction.

23. A radiation image capture system comprising:
    the radiation image capture device of claim 18; and
    a controller including a display controller that displays the display target image received from the radiation image capture device on a display section, and in cases in which a display request has been made, requests the radiation image capture device to transmit the radiation image other than the display target image stored on the storage medium, and displays the radiation image other than the display target image received from the radiation image capture device on the display section.

24. The radiation image capture system of claim 19, wherein:
    in cases in which there are a plurality of display target images transmitted from the radiation image capture device, the display controller displays the plurality of display target images on the display section in the sequence received.

25. The radiation image capture system of claim 19, wherein the display controller issues the display request based on shape recognition based on the display target image received from the radiation image capture device, and based on each of the pixel values of the display target image received from the radiation image capture device.

26. The radiation image capture system of claim 19, wherein the display target image is erased from the storage medium after the controller has received the display target image.

27. The radiation image capture system of claim 19, wherein the image stored on the storage medium is erased based on an instruction from the controller.

* * * * *